(12) United States Patent
Yen

(10) Patent No.: US 9,893,305 B2
(45) Date of Patent: Feb. 13, 2018

(54) INDENOTRIPHENYLENE-BASED IRIDIUM COMPLEXES FOR ORGANIC ELECTROLUMINESCENCE DEVICE

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 416 days.

(21) Appl. No.: 14/726,603

(22) Filed: Jun. 1, 2015

(65) Prior Publication Data

US 2016/0351835 A1  Dec. 1, 2016

(51) Int. Cl.
| H01L 51/00 | (2006.01) |
| C07F 15/00 | (2006.01) |
| C09K 11/06 | (2006.01) |
| C09K 11/02 | (2006.01) |
| H01L 51/50 | (2006.01) |

(52) U.S. Cl.
CPC ...... *H01L 51/0085* (2013.01); *C07F 15/0033* (2013.01); *C09K 11/025* (2013.01); *C09K 11/06* (2013.01); *H01L 51/0067* (2013.01); *H01L 51/0072* (2013.01); *H01L 51/5016* (2013.01); *H01L 51/5024* (2013.01); *C09K 2211/185* (2013.01)

(58) Field of Classification Search
None
See application file for complete search history.

(56) References Cited

U.S. PATENT DOCUMENTS

| 8,709,615 | B2 | 4/2014 | Kottas et al. |
| 8,722,205 | B2 | 5/2014 | Xia et al. |
| 8,778,508 | B2 | 7/2014 | Kwong et al. |
| 8,795,850 | B2 | 8/2014 | Kottas et al. |
| 8,962,160 | B2 | 2/2015 | Yen et al. |
| 8,993,130 | B2 | 3/2015 | Yen et al. |
| 2013/0048975 | A1 | 2/2013 | Hong et al. |

(Continued)

FOREIGN PATENT DOCUMENTS

| WO | 2008062636 A1 | 5/2008 |
| WO | 2012091471 A2 | 7/2012 |

*Primary Examiner* — Robert S Loewe

(57) ABSTRACT

The present invention discloses an indenotriphenylene-based iridium complexes is represented by the following formula (1), the organic EL device employing the derivative as light emitting dopant of emitting layer can display good performance like as lower driving voltage and power consumption, increasing efficiency and half-life time.

formula(1)

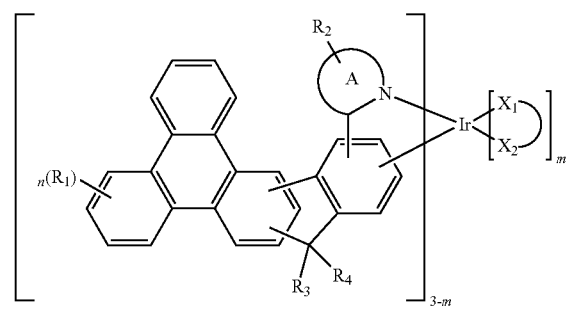

wherein A ring represents an imidazole, a pyridine, a quinoline and an isoquinoline, $X_1$-$X_2$ represents a bidentate ligand, and m, n and $R_1$ to $R_4$ are the same definition as described in the present invention.

14 Claims, 1 Drawing Sheet

| 14 | — metal electrode |
| 13 | — electron injection layer |
| 12 | — electron transport layer |
| 11 | — hole blocking layer |
| 10 | — emitting layer |
| 9 | — electron blocking layer |
| 8 | — hole transport layer |
| 7 | — hole injection layer |
| 6 | — transparent electrode |

(56) References Cited

U.S. PATENT DOCUMENTS

| | | |
|---|---|---|
| 2014/0151645 A1 | 6/2014 | Yen et al. |
| 2014/0175383 A1 | 6/2014 | Yen et al. |
| 2014/0209866 A1 | 7/2014 | Yen et al. |
| 2014/0231754 A1 | 8/2014 | Yen et al. |

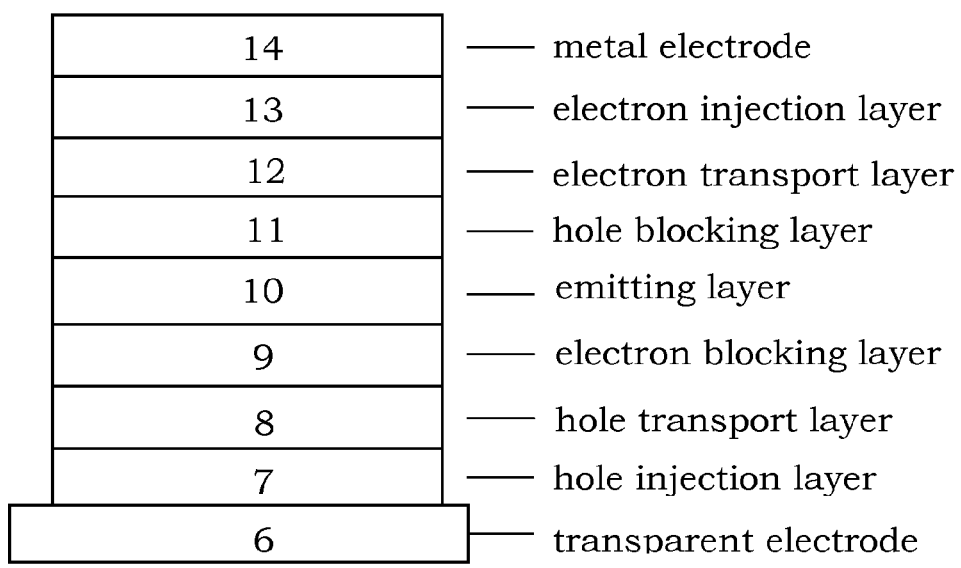

INDENOTRIPHENYLENE-BASED IRIDIUM COMPLEXES FOR ORGANIC ELECTROLUMINESCENCE DEVICE

FIELD OF INVENTION

The present invention generally relates to a indeno triphenylene-based iridium complexes and organic electroluminescence (herein referred to as organic EL) device using the iridium complexes. More specifically, the present invention relates to the indenotriphenylene-based iridium complexes having general formula (1), an organic EL device employing the iridium complexes as light emitting dopant of emitting layer.

BACKGROUND OF THE INVENTION

Organic electroluminescence (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting panel the material used for the phosphorescent dopant for emitting layer are still unsatisfactory in half-lifetime, efficiency and driving voltage. These organic metallic complexes still have disadvantages for industrial practice use.

In the present invention, for the purpose to prolong the half-life time and lower driving voltage for phosphorescent dopant in emitting layer for organic EL device, we employ an indenotriphenylene skeleton link to iridium metal, then chelate with one or two bidentate ligand to finish the metallic complexes represented as general formula (1). The iridium complexes show good thermal stability and charge carrier mobility for organic EL device. Some prior-arts of iridium complexes such as U.S. Pat. No. 8,795,850B2, U.S. Pat. No. 8,778,508B2, U.S. Pat. No. 8,722,205B2, U.S. Pat. No. 8,709,615B2. U.S. Pat. No. 8,779,176B2. But there are no prior arts demonstrate an indenotriphenylene skeleton link to iridium complexes used as light emitting dopant of emitting layer for organic EL device.

SUMMARY OF THE INVENTION

According to the reasons described above, the present invention has the objective of resolving such problems of the prior-art and offering a light emitting device which is excellent in its thermal stability, high luminance efficiency, high luminance and long half-life time. The present invention disclose a novel indenotriphenylene-based iridium complexes having general formula (1), used as a light emitting dopant of emitting layer have good charge carrier mobility and excellent operational durability can lower driving voltage and power consumption, increasing efficiency and half-life time of organic EL.

The present invention has the economic advantages for industrial practice. Accordingly, the present invention discloses the indenotriphenylene-based iridium complexes which can be used for organic EL device is disclosed. The mentioned the indenotriphenylene-based iridium complexes is represented by the following formula (1):

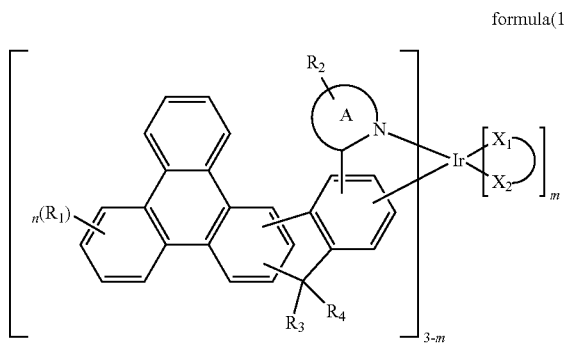

formula(1)

wherein A ring represents an imidazole, a pyridine, a quinoline and an isoquinoline, $X_1$-$X_2$ represents a bidentate ligand, m represents an integer of 0 to 2, n represents an integer of 0 to 8, $R_1$ to $R_4$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

BRIEF DESCRIPTION OF THE DRAWINGS

FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited on to 11, and 13 is electron injection layer which is deposited on to 12.

DESCRIPTION OF THE PREFERRED EMBODIMENTS

What probed into the invention is the indenotriphenylene-based iridium complexes for organic EL device using the iridium complexes. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims In a first embodiment of the present invention, the indenotriphenylene-based iridium complexes which can be used as light emitting dopant of emitting layer for organic EL device are disclosed. The mentioned the indenotriphenylene-based iridium complexes represented by the following formula (1):

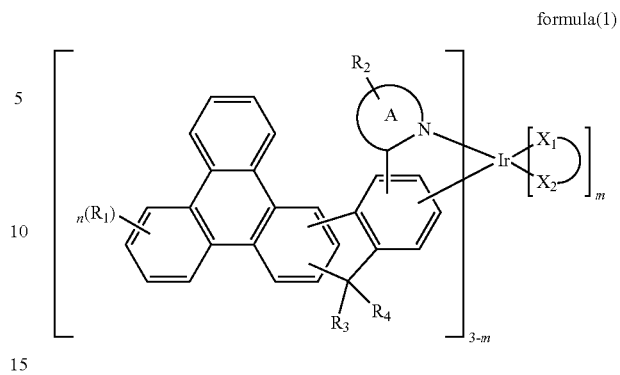

formula(1)

wherein A ring represents an imidazole, a pyridine, a quinoline and an isoquinoline, $X_1$-$X_2$ represents a bidentate ligand, m represents an integer of 0 to 2, n represents an integer of 0 to 8, $R_1$ to $R_4$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the indenotriphenylene-based iridium complexes formula (1), wherein $X_1$-$X_2$ represents the following formulas:

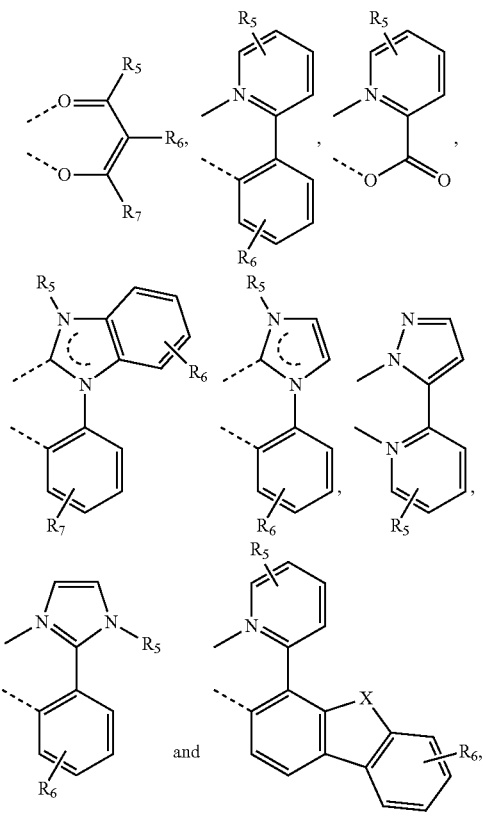

and wherein X is a divalent bridge selected from the atom or group consisting from O, S, C($R_8$)$_2$, N($R_9$) and Si($R_{10}$)$_2$, $R_5$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.
According to the above-mentioned the indenotriphenylene-based iridium complexes formula (1) represented by the following formula (2) to formula (31):
formula(2)
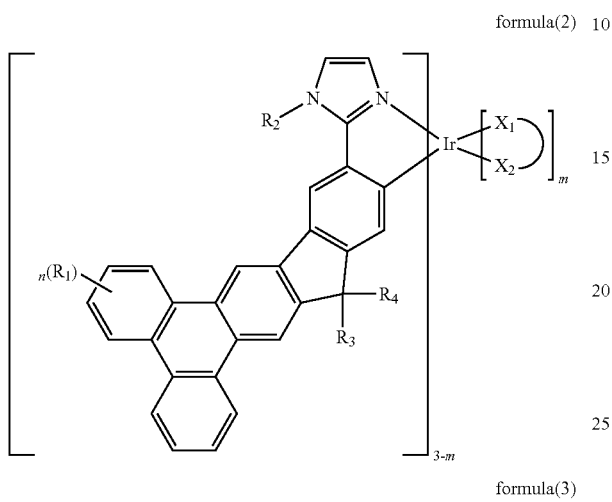
formula(3)
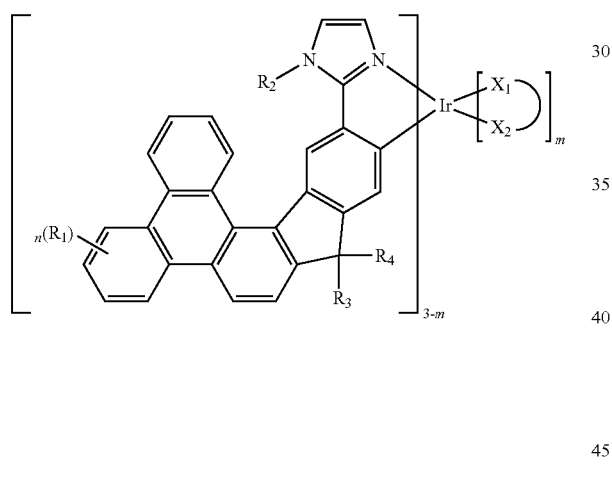
formula(4)
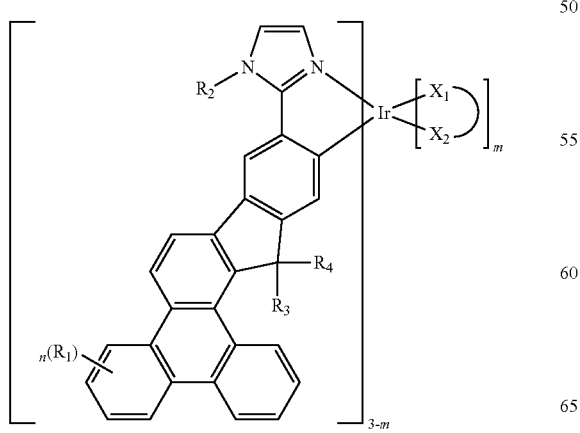
formula(5)
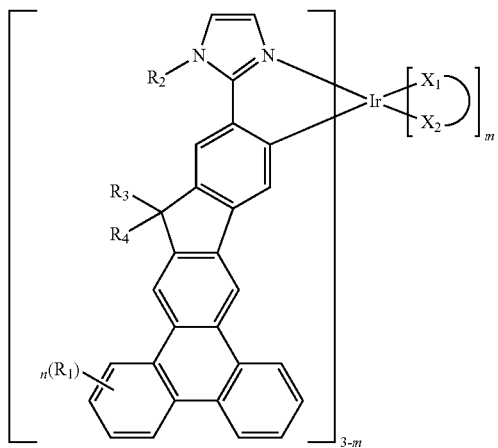
formula(6)
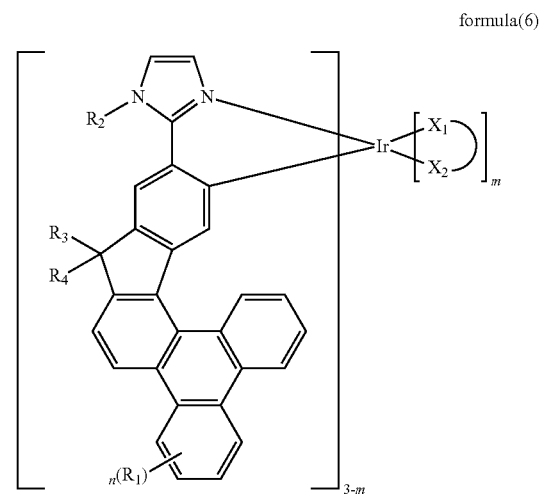
formula(7)
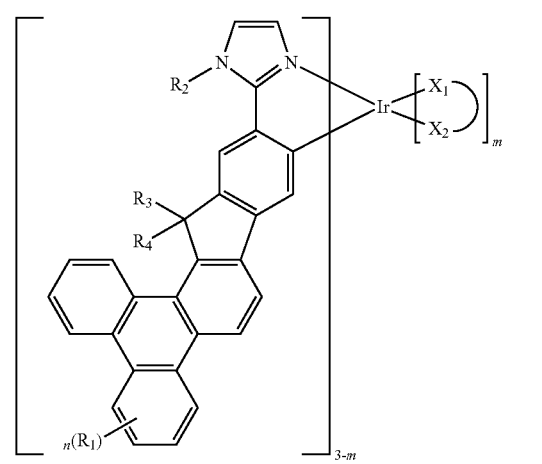

-continued
formula(8)
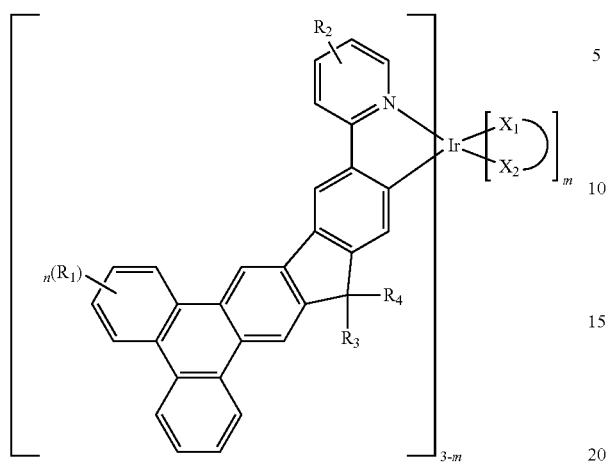
formula(9)
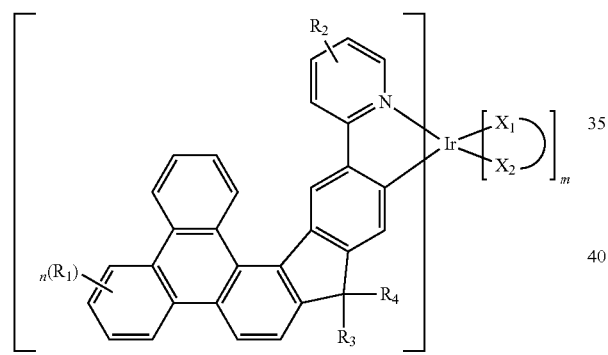
formula(10)
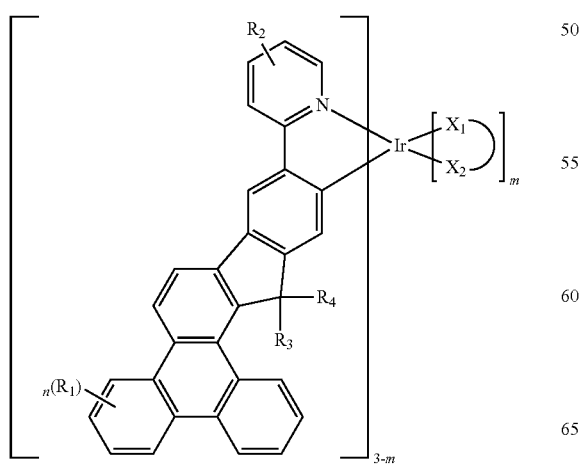
formula(11)
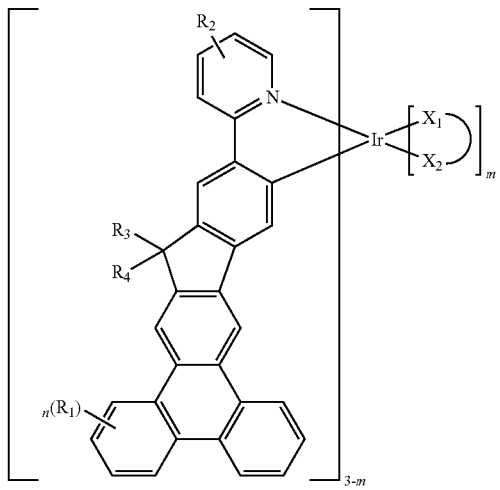
formula(12)
formula(13)
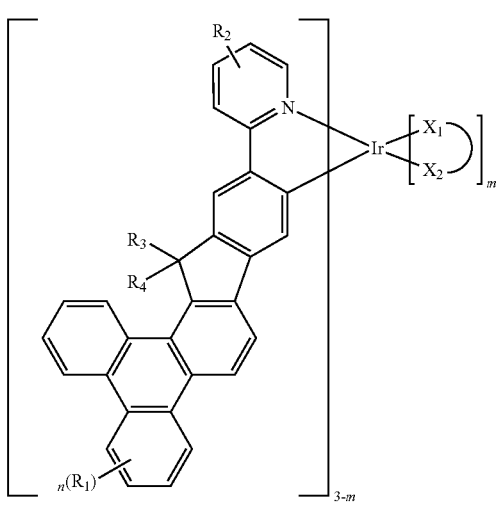

formula(14)
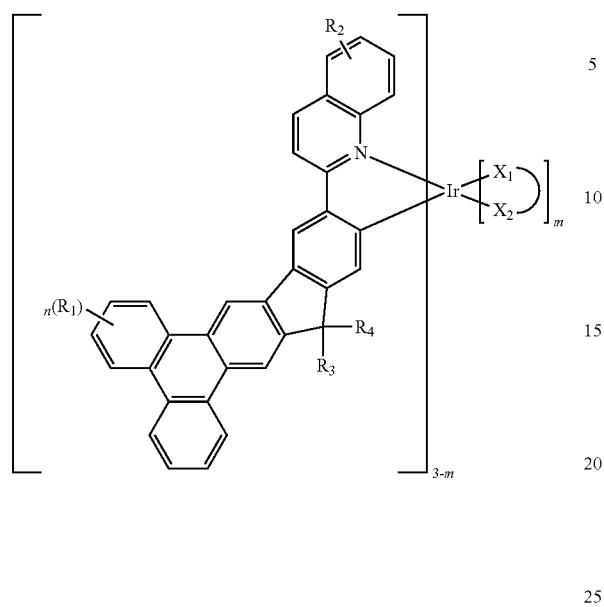
formula(15)
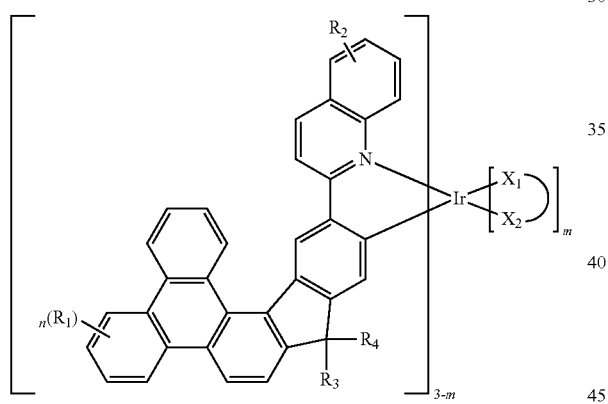
formula(16)
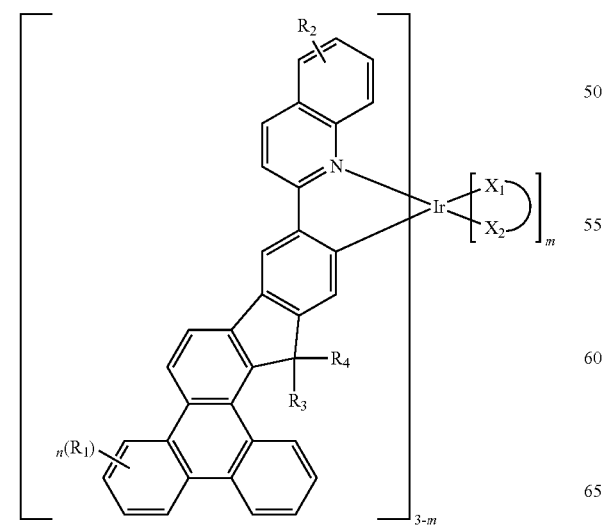
formula(17)
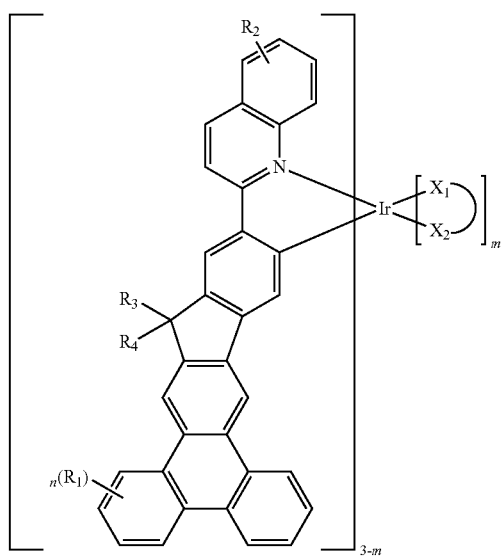
formula(18)
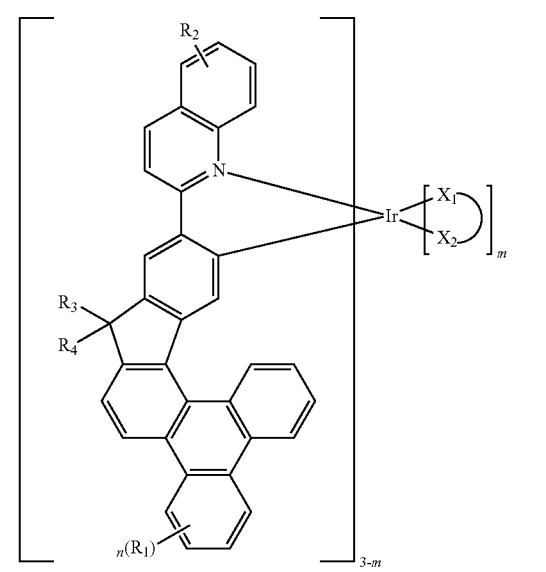

formula(19)
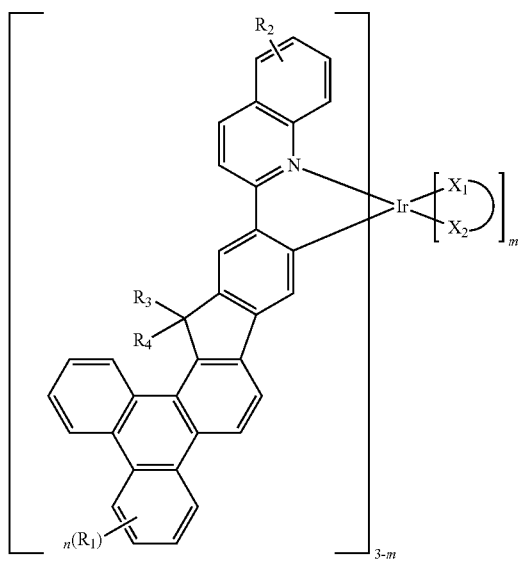
formula(20)
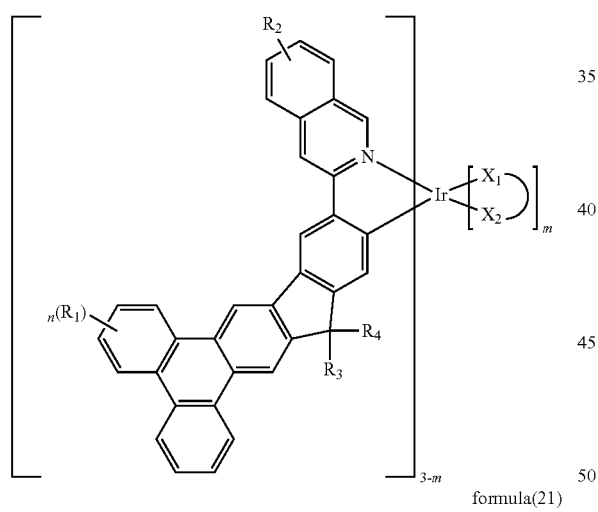
formula(21)
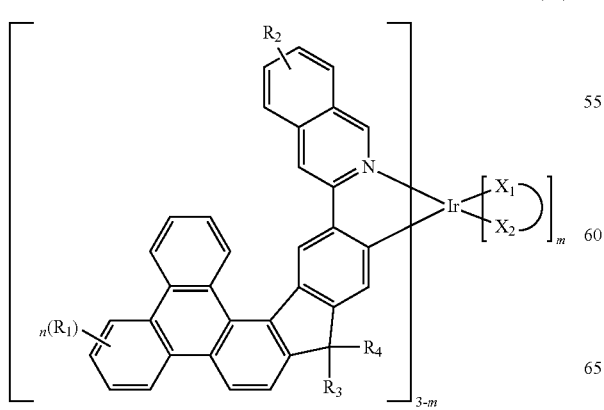
formula(22)
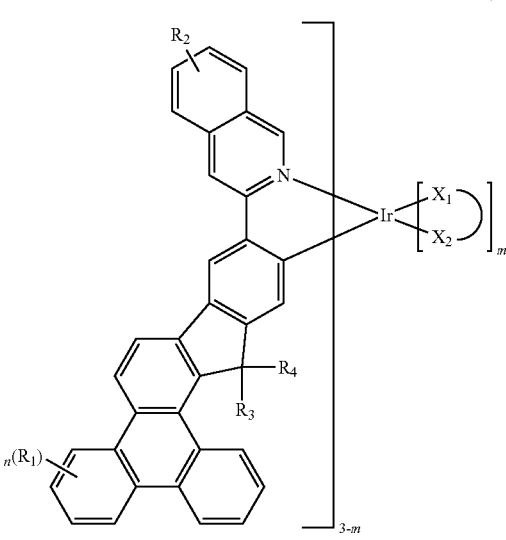
formula(23)
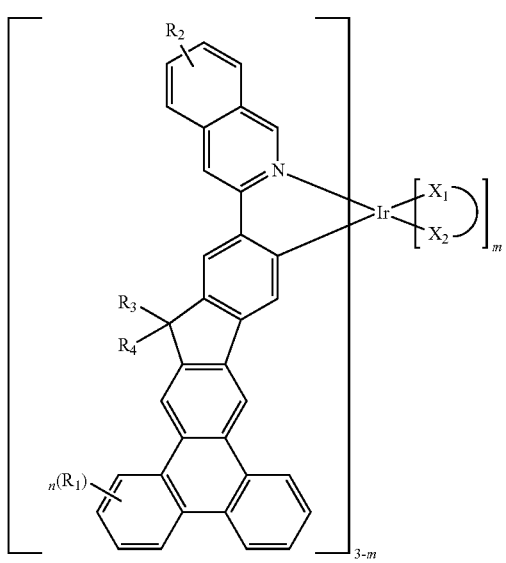

formula(24)
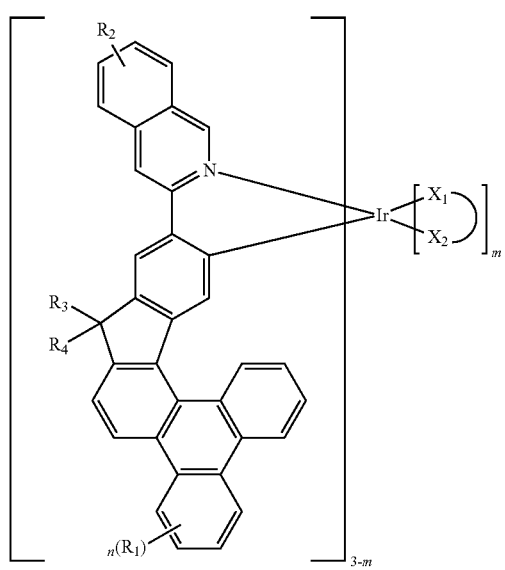
formula(25)
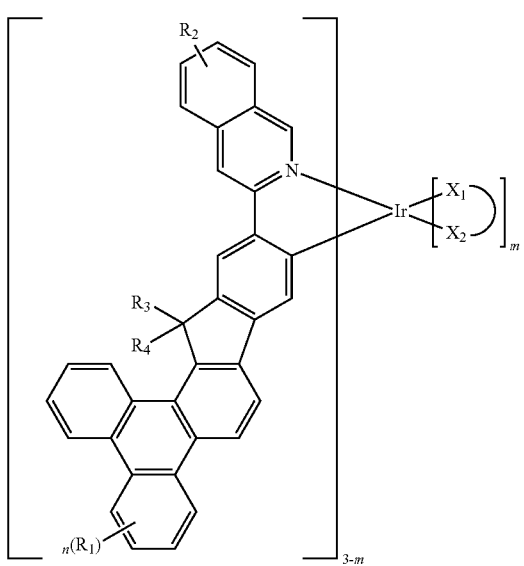
formula(26)
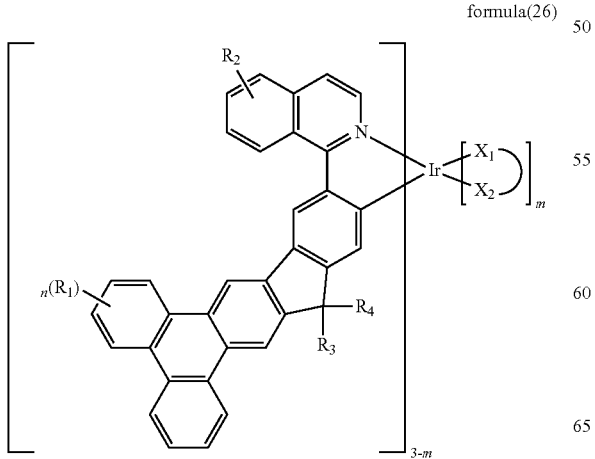
formula(27)
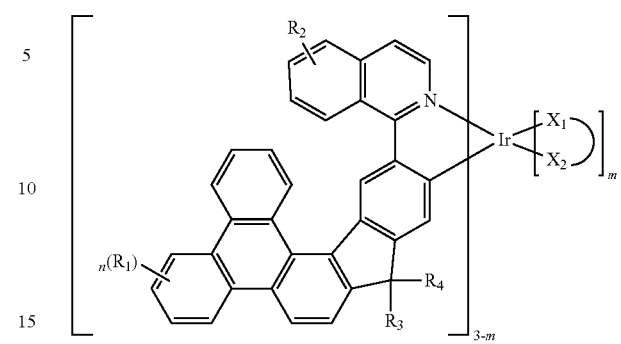
formula(28)
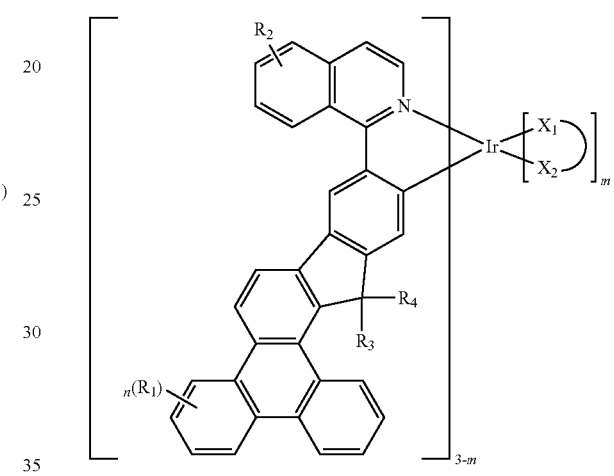
formula(29)
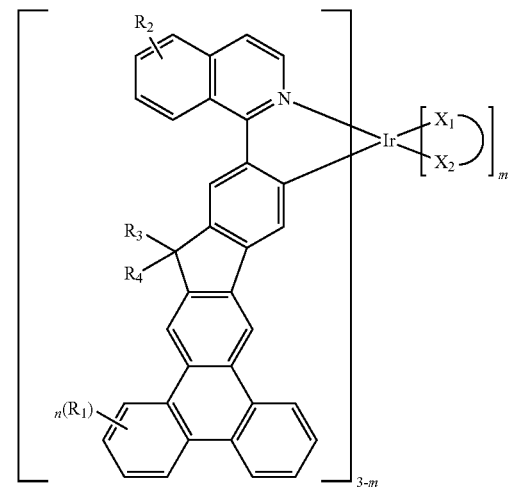

-continued formula(30)

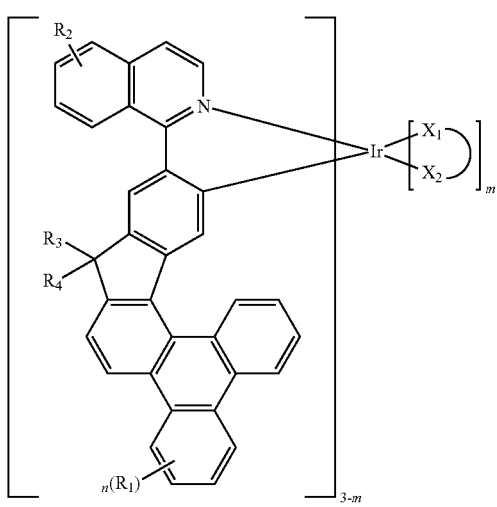

formula(31)

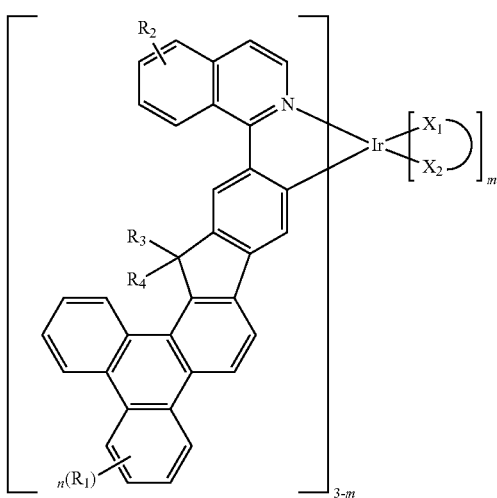

wherein $X_1$-$X_2$ represents a bidentate ligand, m represents an integer of 0 to 2, n represents an integer of 0 to 8, $R_1$ to $R_4$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the indenotriphenylene-based iridium complexes formula (2) to formula (31), wherein $X_1$-$X_2$ represents the following formulas:

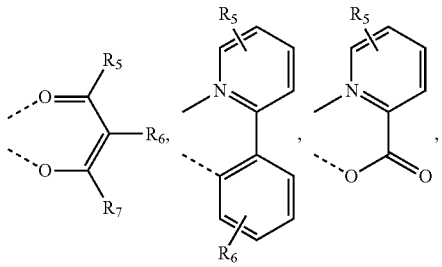

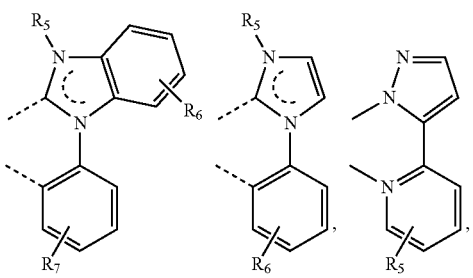

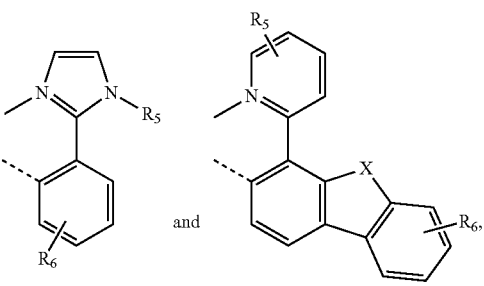

wherein X is a divalent bridge selected from the atom or group consisting from O, S, $C(R_8)_2$, $N(R_9)$ and $Si(R_{10})_2$, $R_5$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

In this embodiment, some indenotriphenylene-based iridium complexes are shown below:

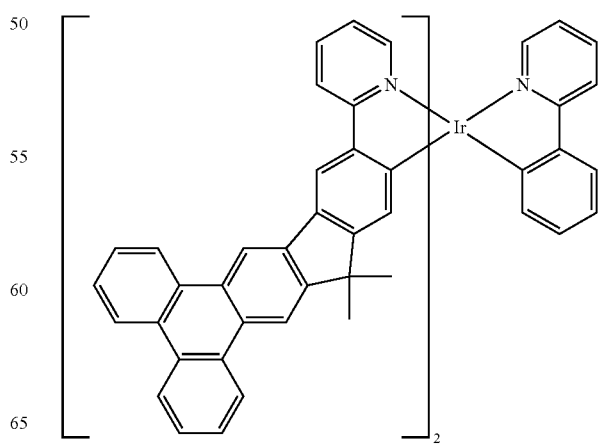

EX1

-continued
EX2
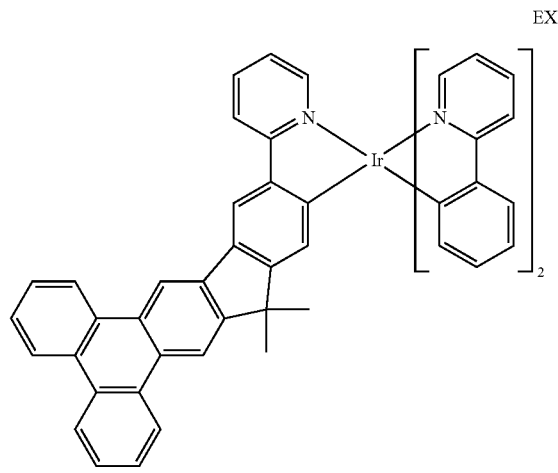
EX3
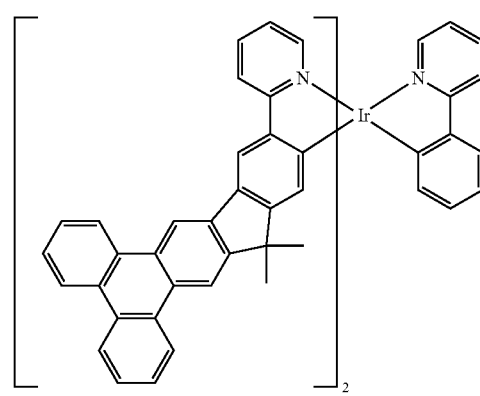
EX4
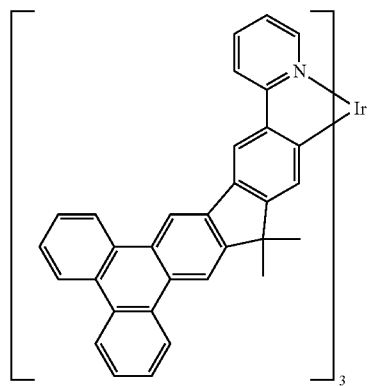
-continued
EX5
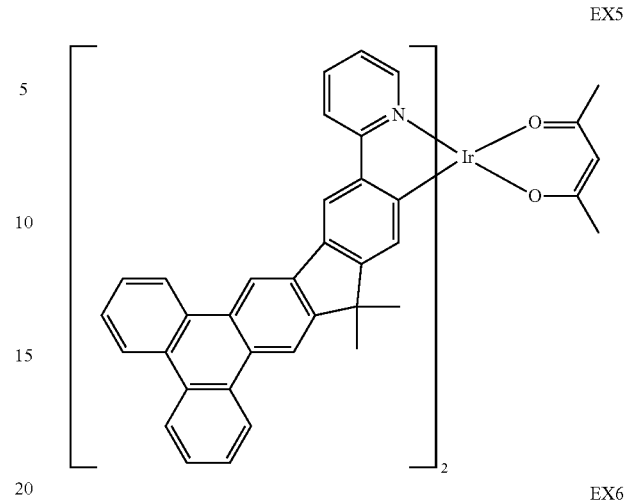
EX6
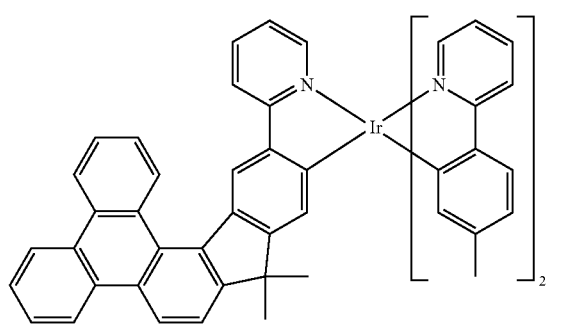
EX7
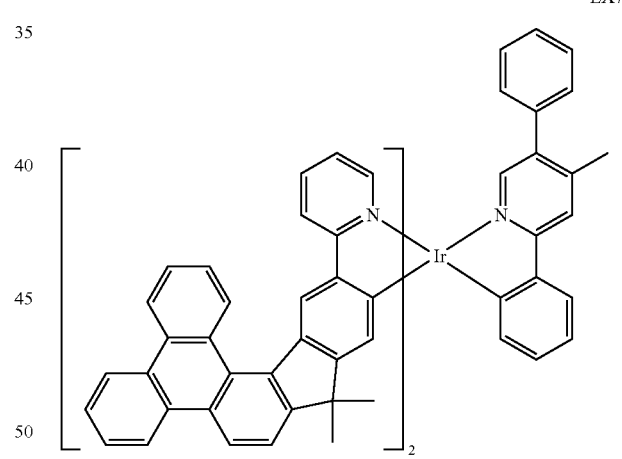
EX8
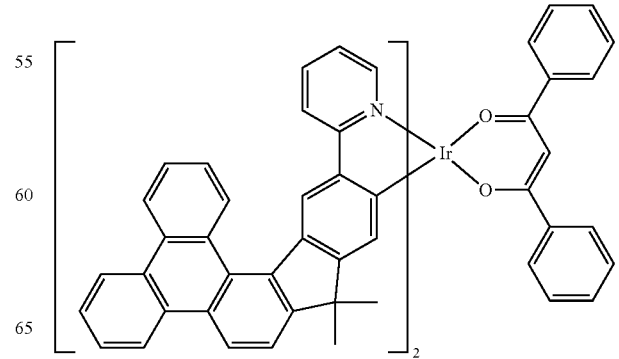

-continued
EX9
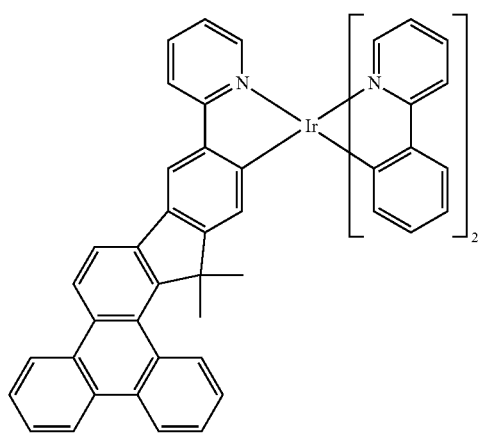
EX10
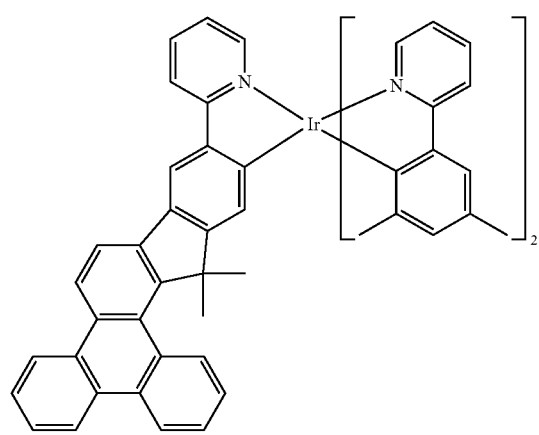
EX11
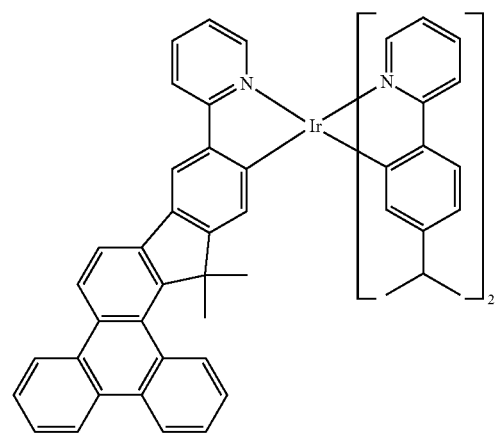
-continued
EX12
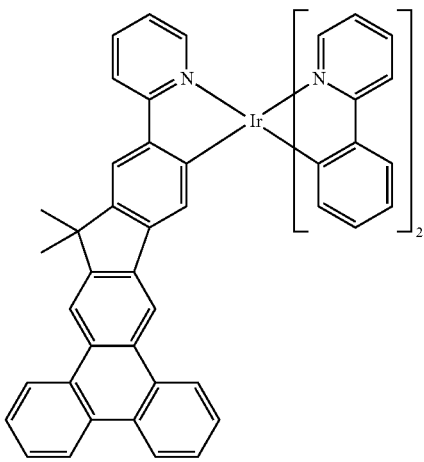
EX13
EX14
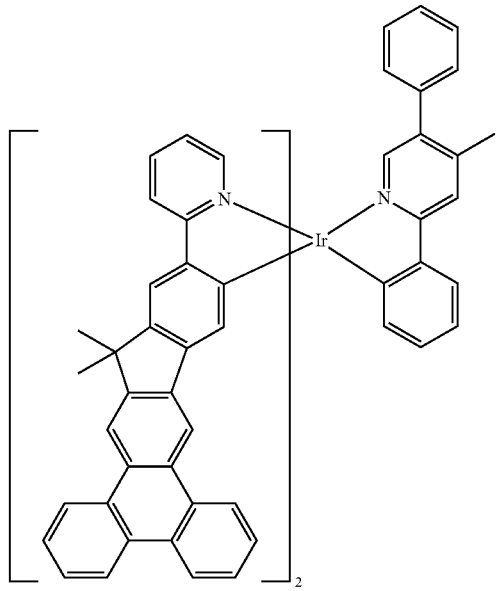

EX15
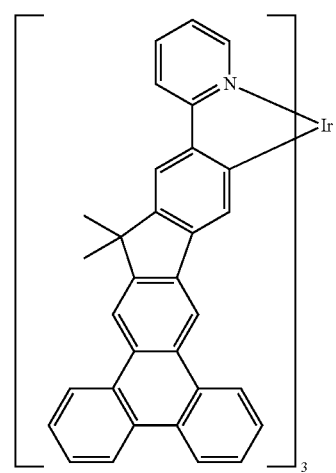
EX16
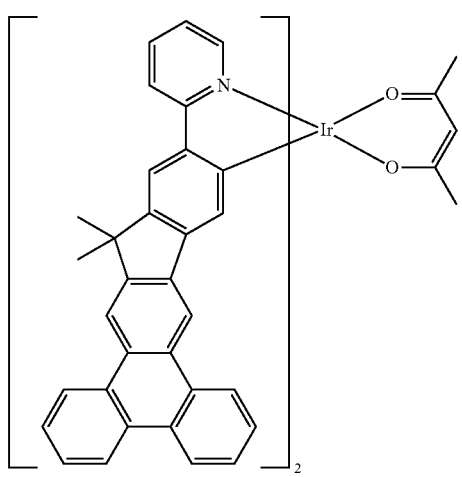
EX17
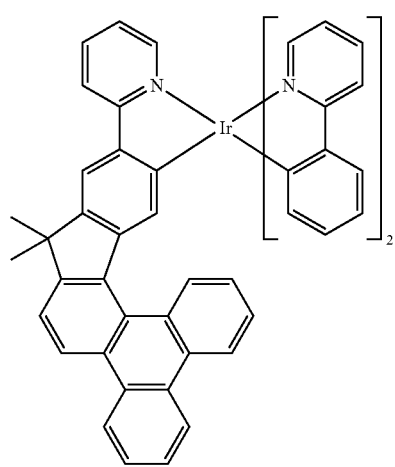
EX18
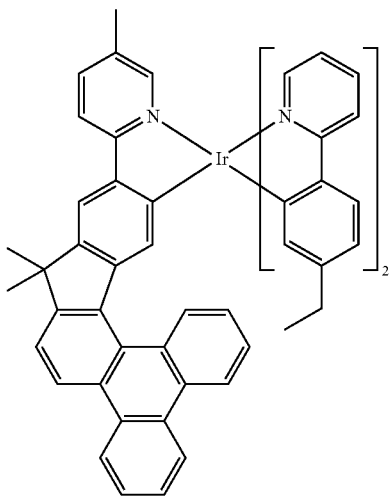
EX19
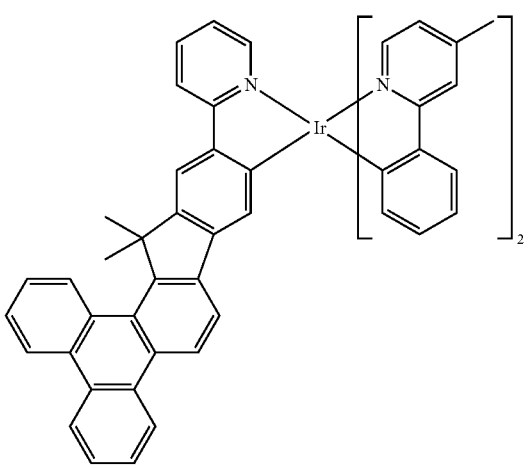
EX20
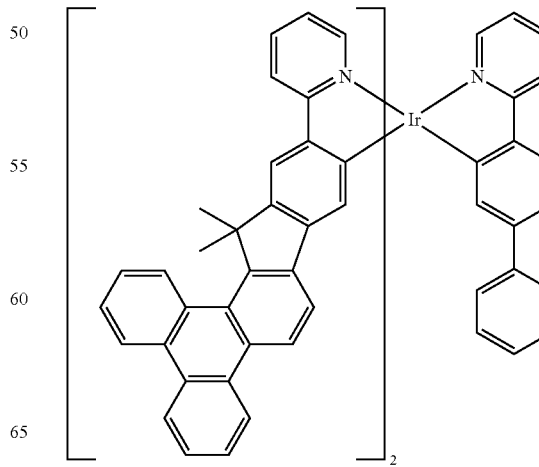

EX21
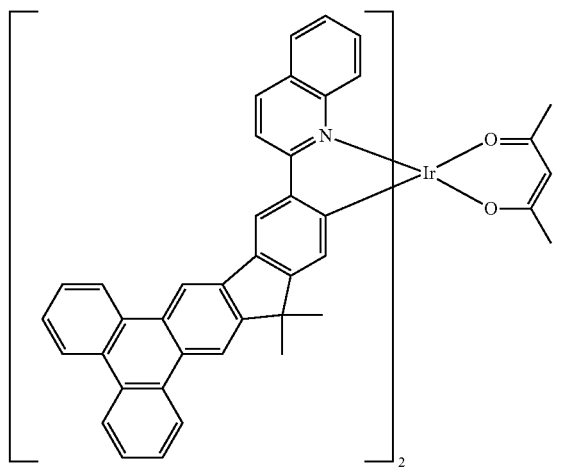
EX22
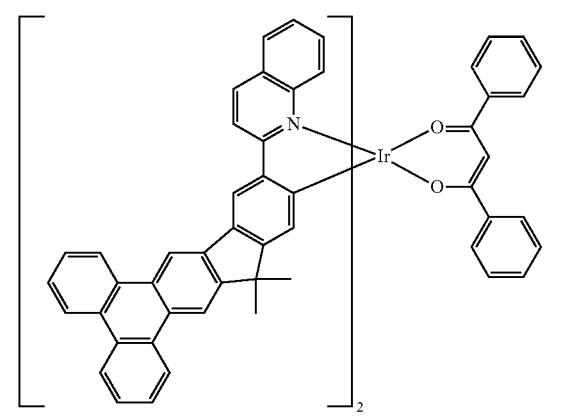
EX23
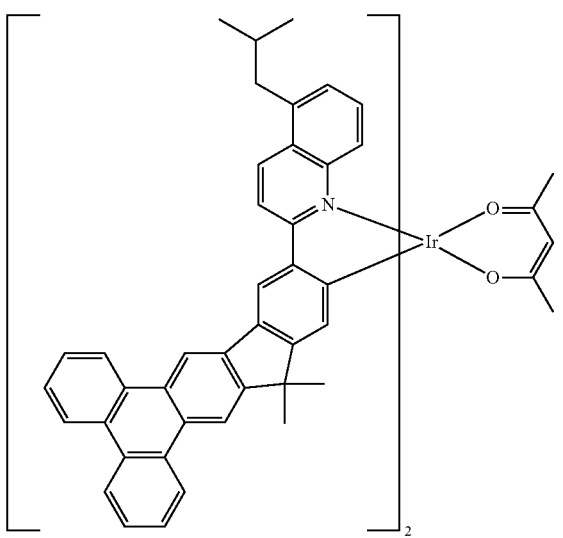
EX24
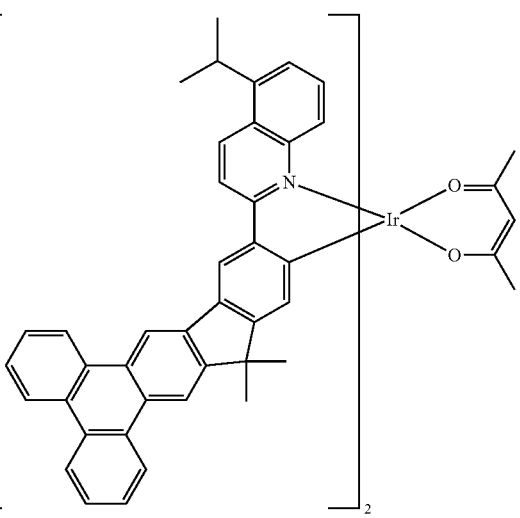
EX25
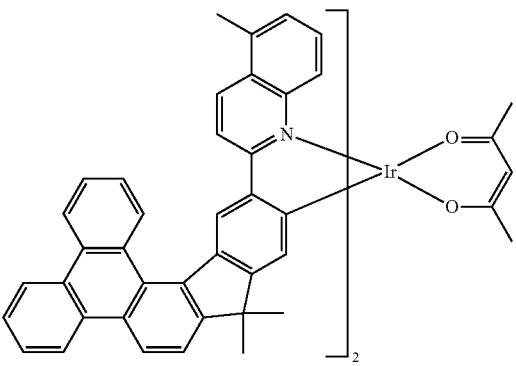
EX26
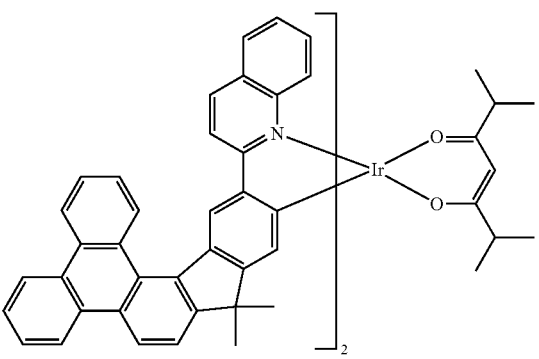

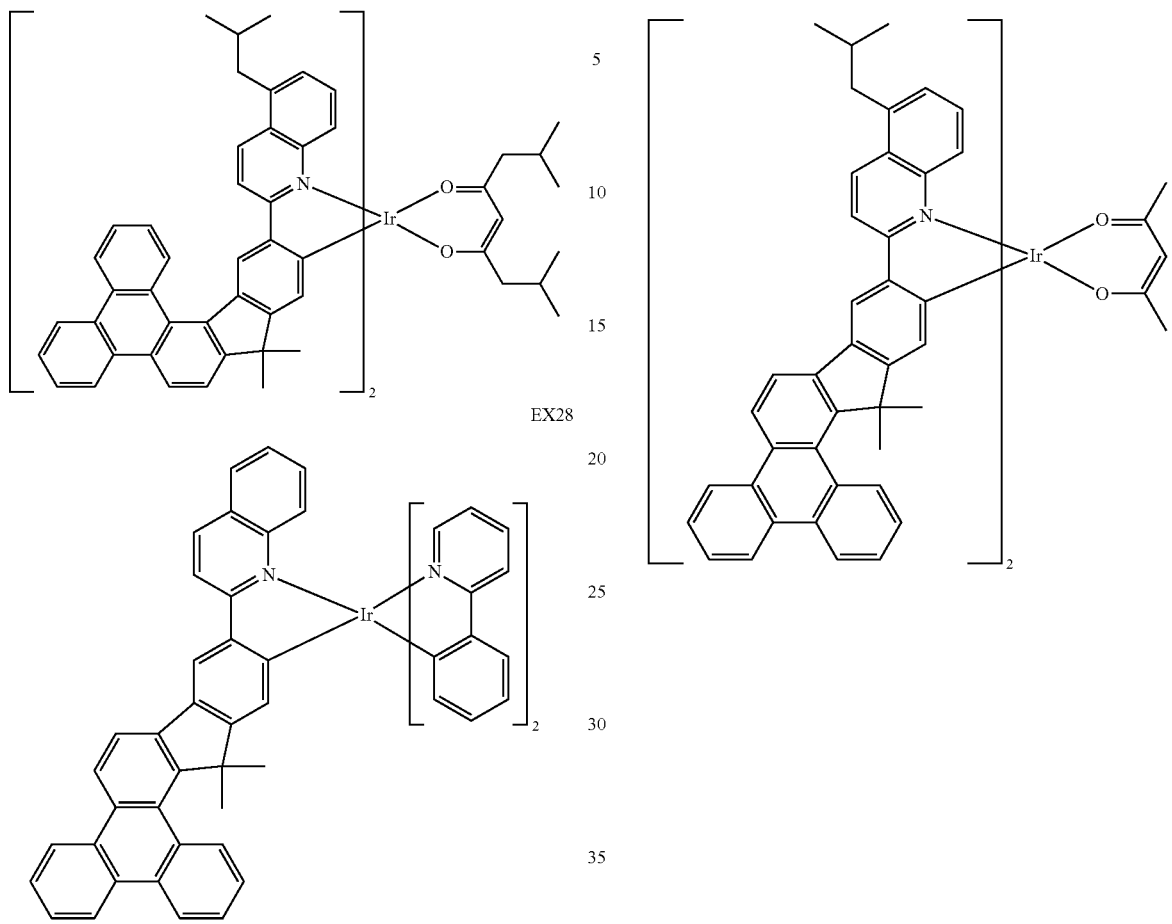
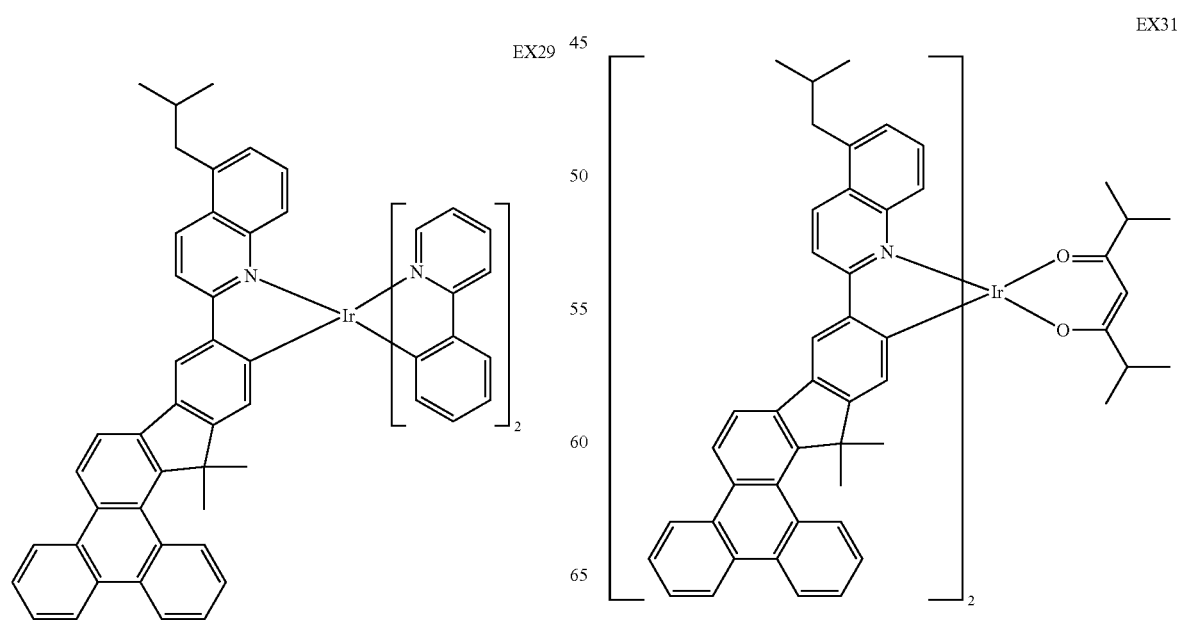

EX32
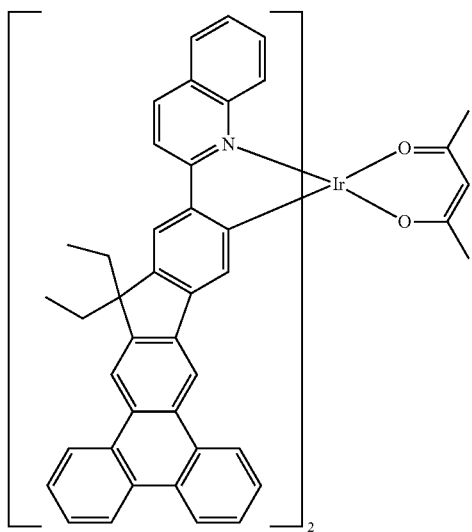
EX33
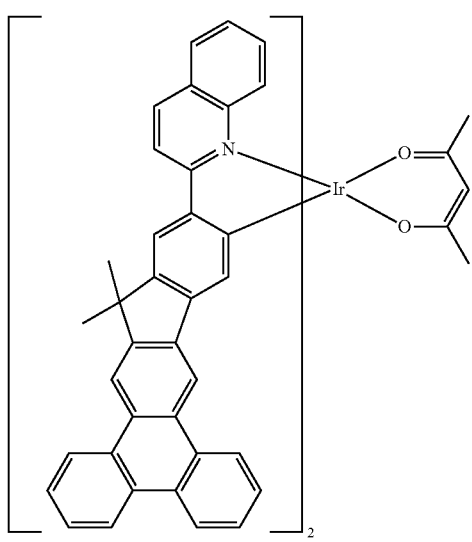
EX34
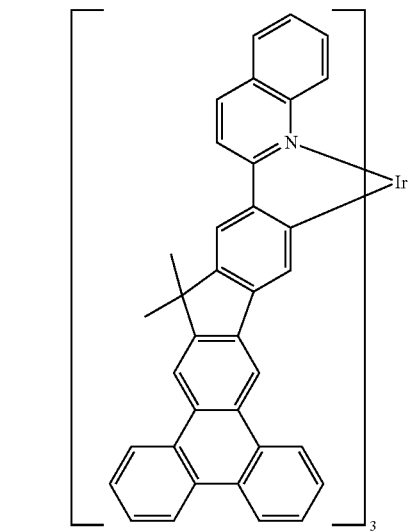
EX35
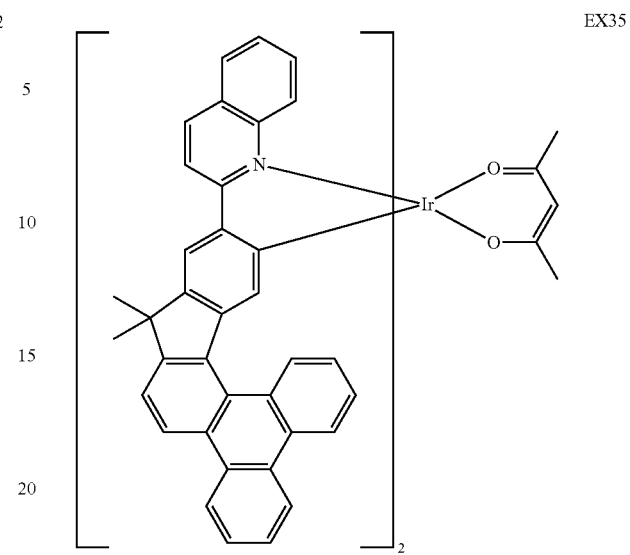
EX36
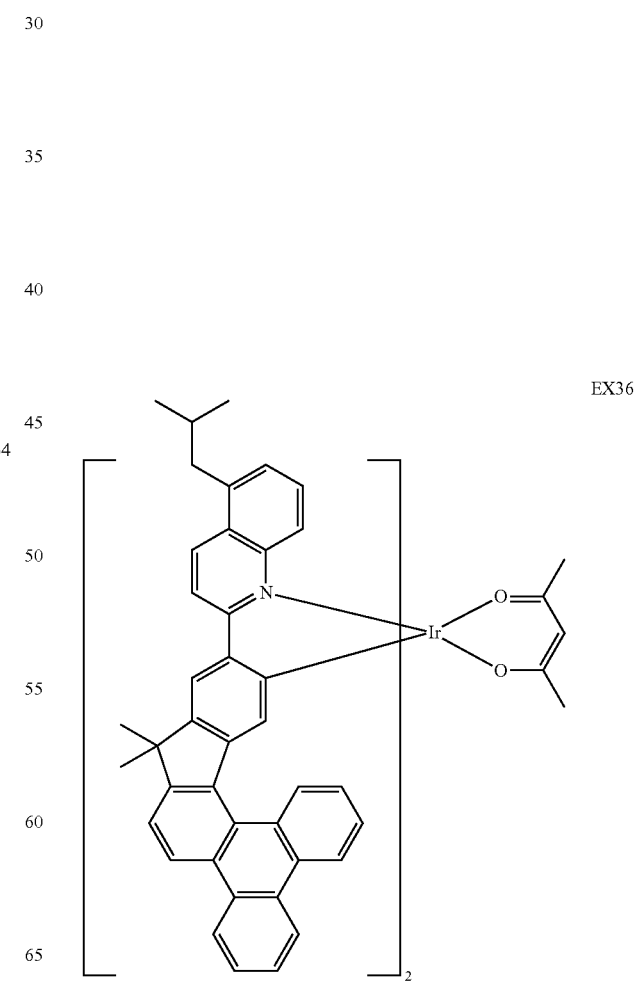

-continued
EX37
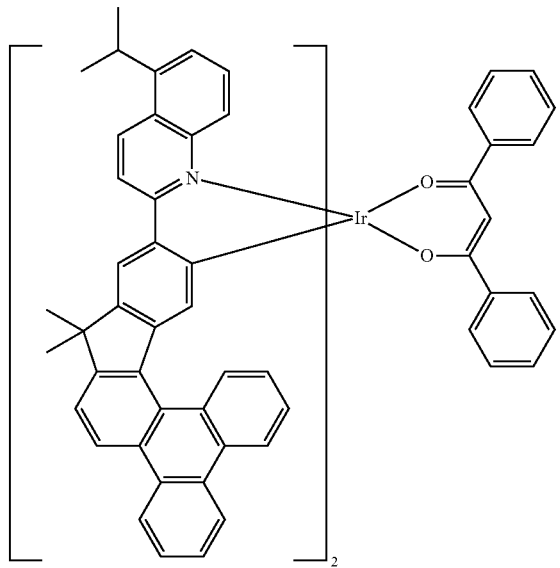
EX39
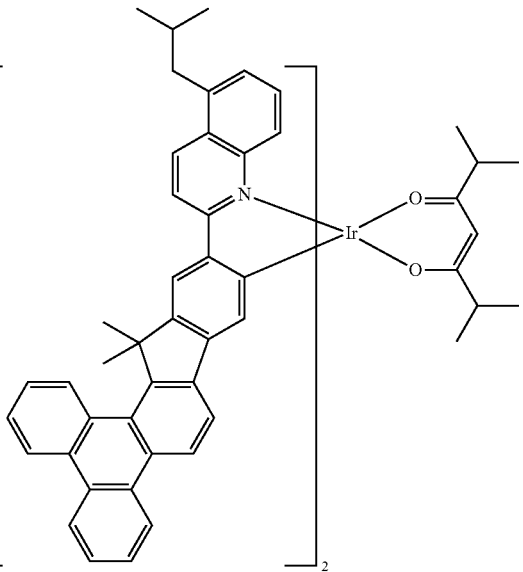
EX40
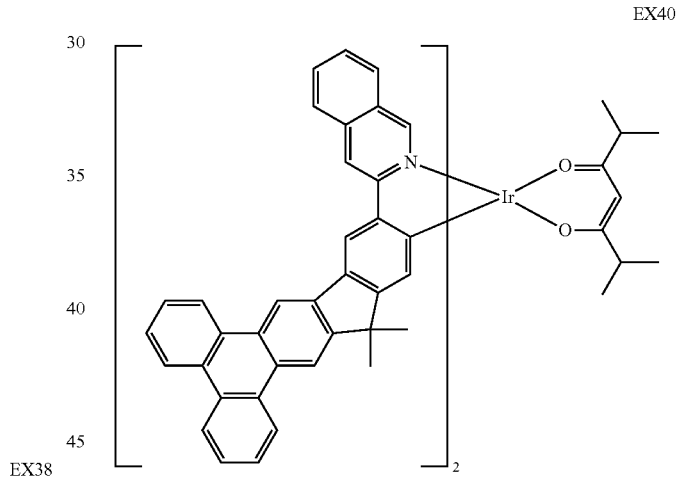
EX38
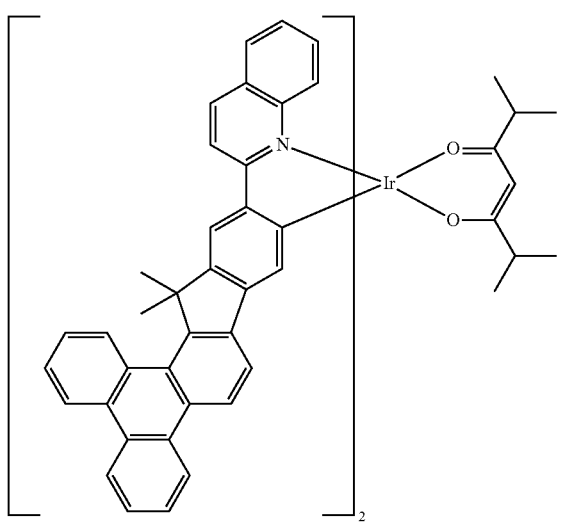
EX41
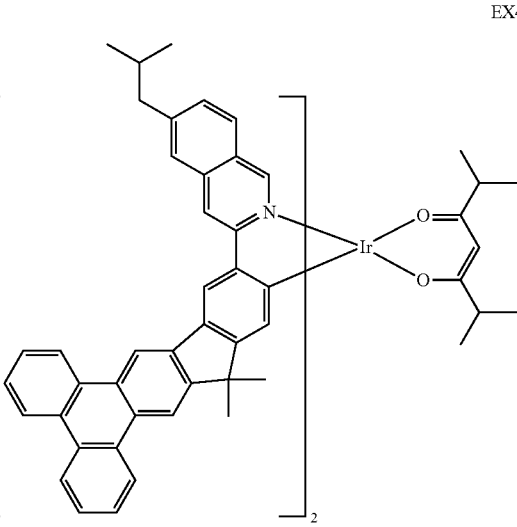

EX42
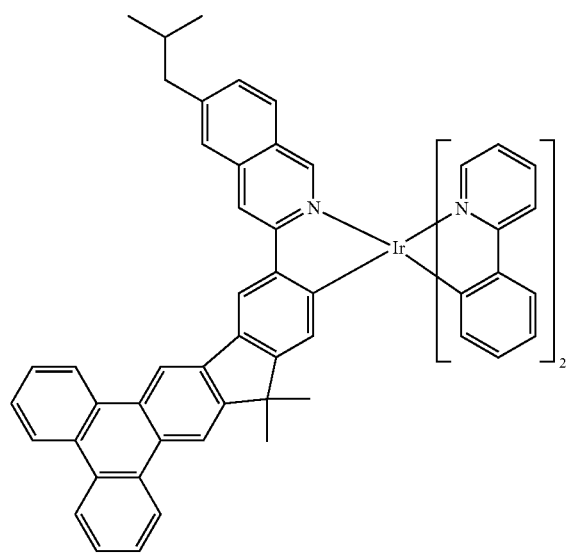
EX43
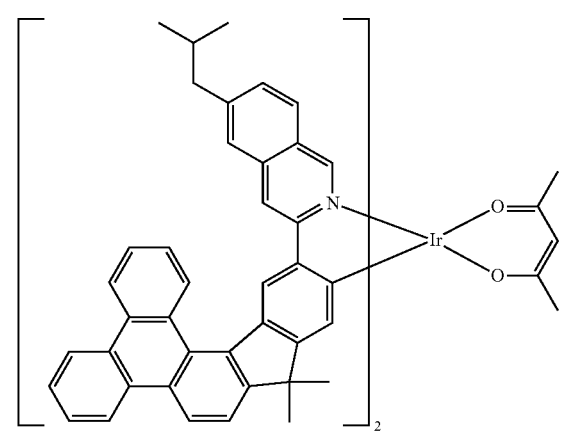
EX44
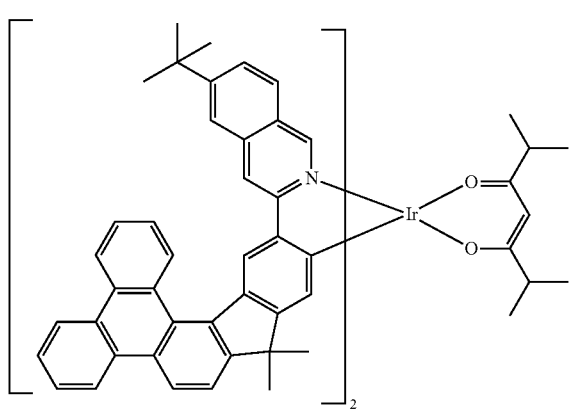
EX45
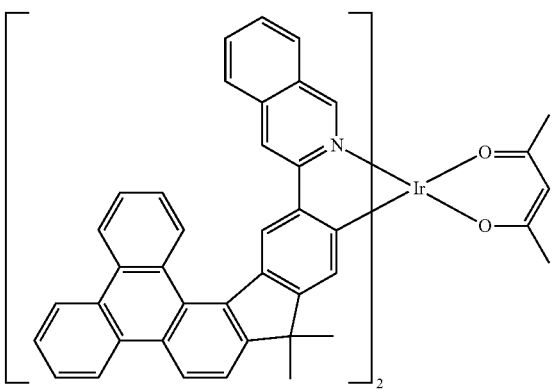
EX46
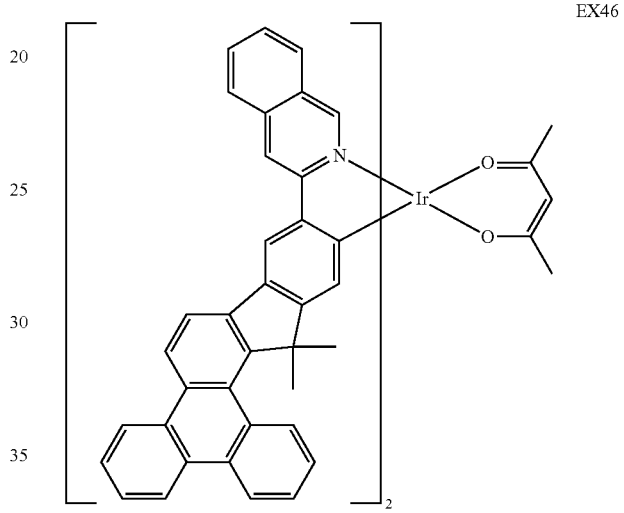
EX47
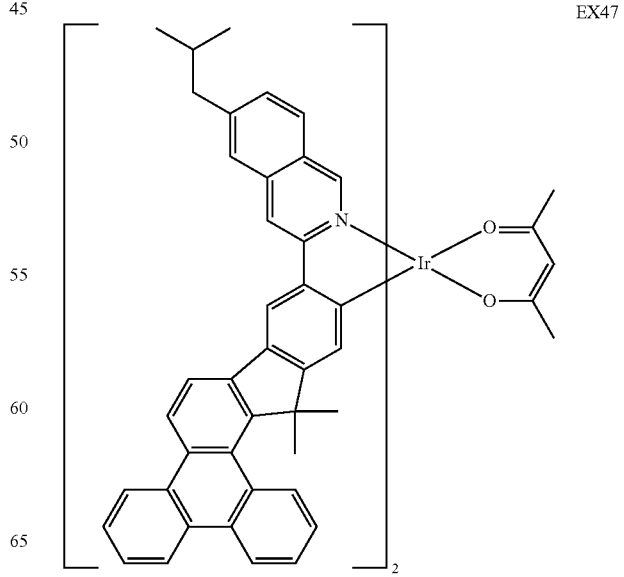

-continued
EX48
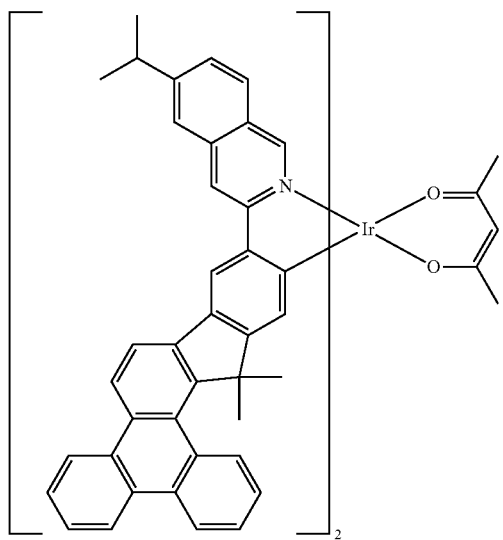
EX49
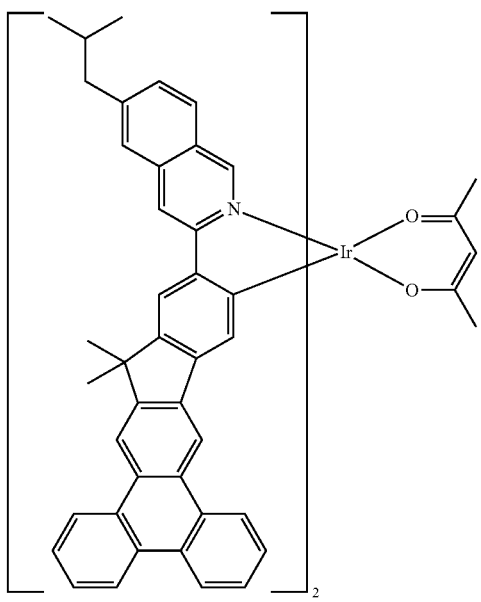
EX50
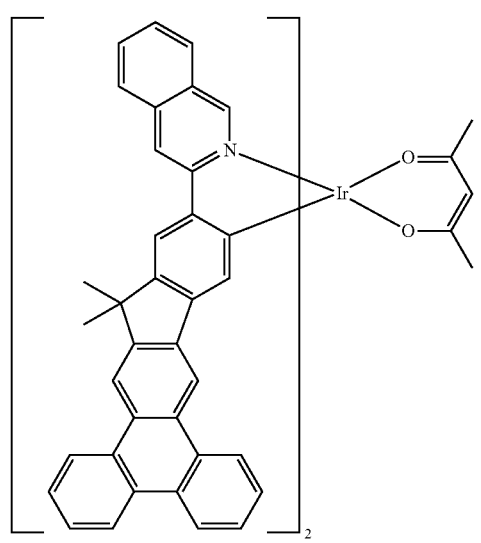
-continued
EX51
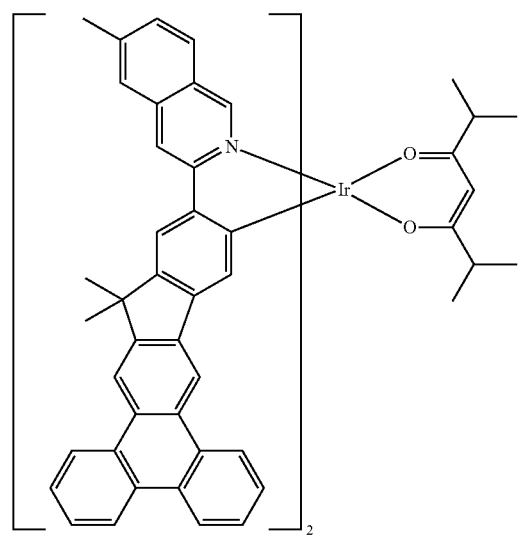
EX52
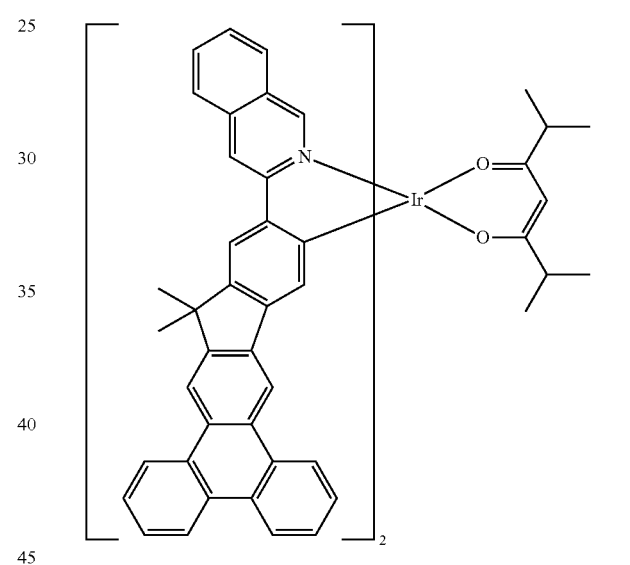
EX53
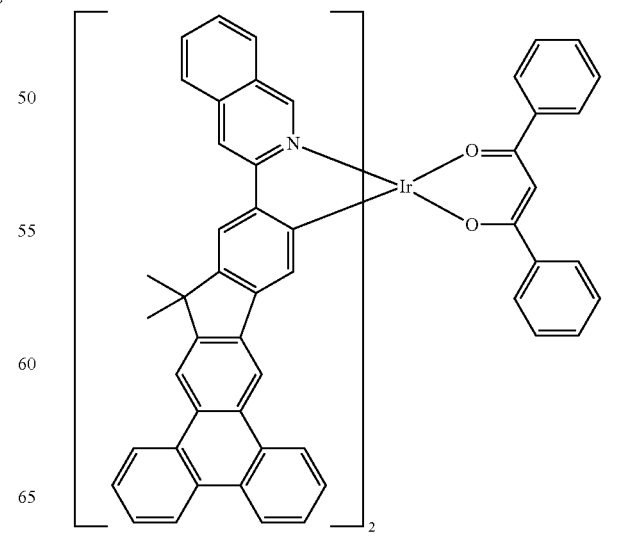

EX54
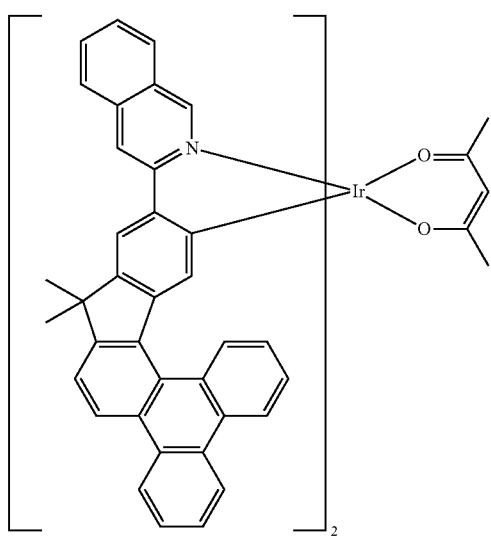
EX56
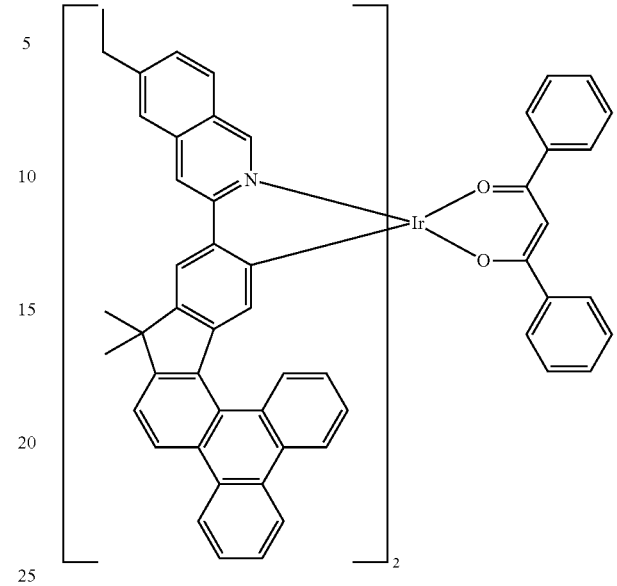
EX55
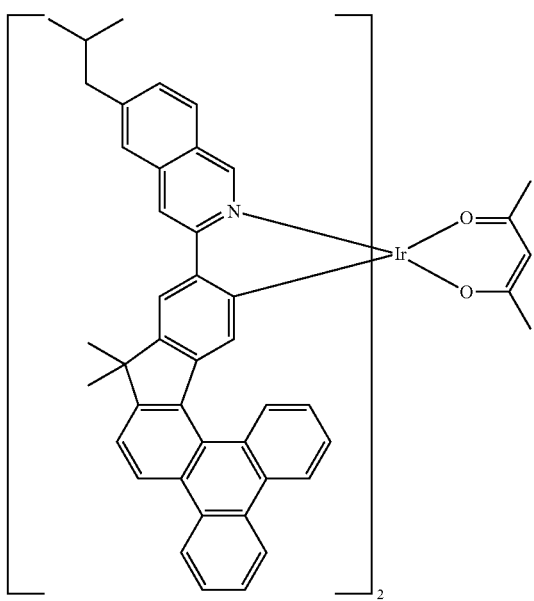
EX57
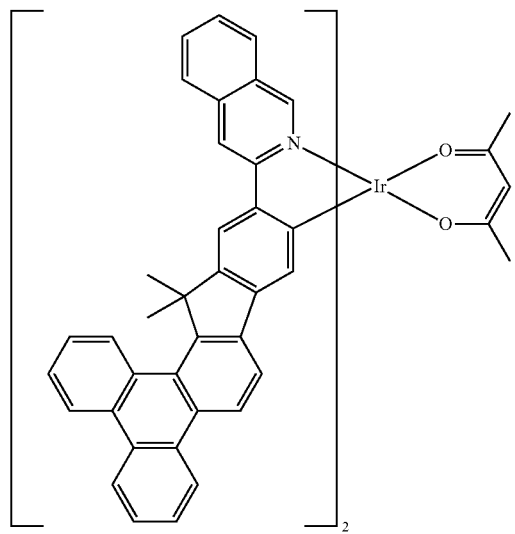

EX58
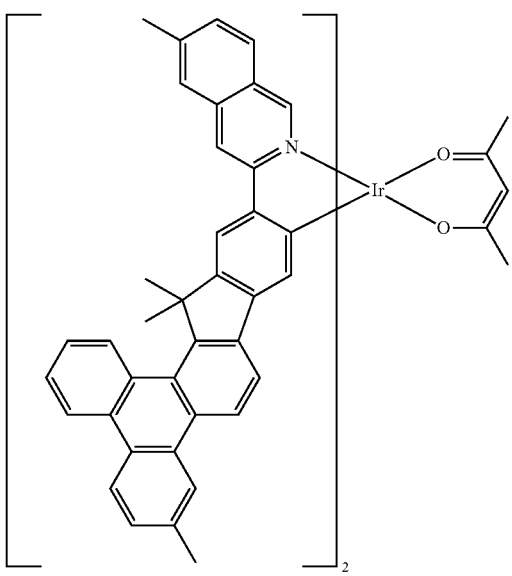
EX59
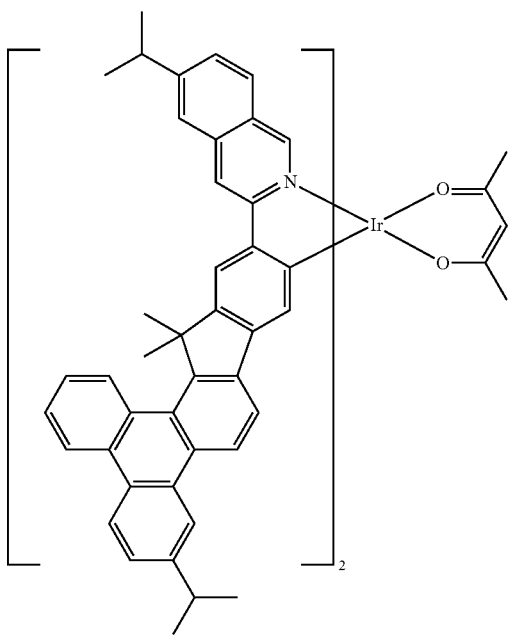
EX60
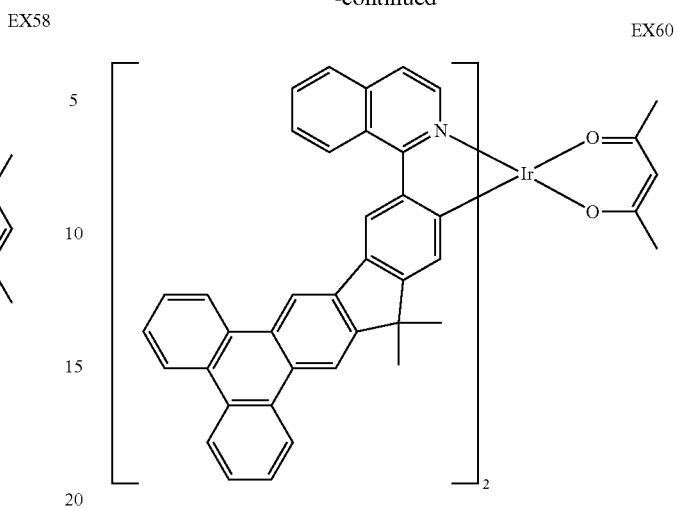
EX61
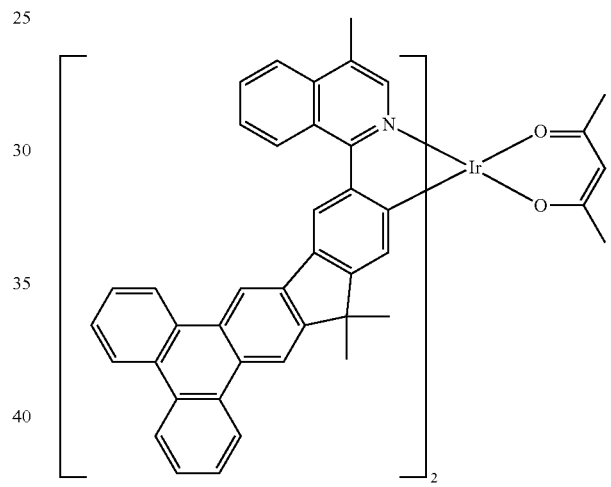
EX62
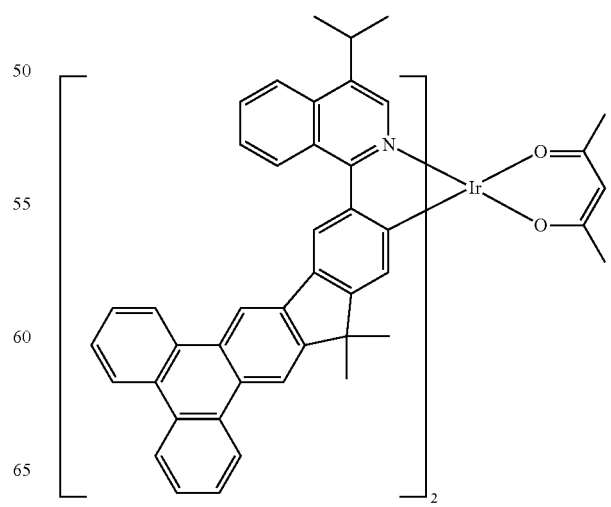

EX63
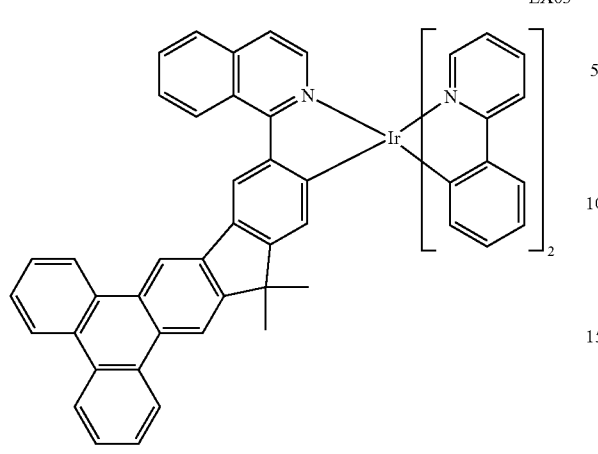
EX64
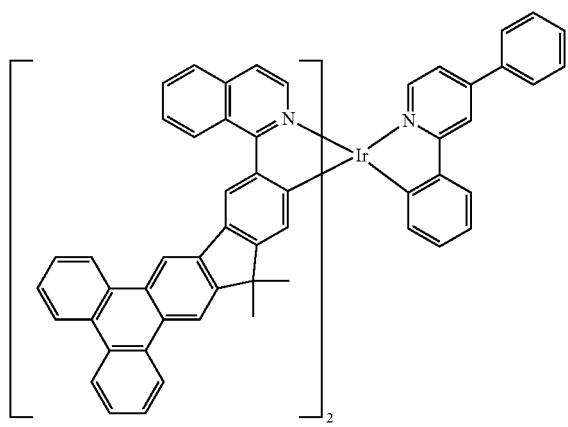
EX65
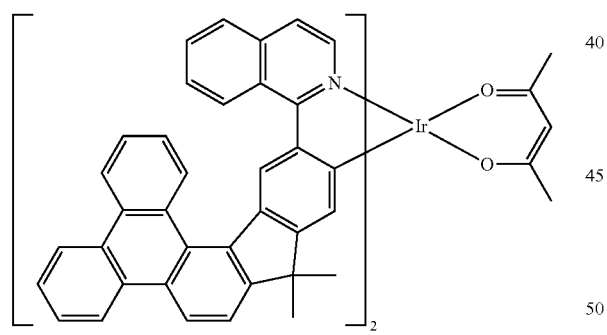
EX66
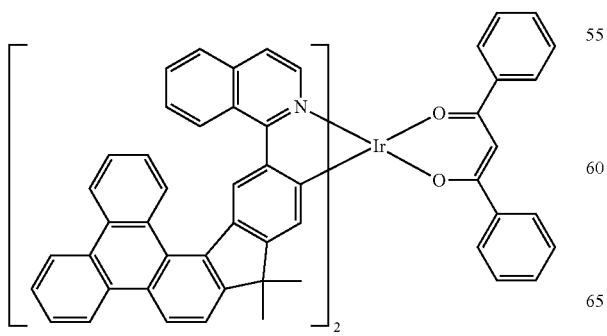
EX67
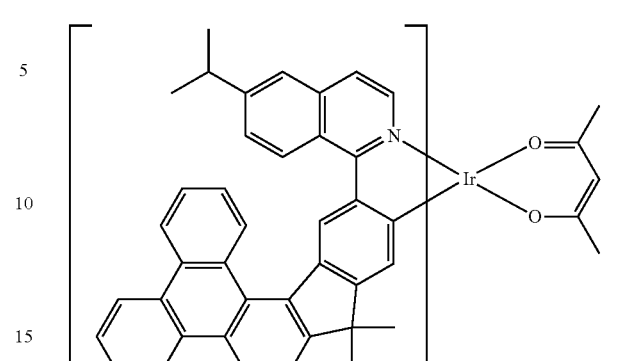
EX68
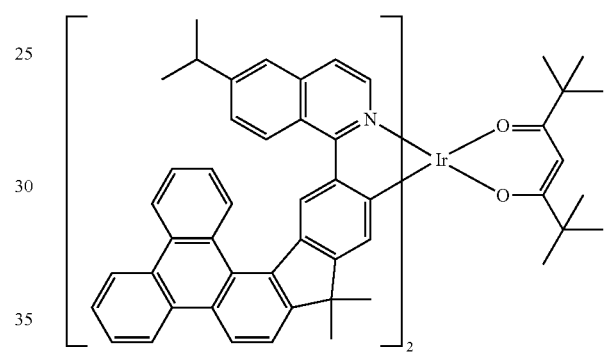
EX69
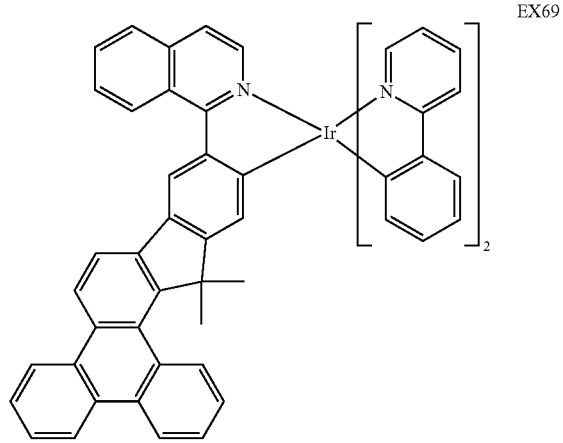

EX70
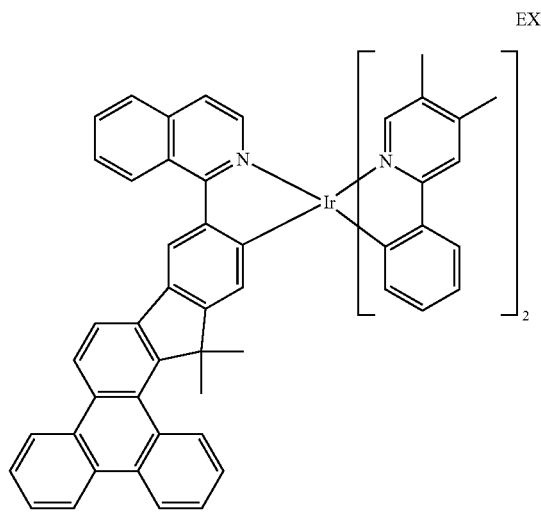
EX73
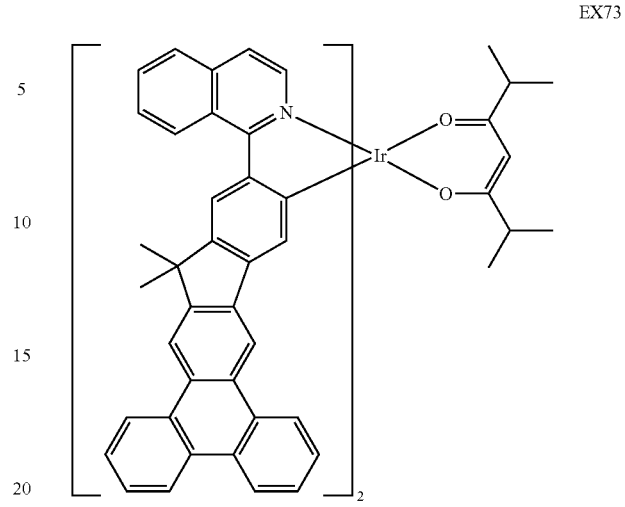
EX71
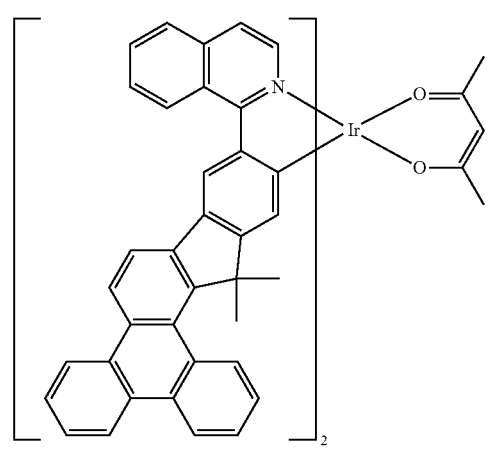
EX74
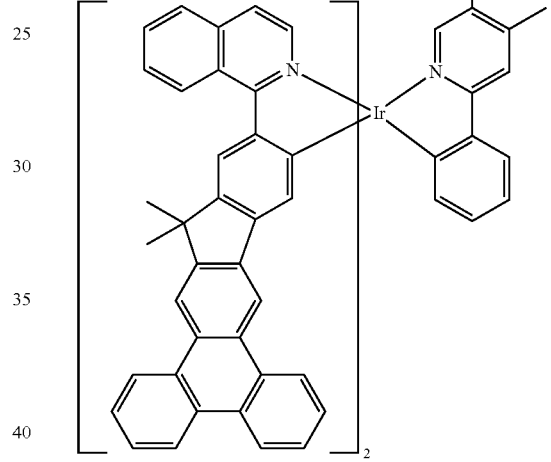
EX72
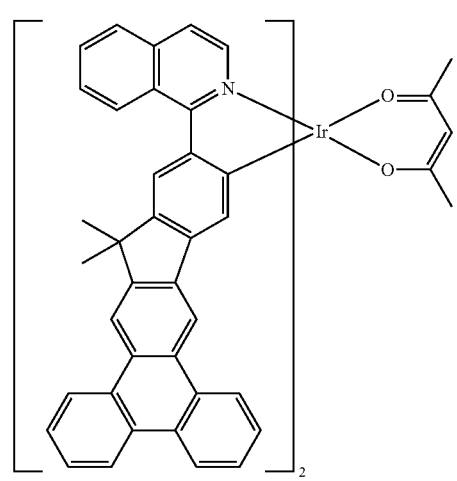
EX75
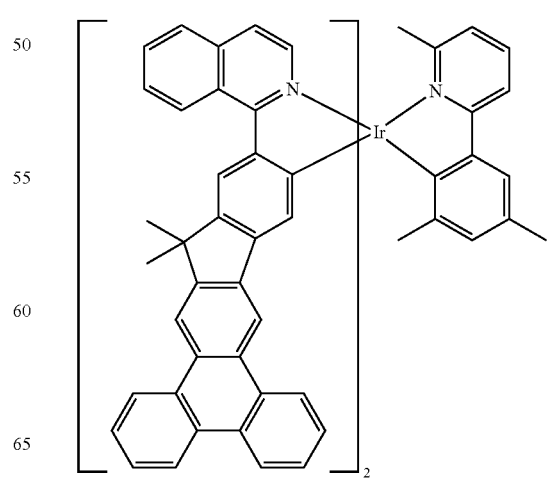

EX76
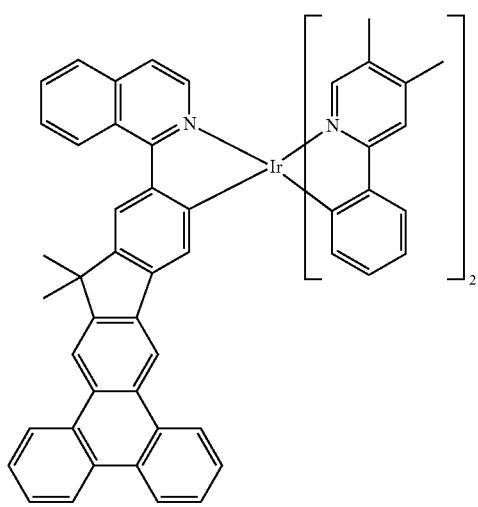
EX79
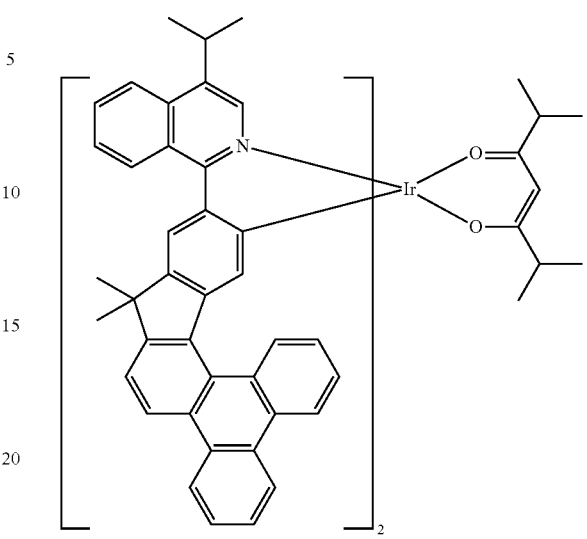
EX77
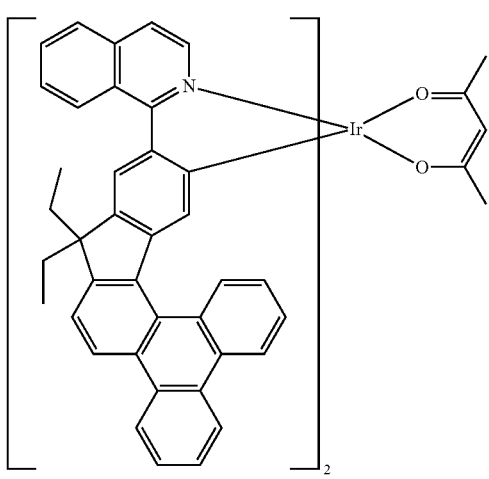
EX80
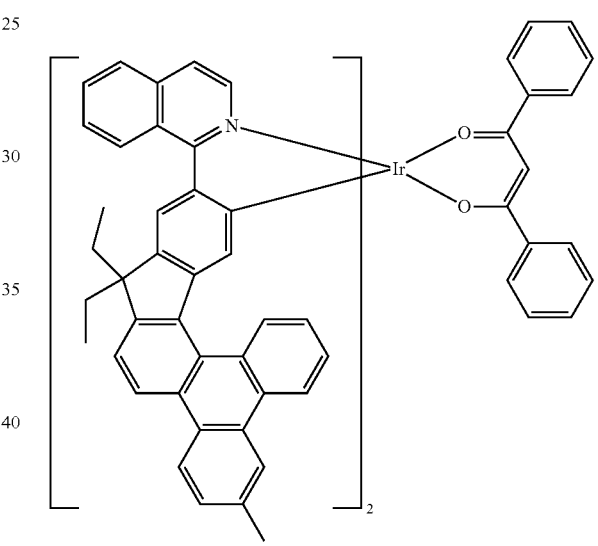
EX78
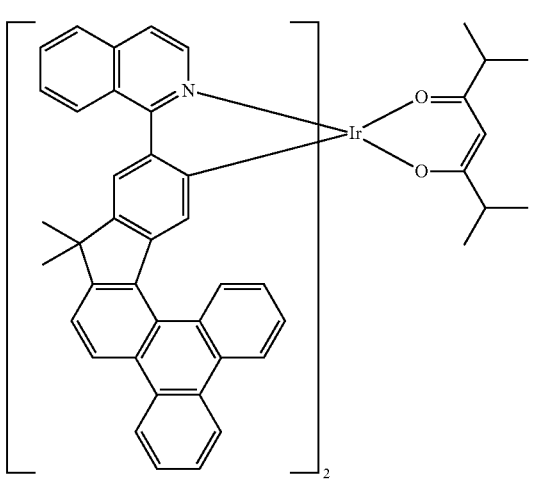
EX81
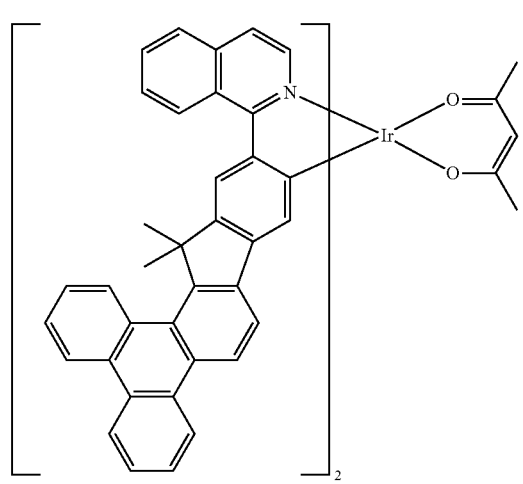

EX82
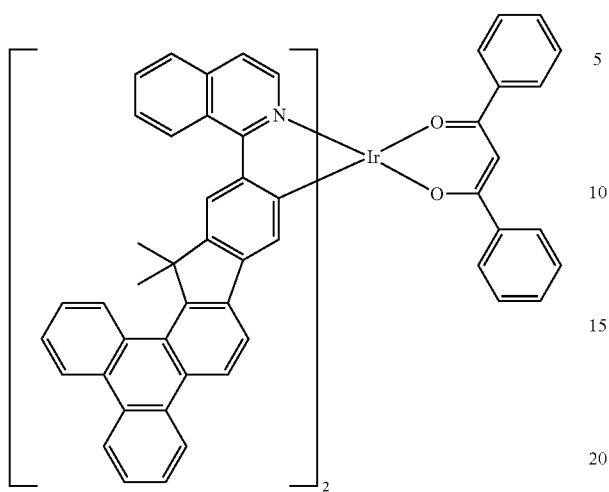
EX83
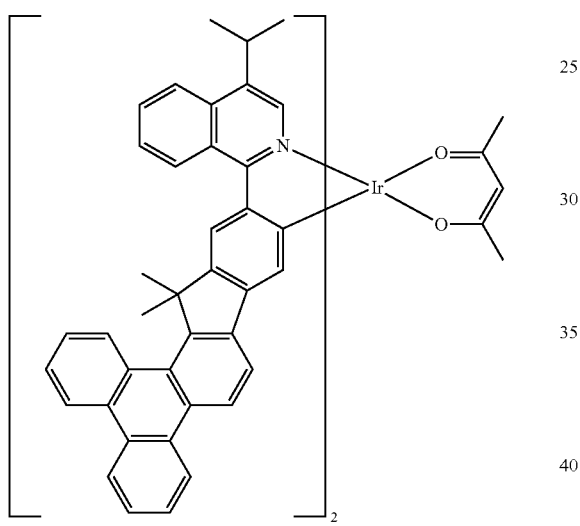
EX84
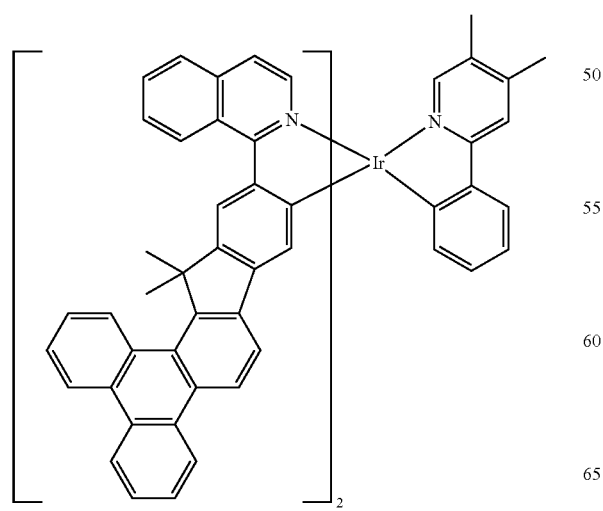
EX85
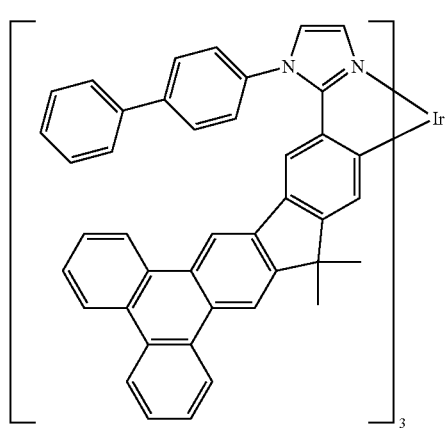
EX86
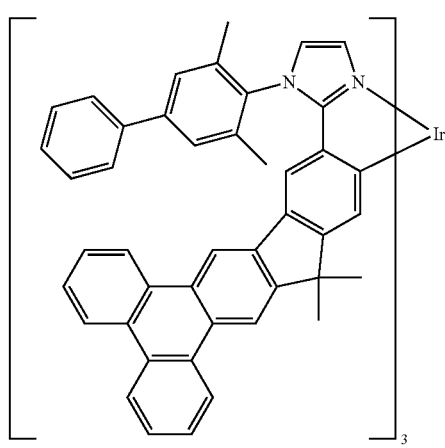
EX87
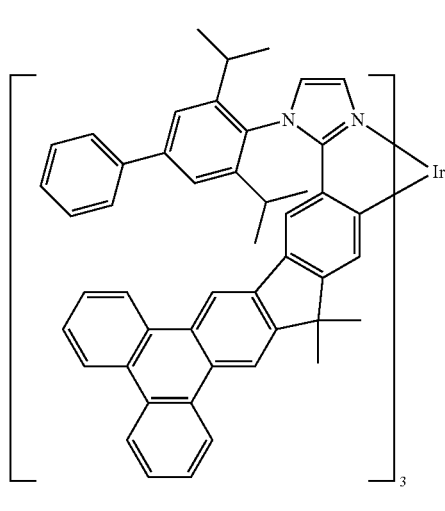

EX88
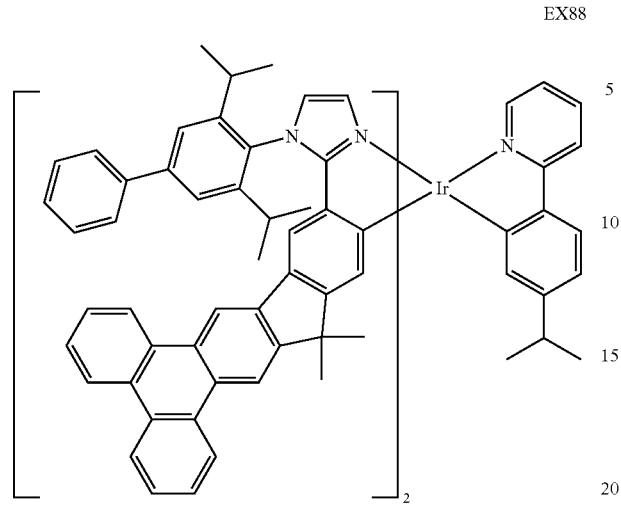
EX89
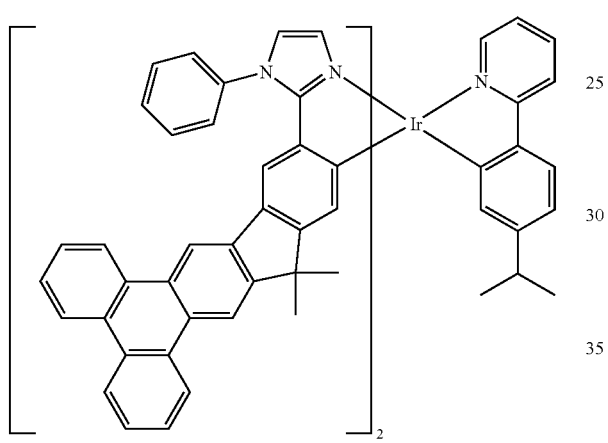
EX90
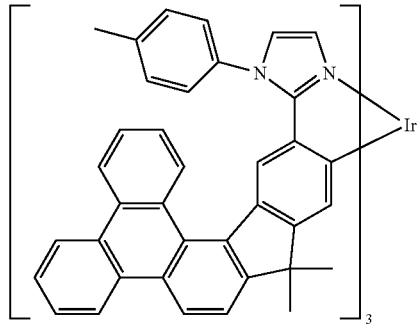
EX91
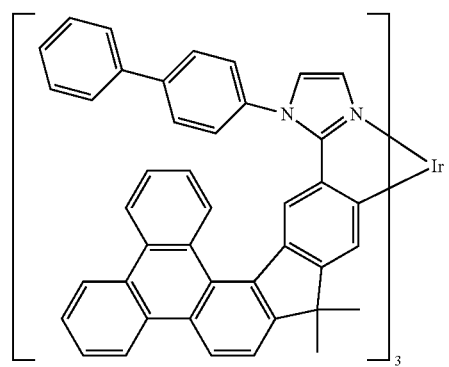
EX92
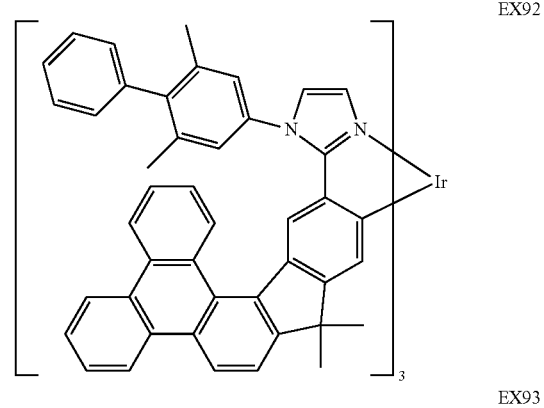
EX93
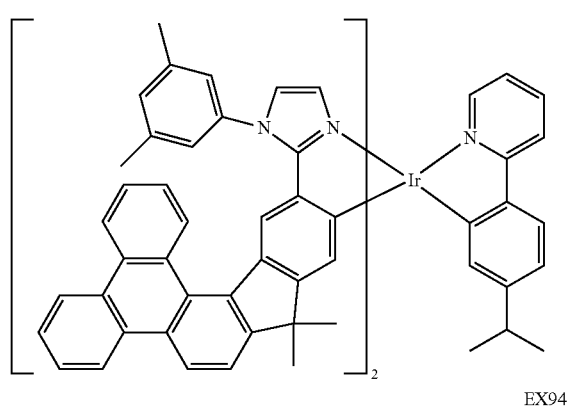
EX94
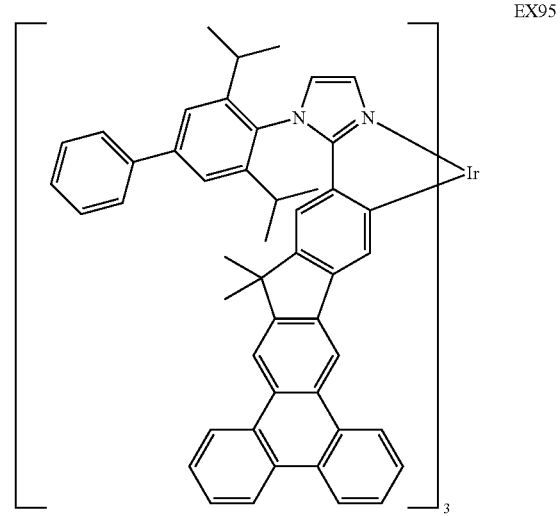
EX95

EX96
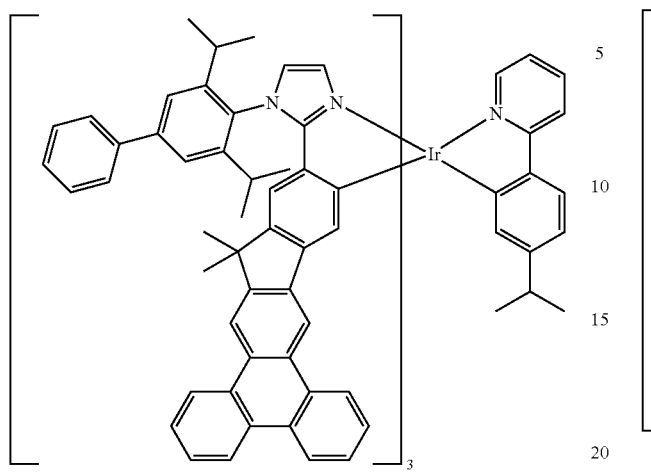
EX99
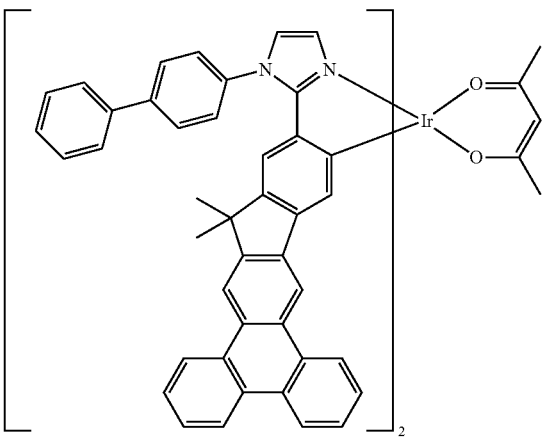
EX97
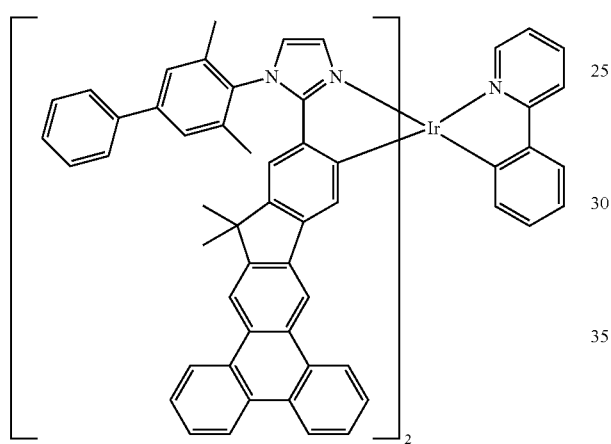
EX100
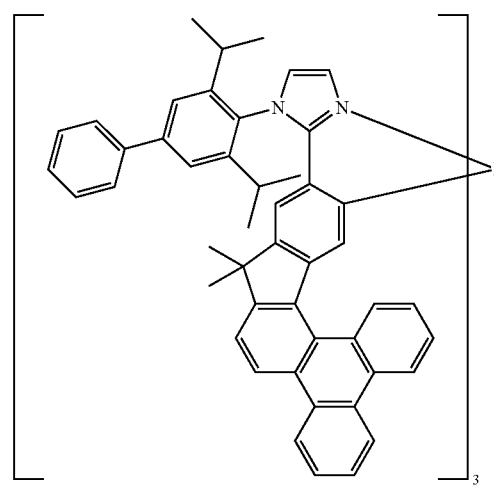
EX98
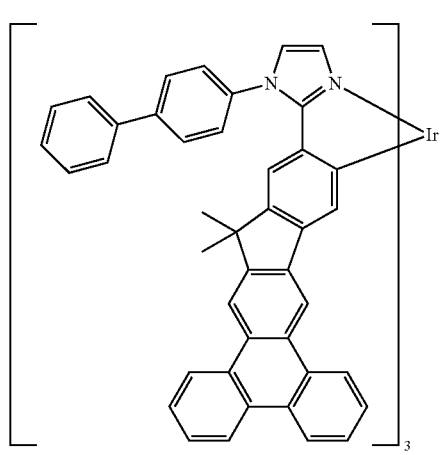
EX101
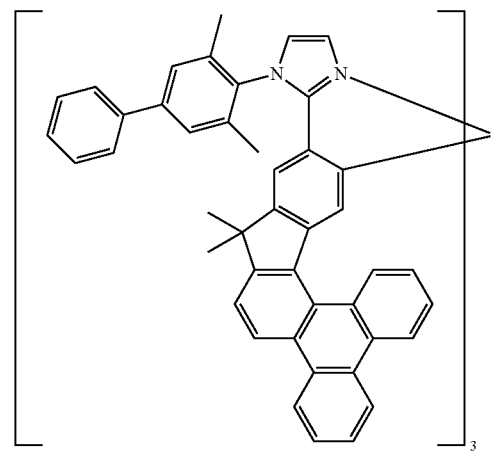

-continued
EX102
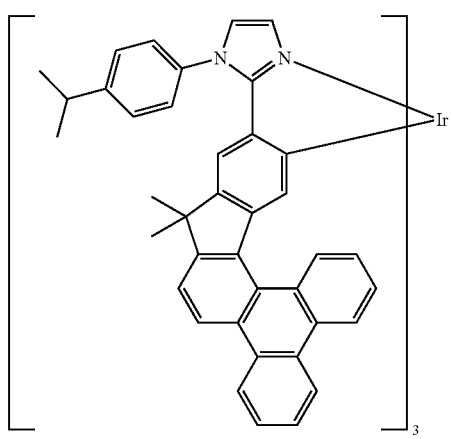
EX105
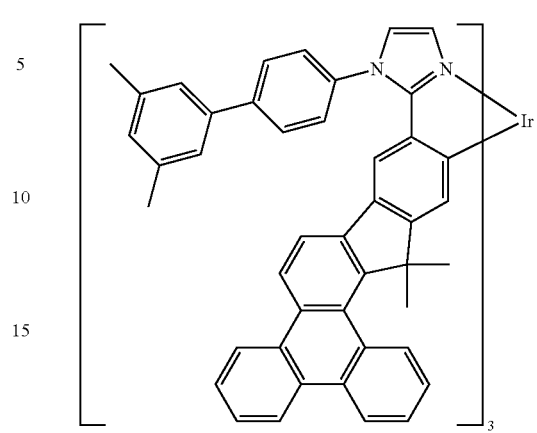
EX103
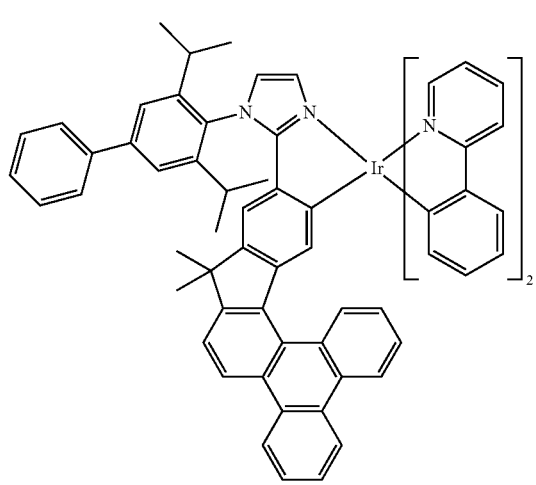
EX106
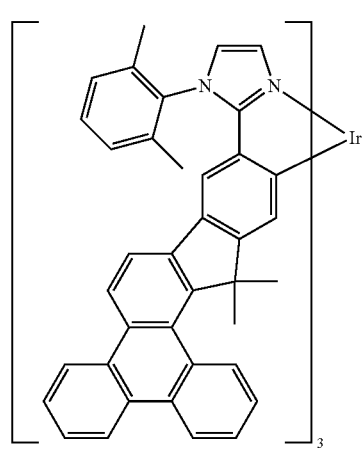
EX104
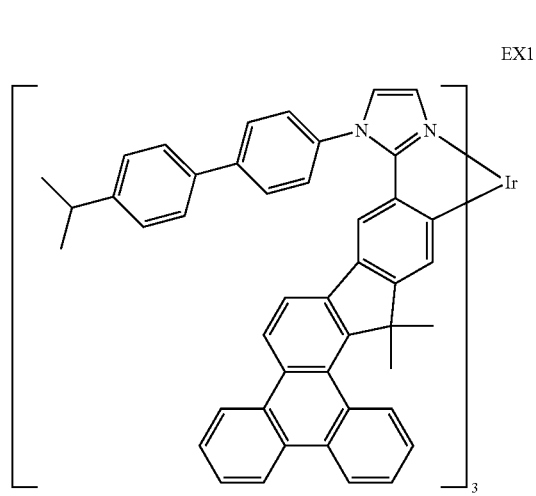
EX107
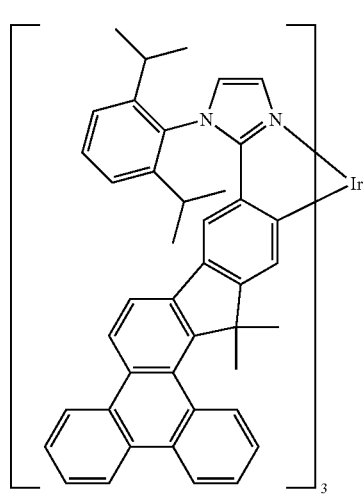

EX108
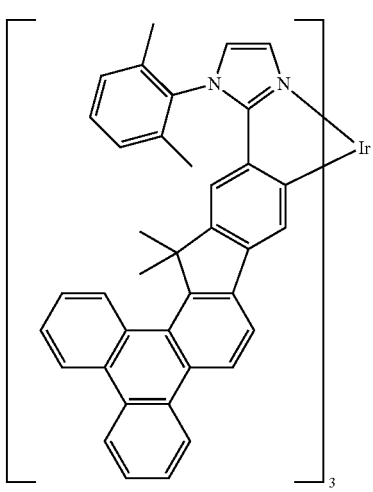
EX111
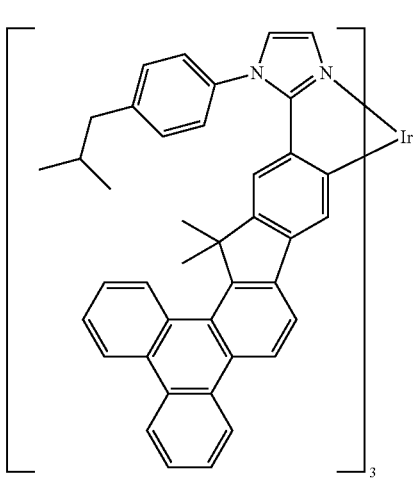
EX109
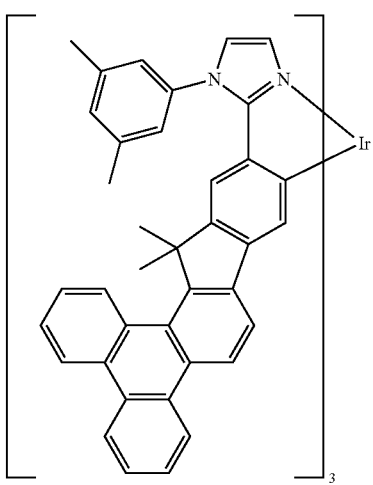
EX112
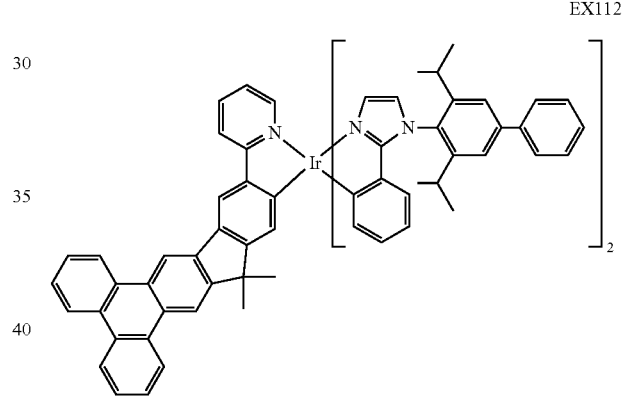
EX110
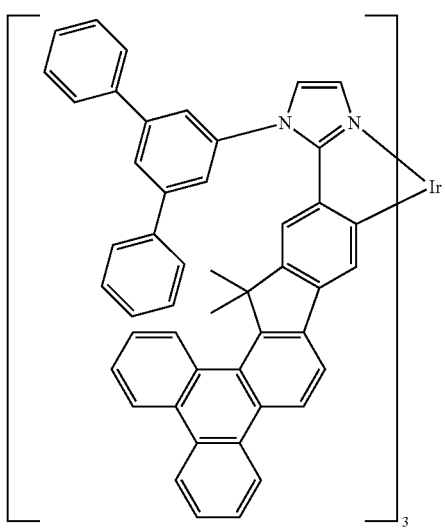
EX113
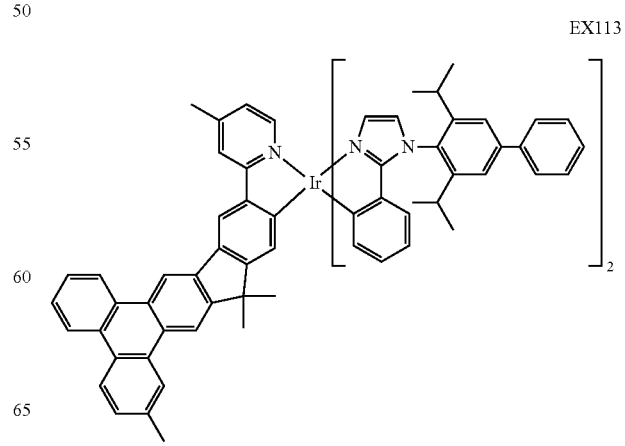

EX114
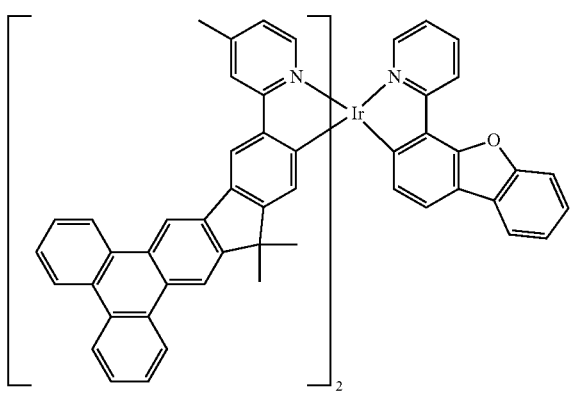
EX115
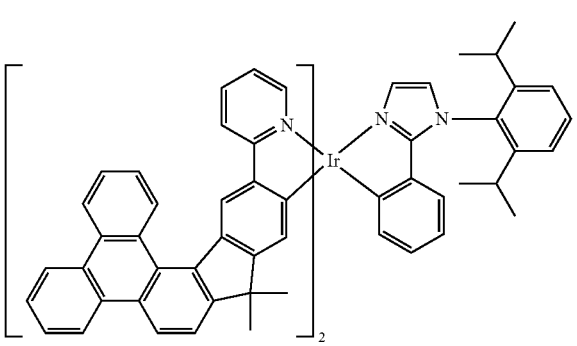
EX116
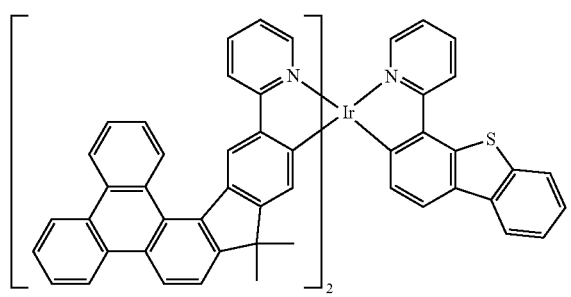
EX117
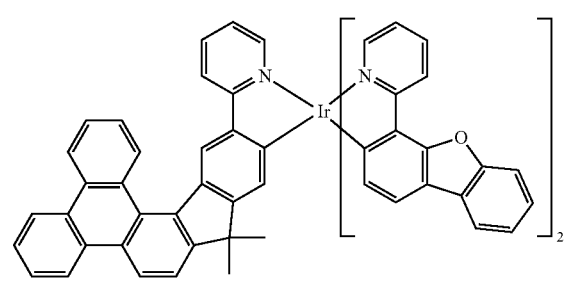
EX118
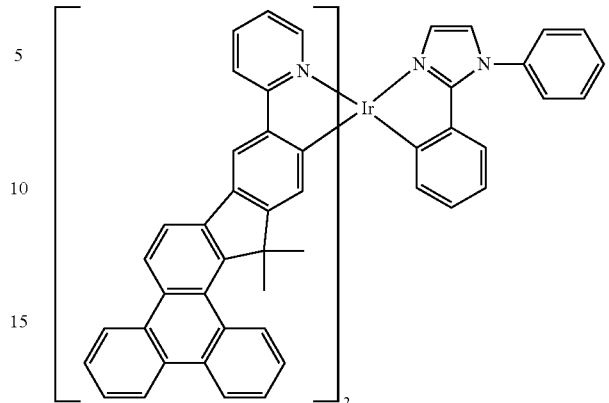
EX119
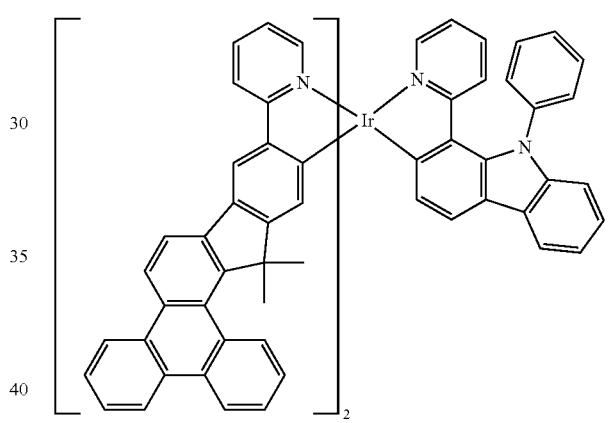
EX120
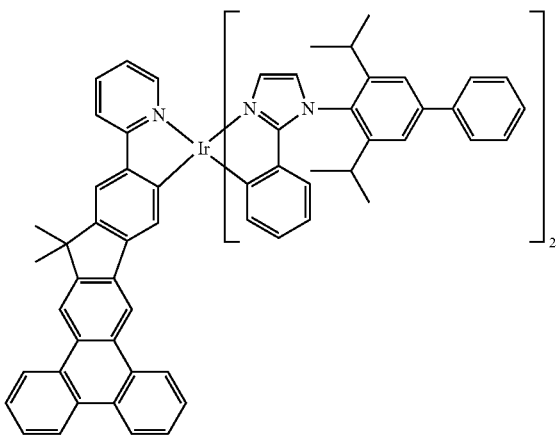

EX121
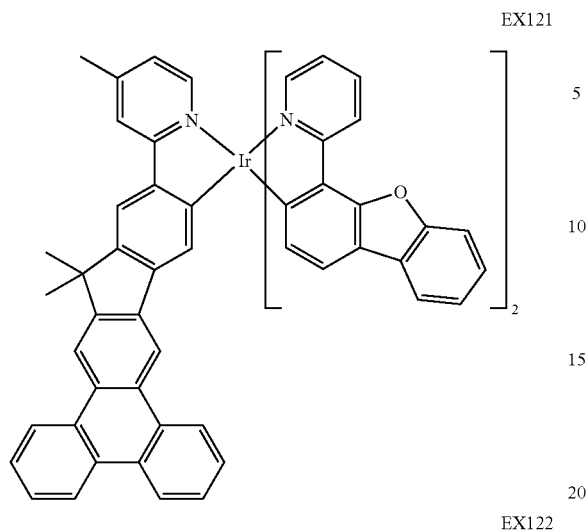
EX122
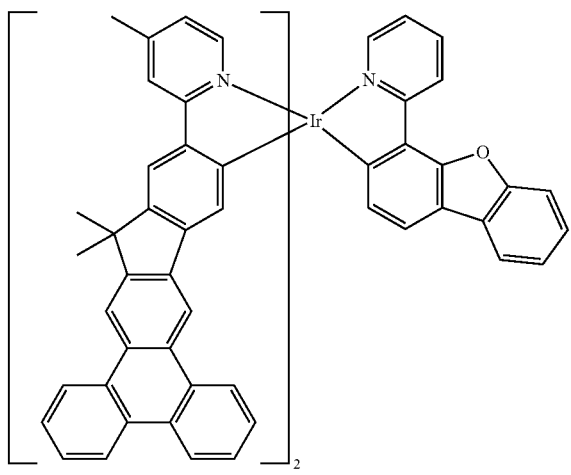
EX123
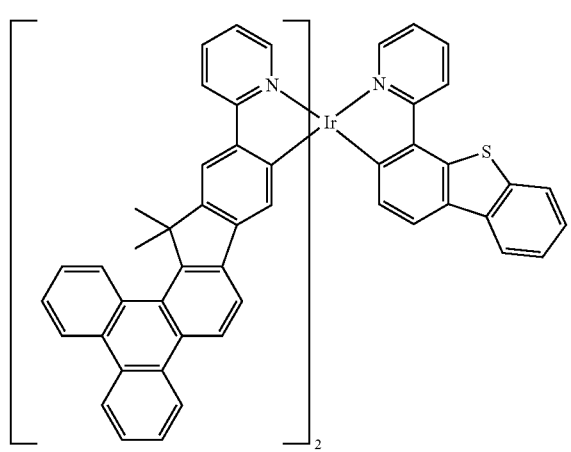
EX124
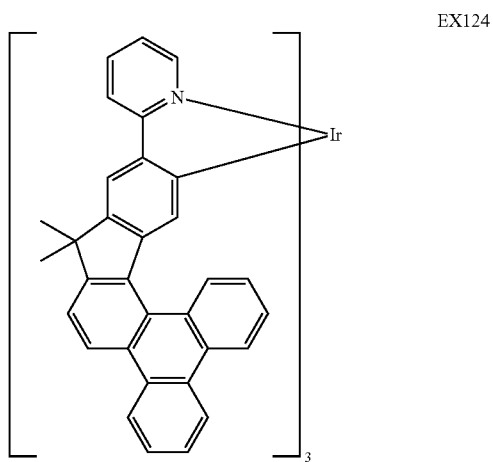
EX125
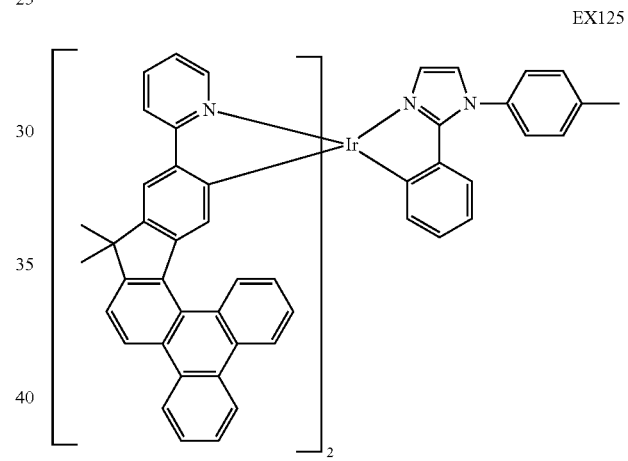
EX126
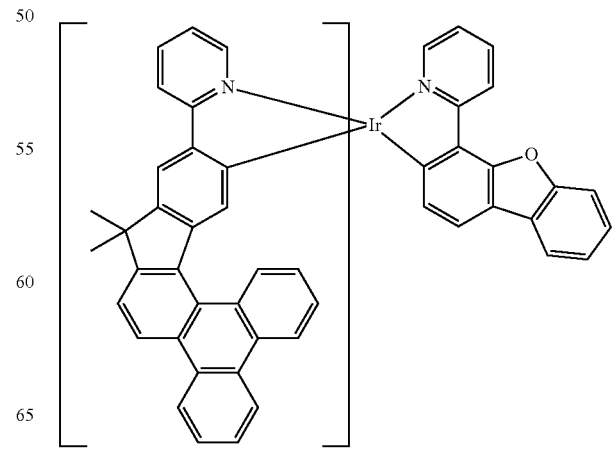

-continued
EX127
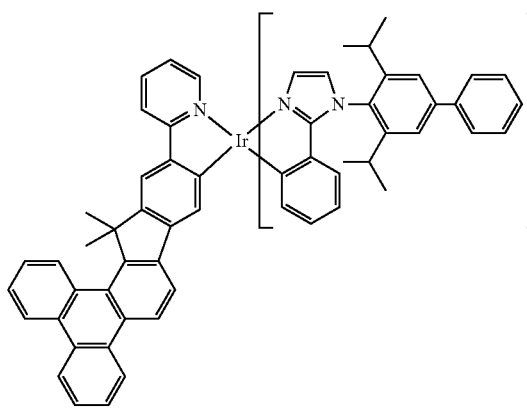
EX128
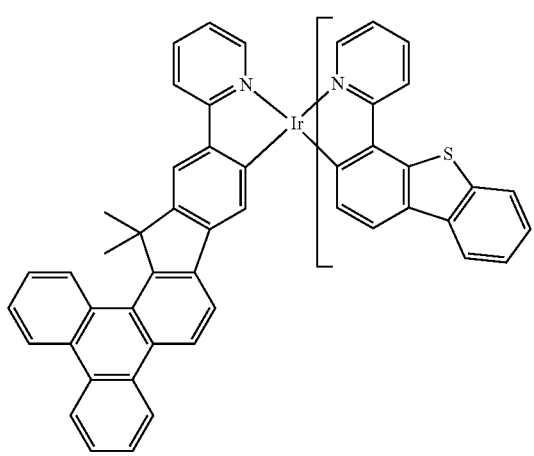
EX129
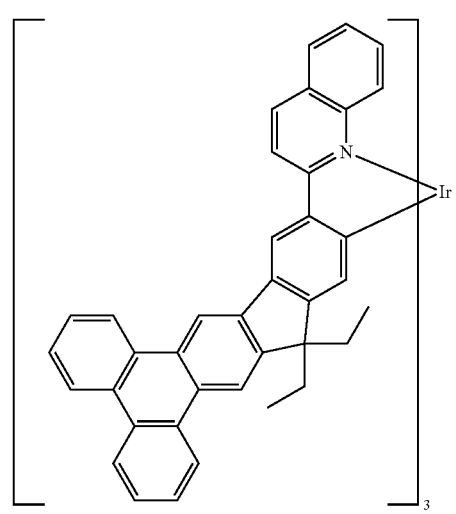
-continued
EX130
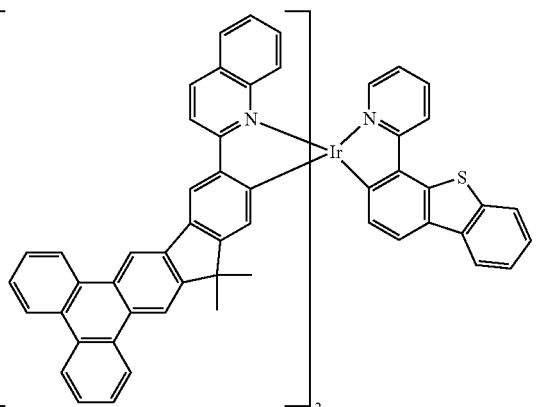
EX131
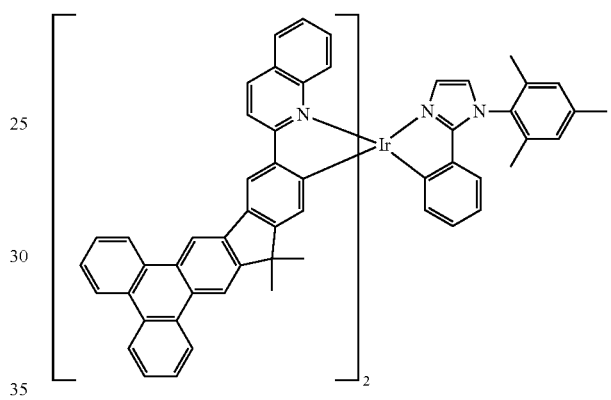
EX132
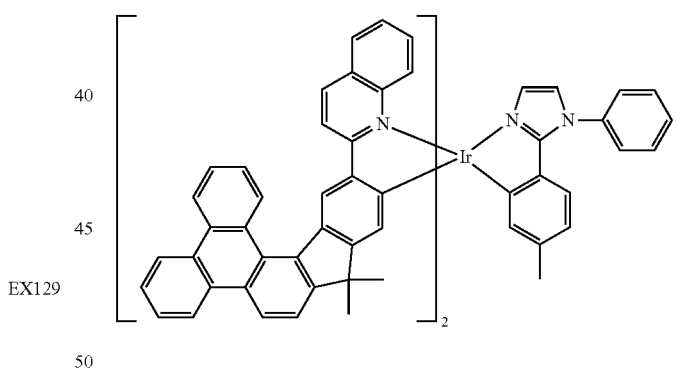
EX133
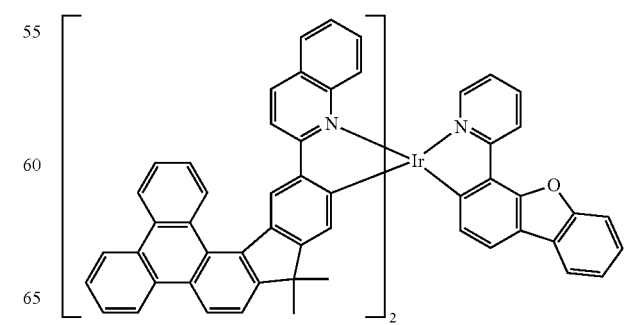

EX134
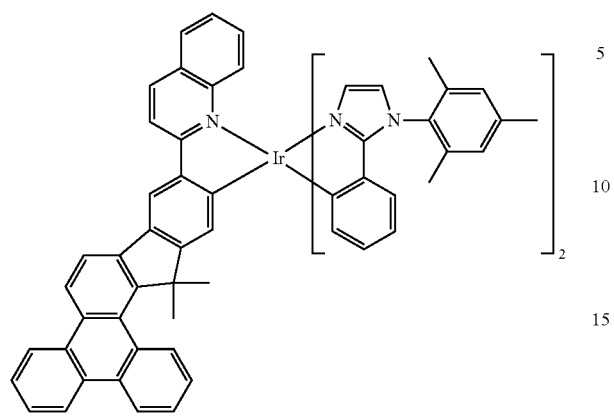
EX135
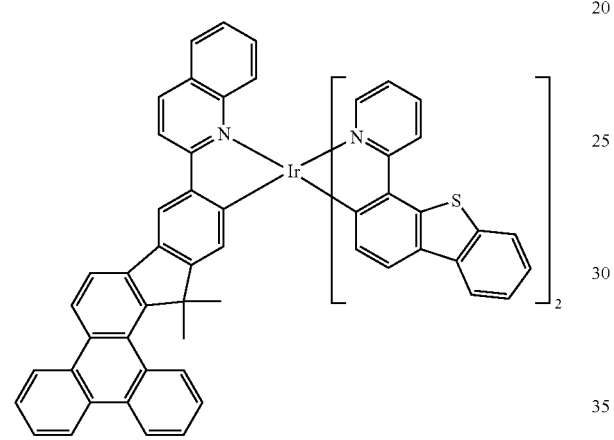
EX136
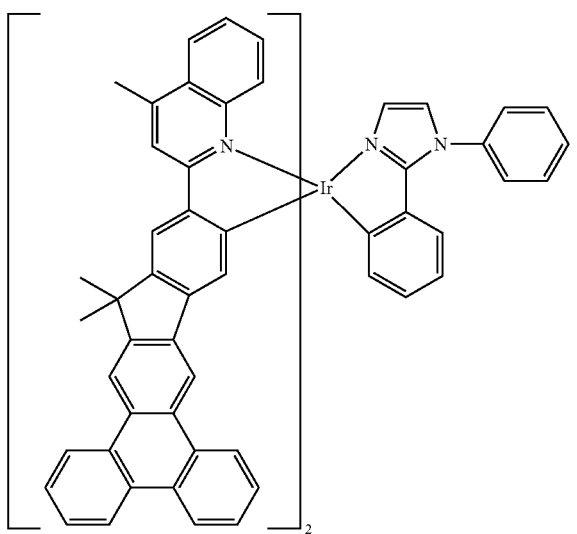
EX137
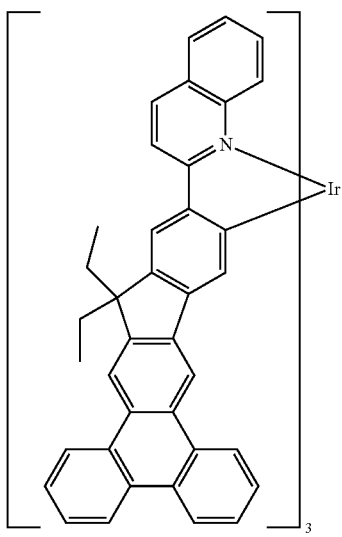
EX138
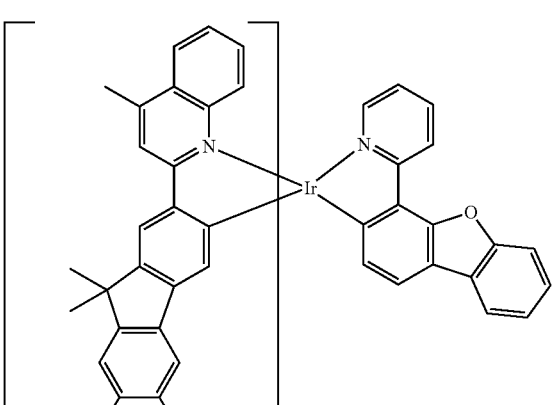
EX139
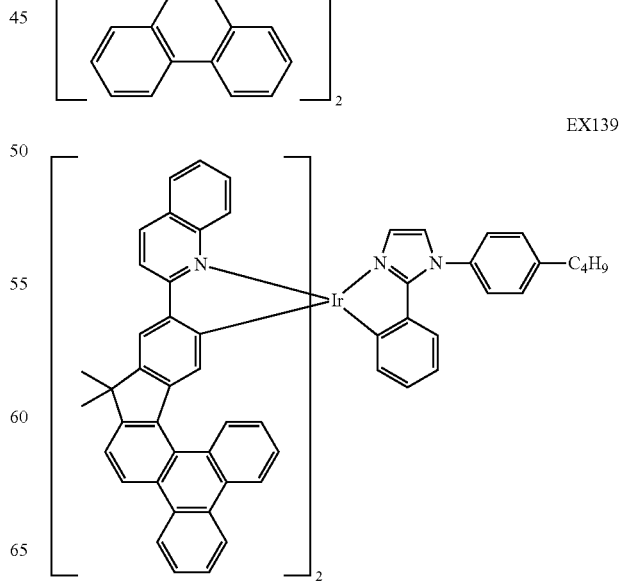

-continued
EX140
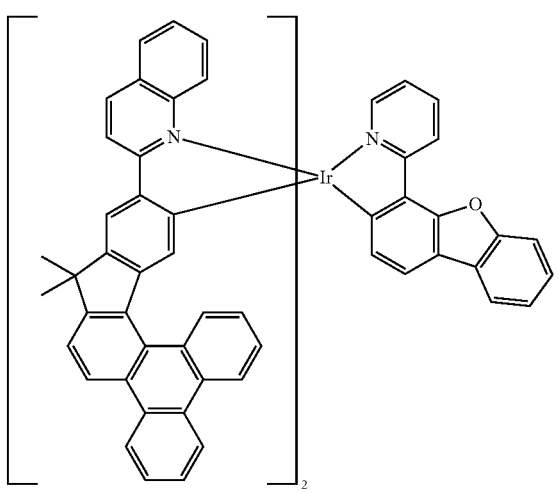
EX141
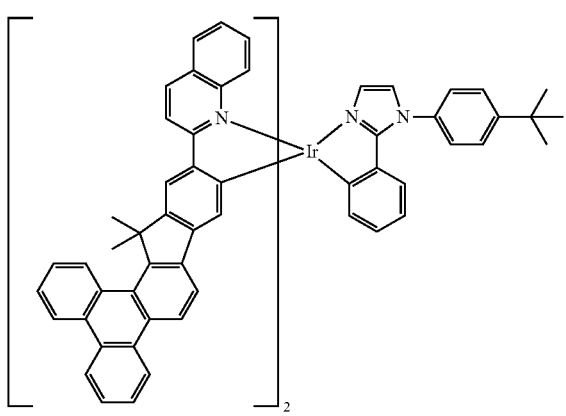
EX142
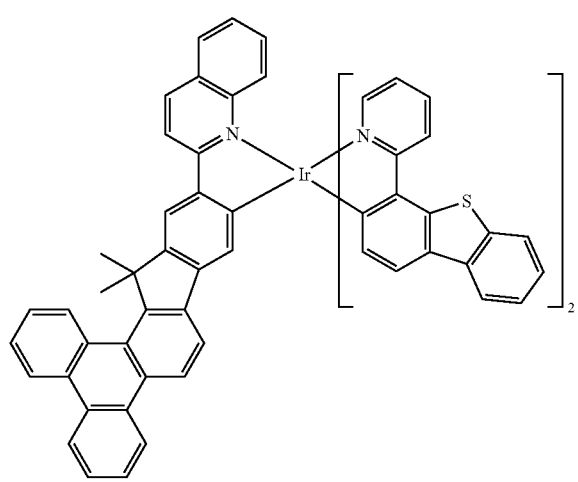
-continued
EX143
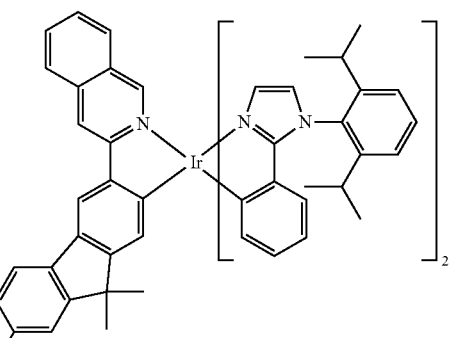
EX144
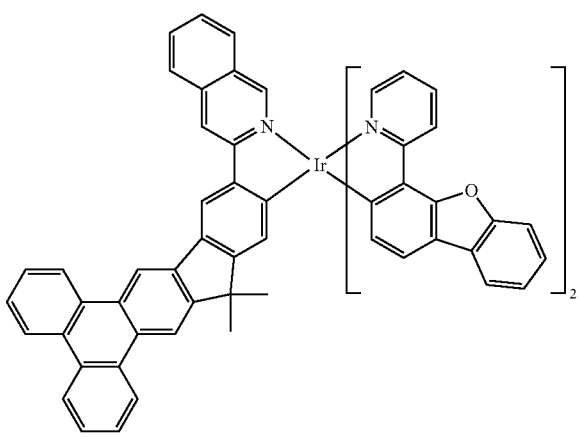
EX145
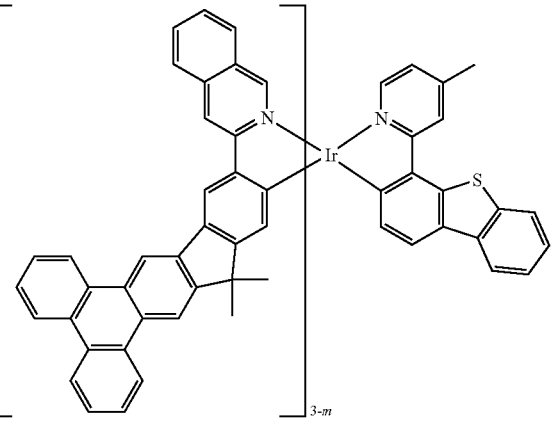

EX146
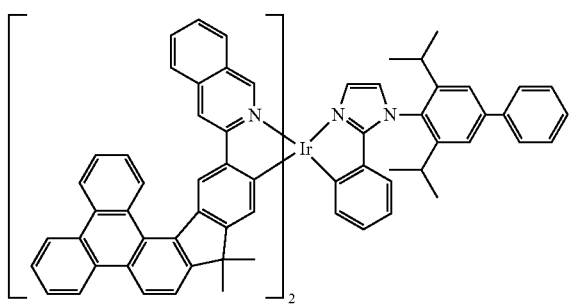
EX147
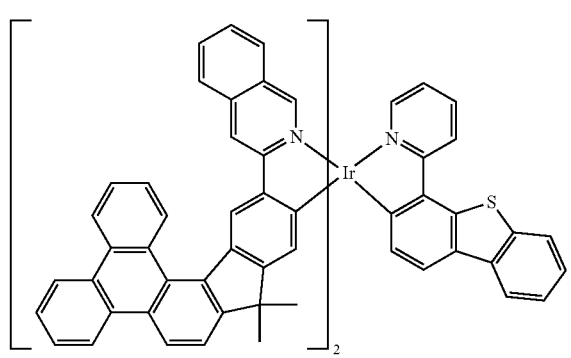
EX148
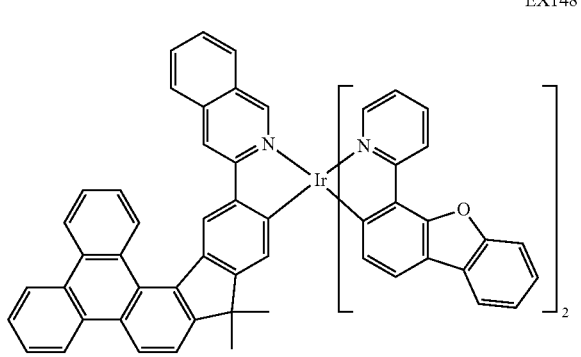
EX149
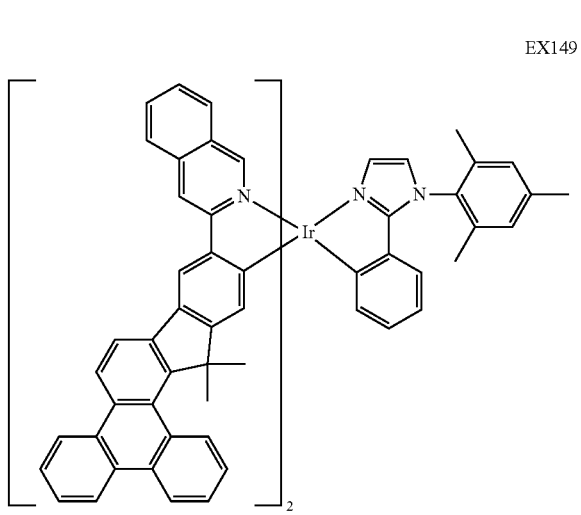
EX150
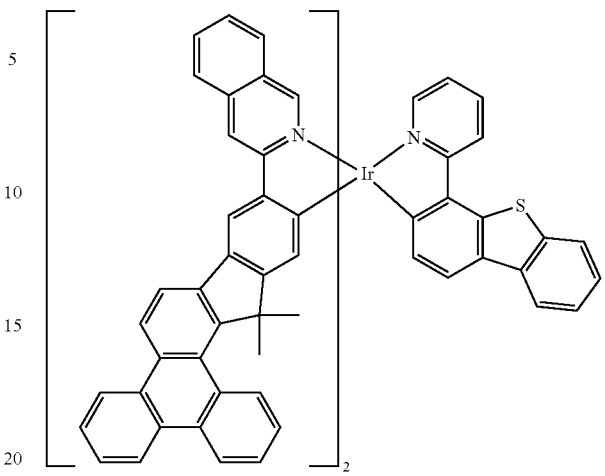
EX151
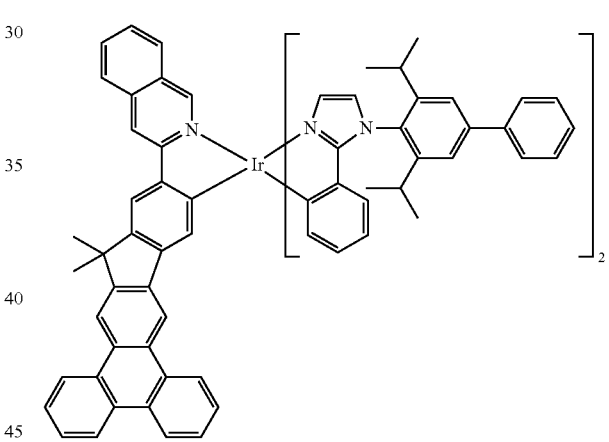
EX152
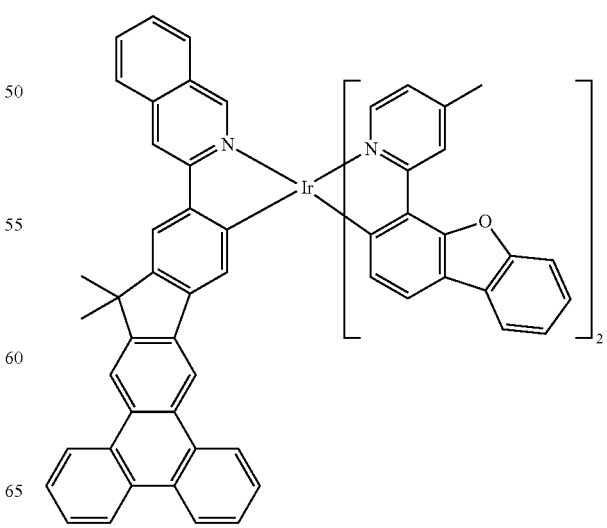

-continued
EX153
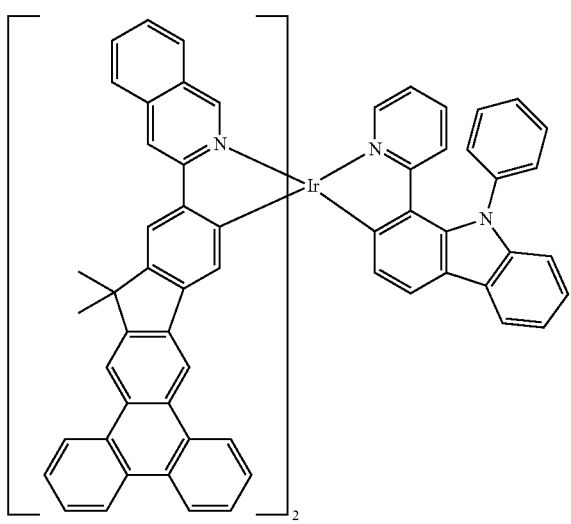
EX154
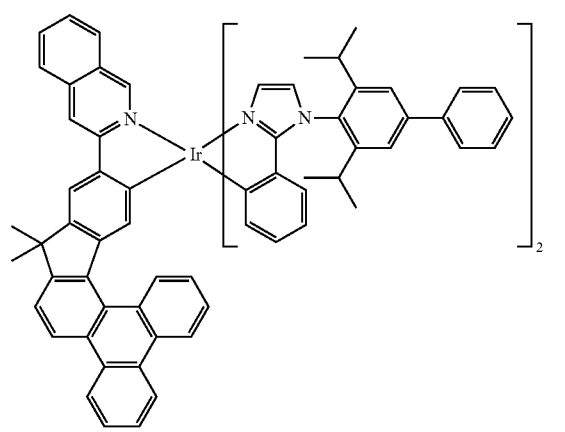
EX155
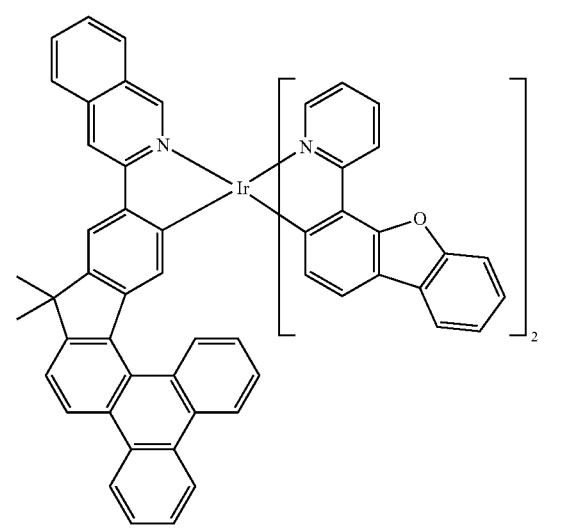
-continued
EX156
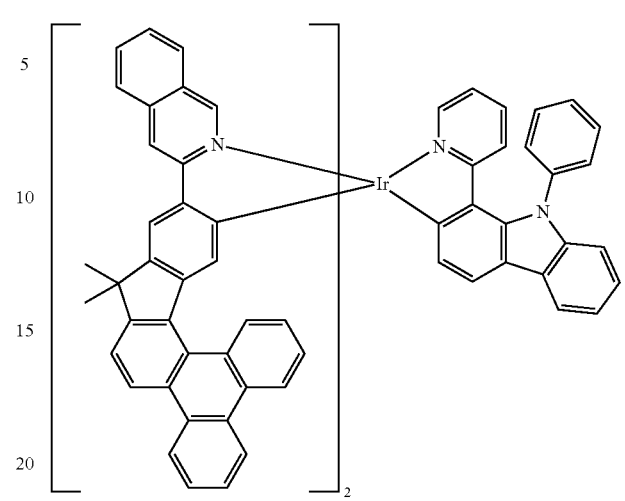
EX157
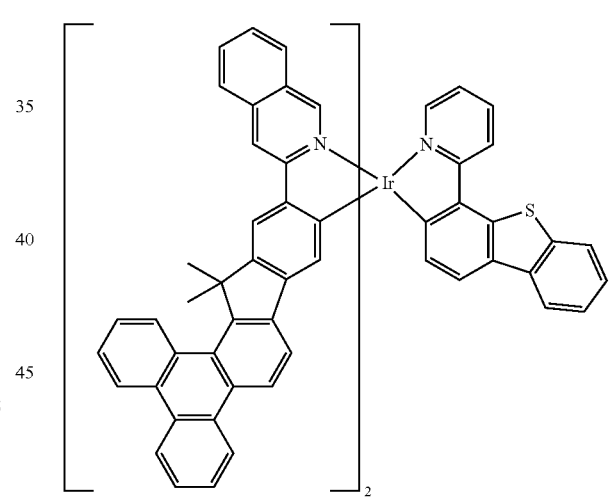
EX158
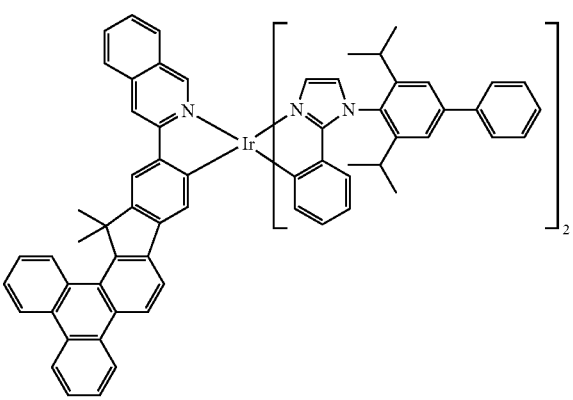

EX159
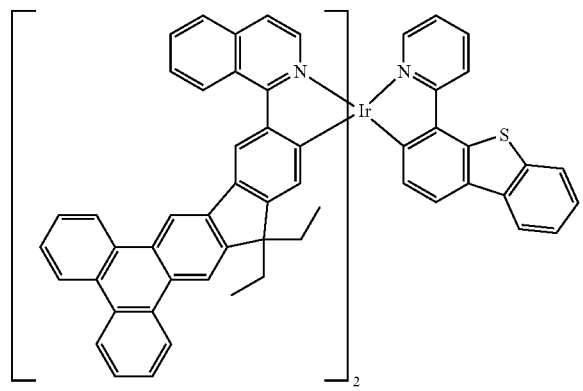
EX163
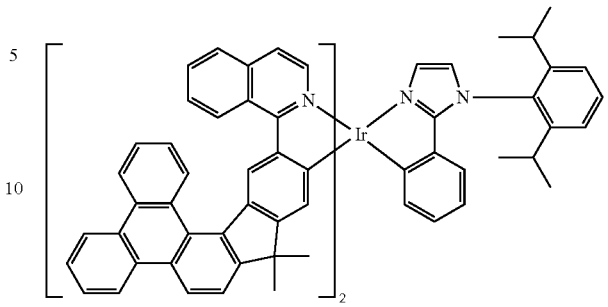
EX160
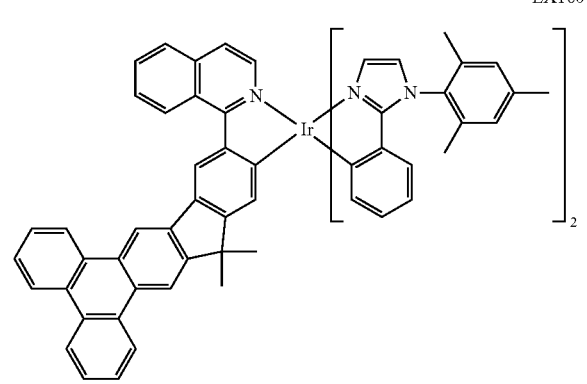
EX164
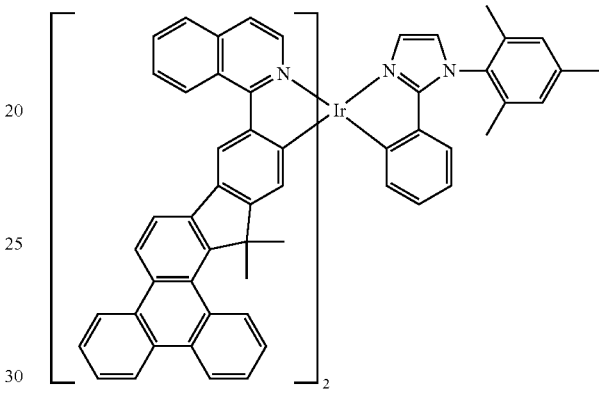
EX161
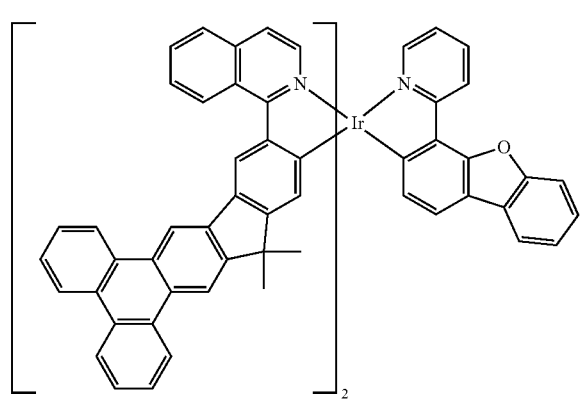
EX165
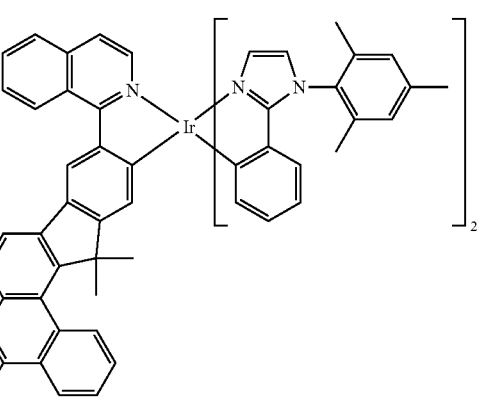
EX162
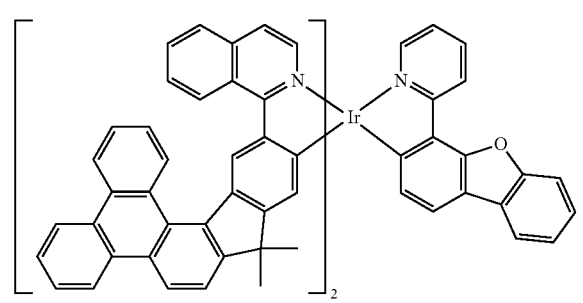
EX166
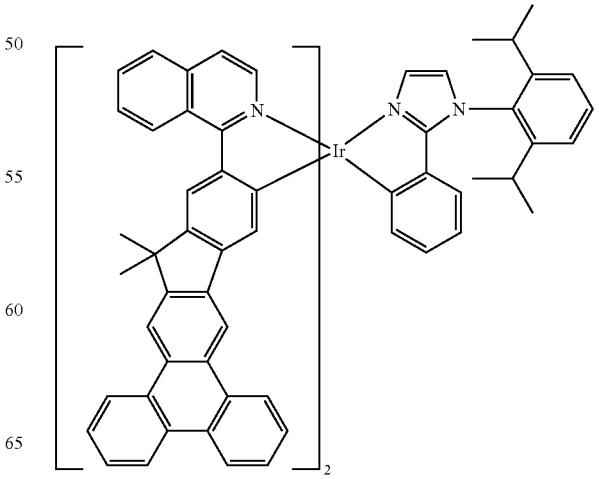

EX167
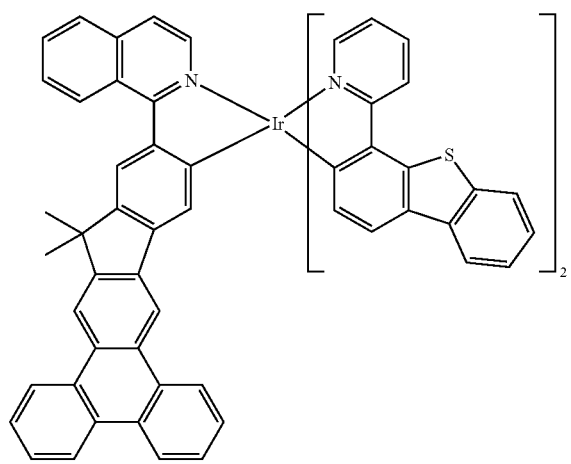
EX168
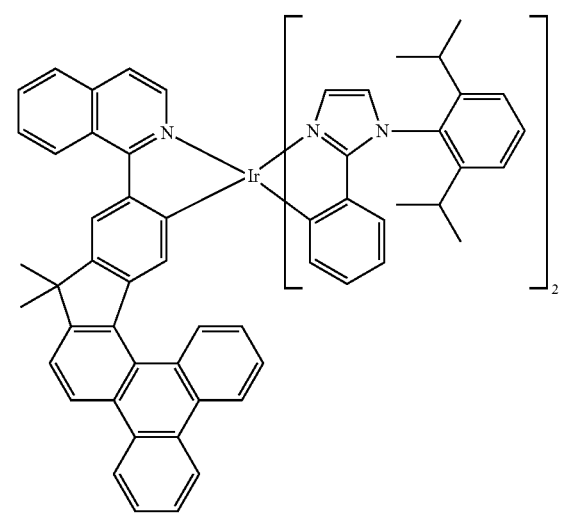
EX169
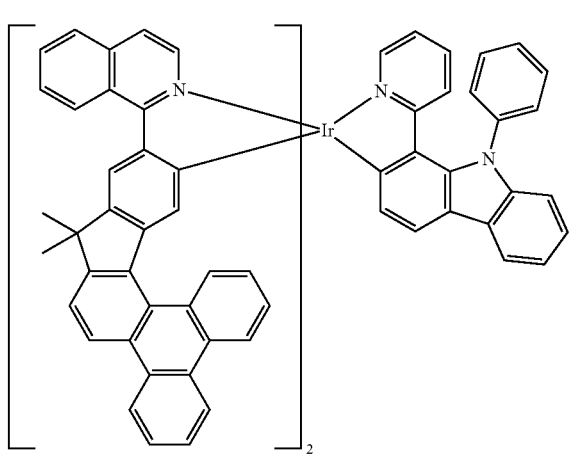
EX170
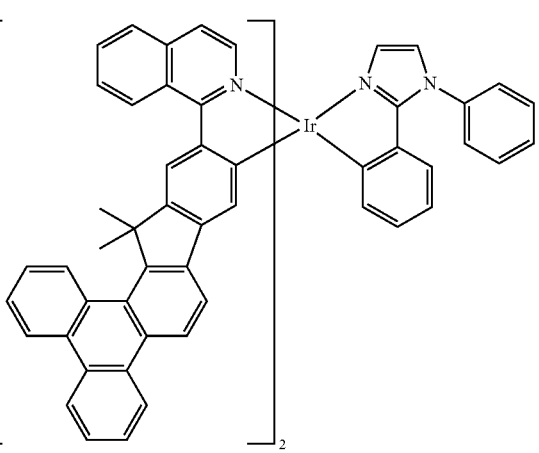
EX171
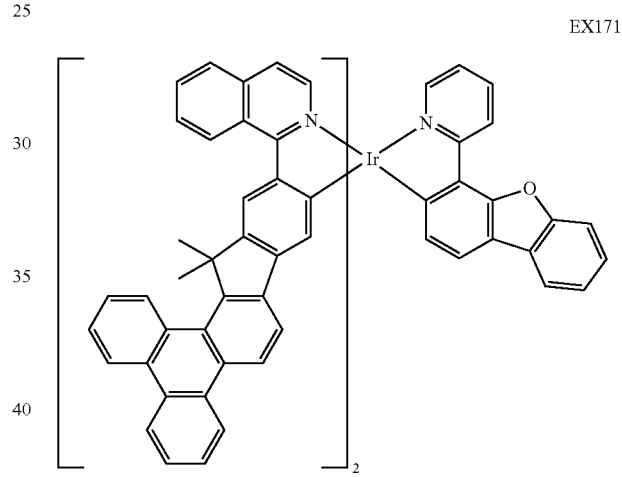
EX172
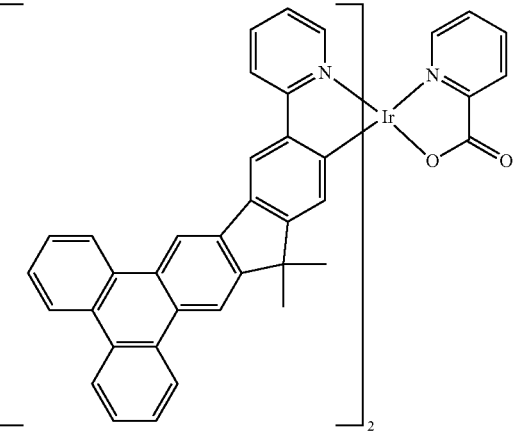

-continued
EX173
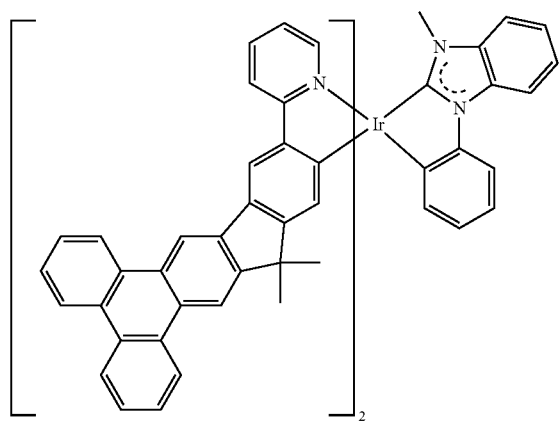
EX174
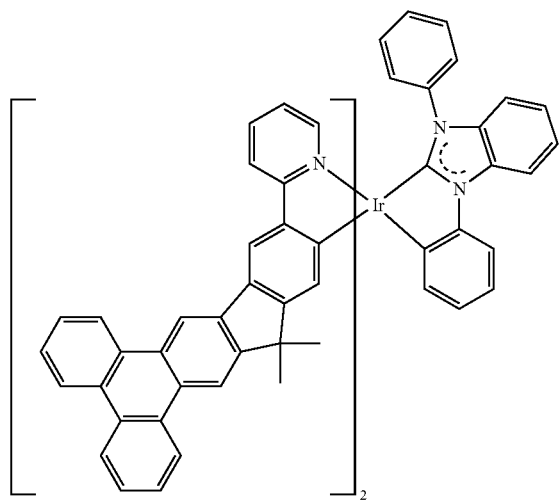
EX175
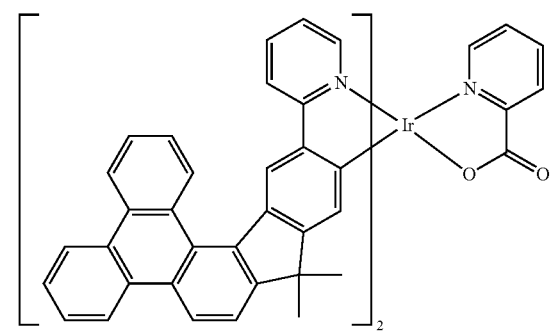
-continued
EX176
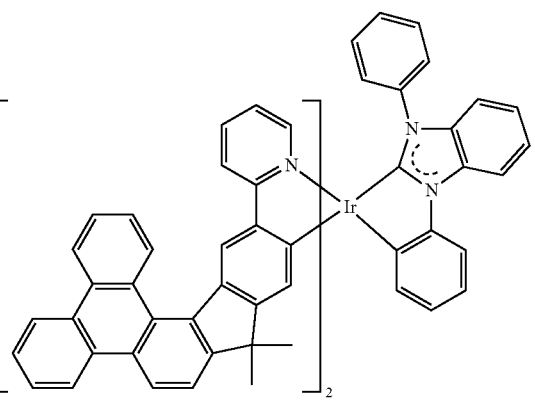
EX177
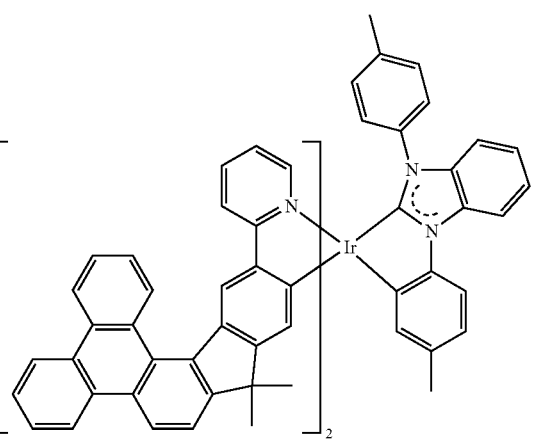
EX178
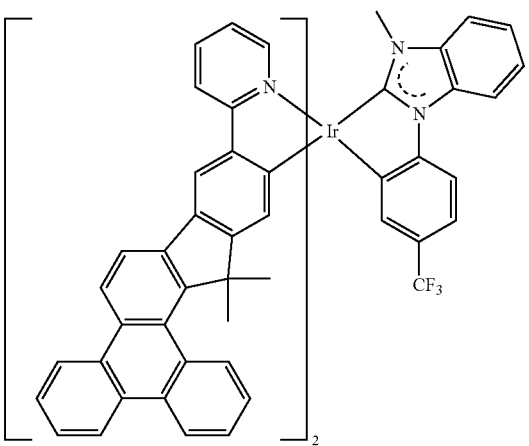

75
-continued
EX179
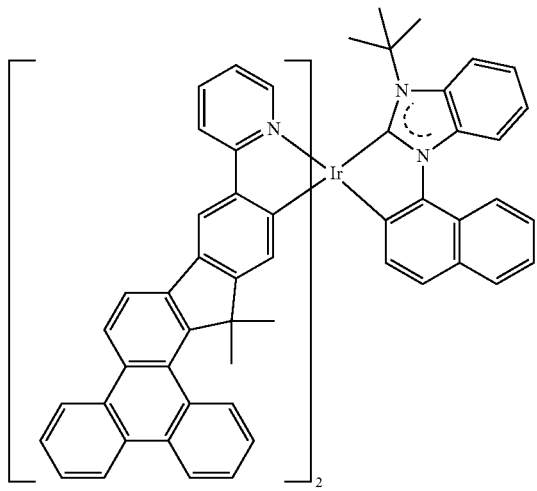
EX180
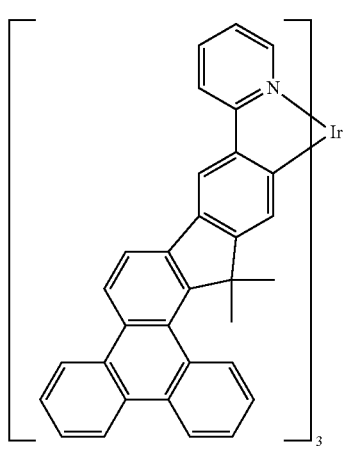
EX181
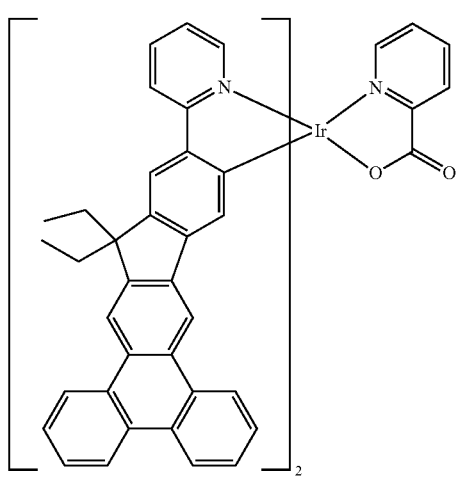
76
-continued
EX182
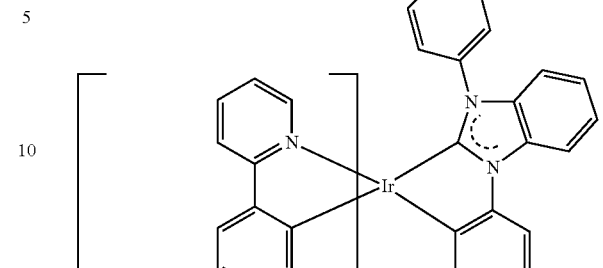
EX183
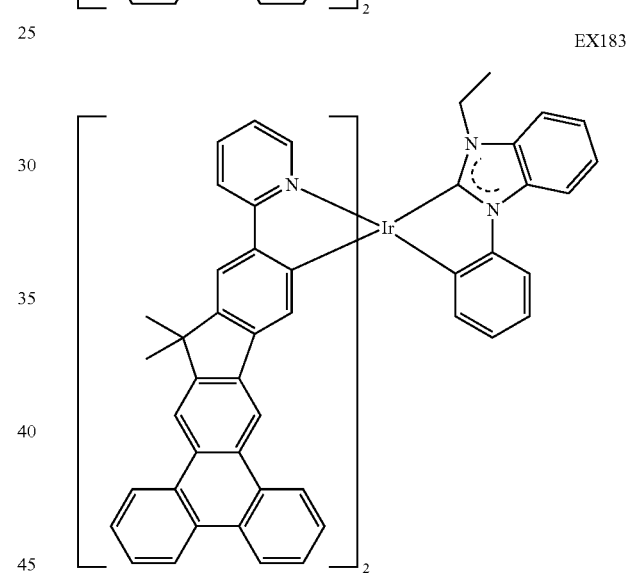
EX184
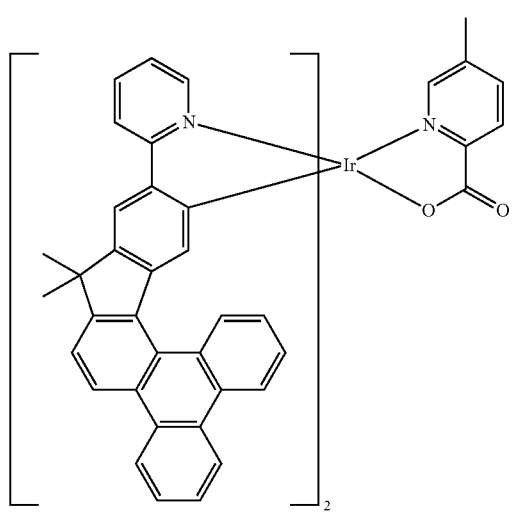

-continued
EX185
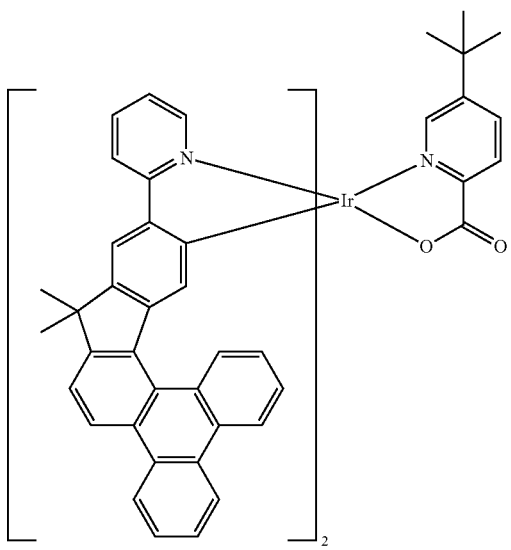
EX186
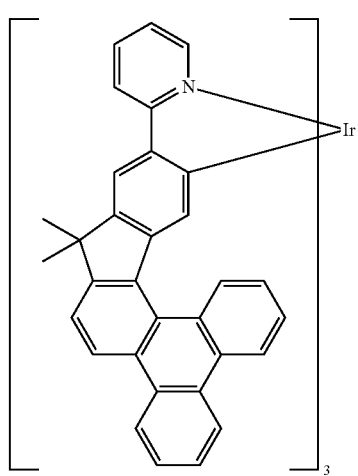
EX187
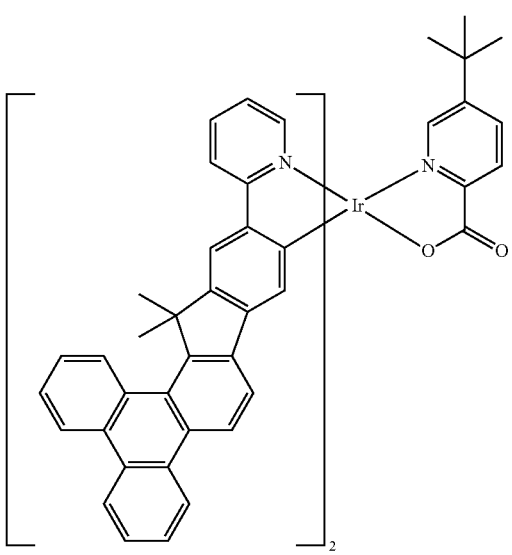
-continued
EX188
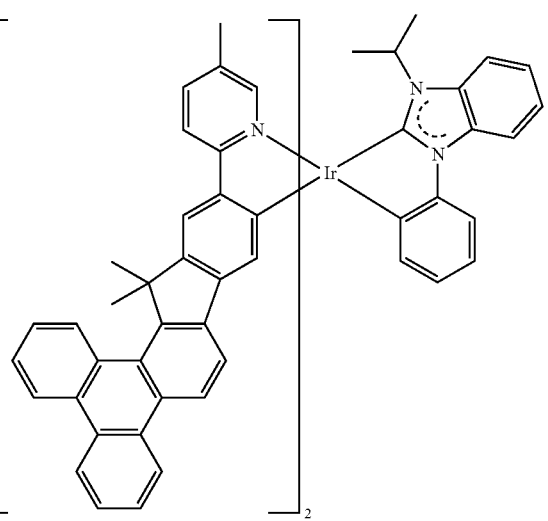
EX189
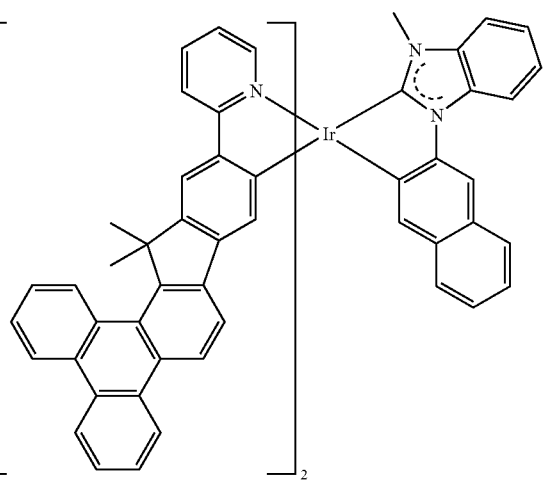
EX190
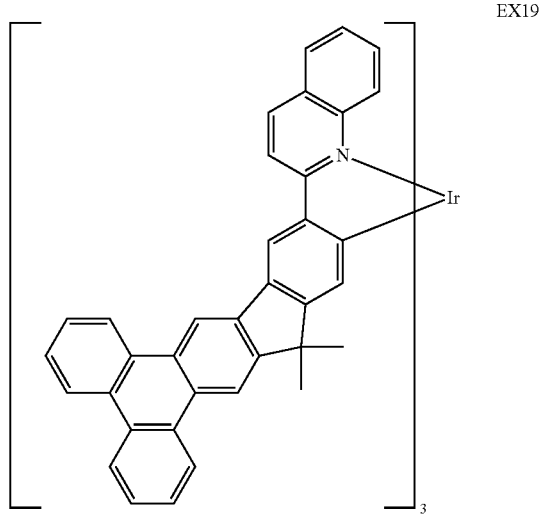

EX191
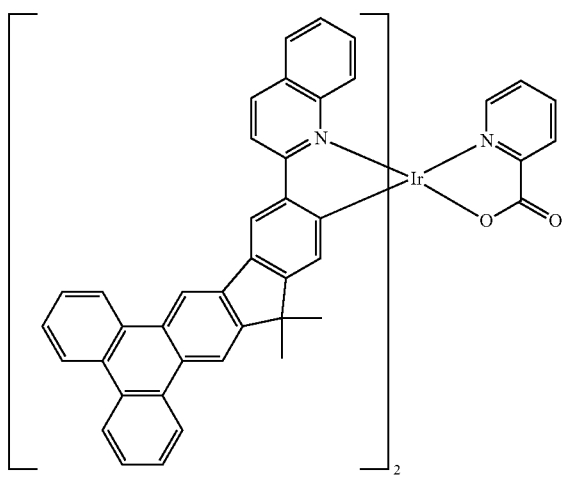
EX194
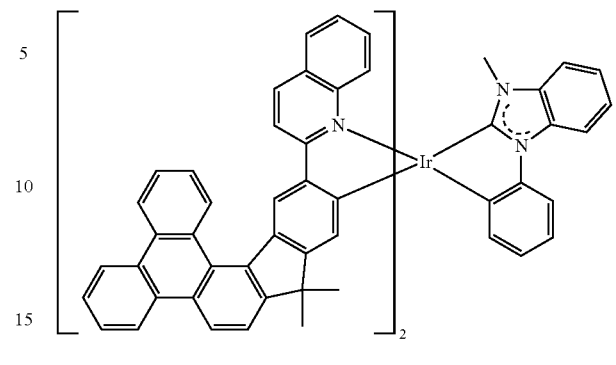
EX192
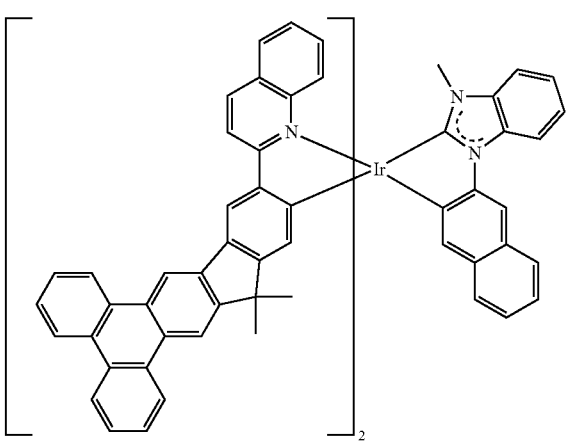
EX195
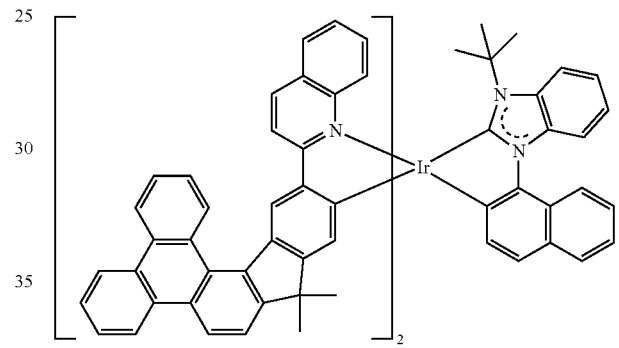
EX193
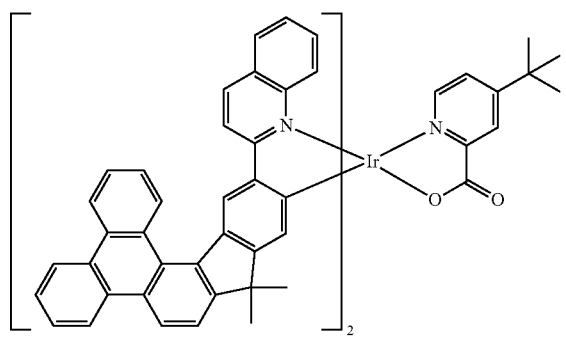
EX196
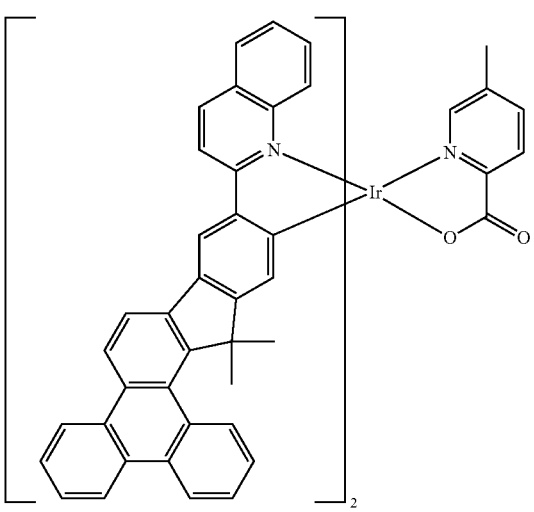

EX197
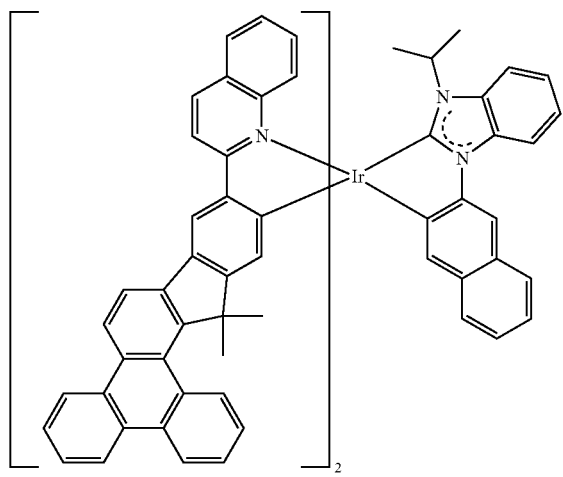
EX198
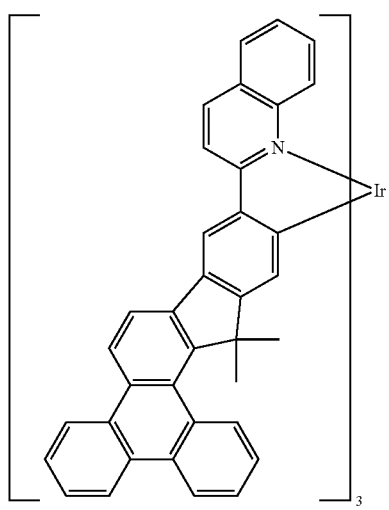
EX199
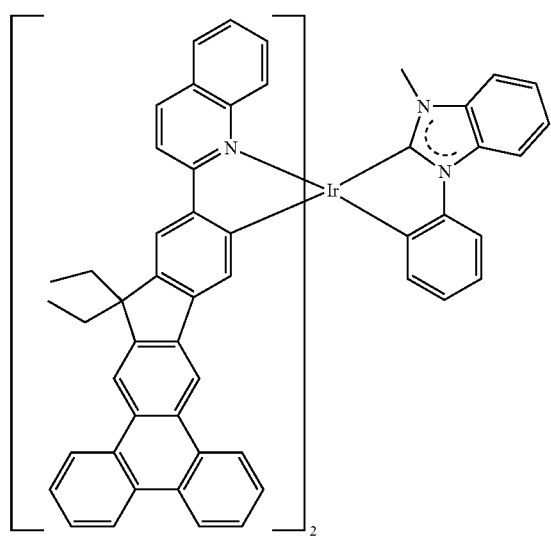
EX200
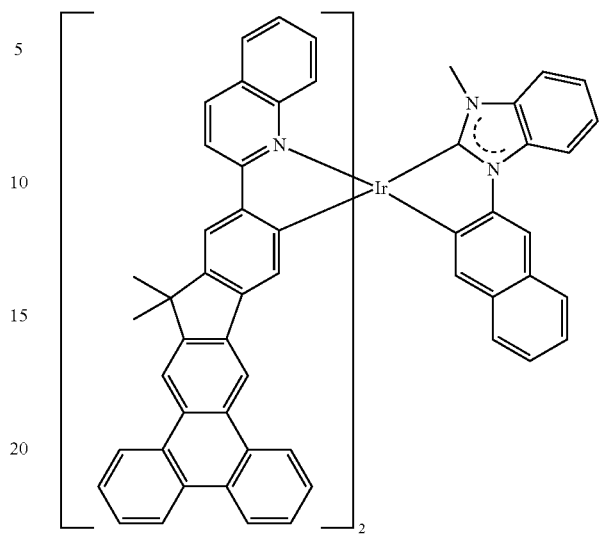
EX201
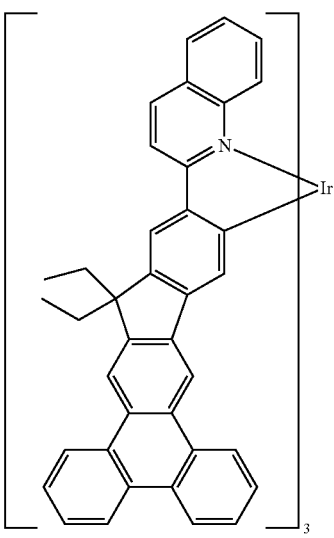
EX202
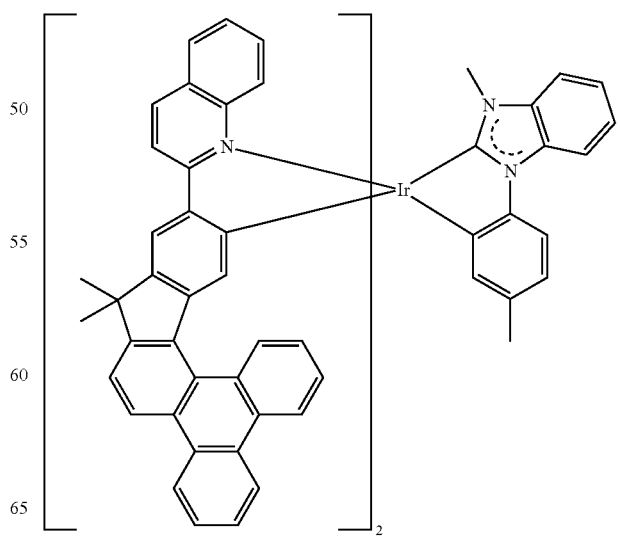

EX203
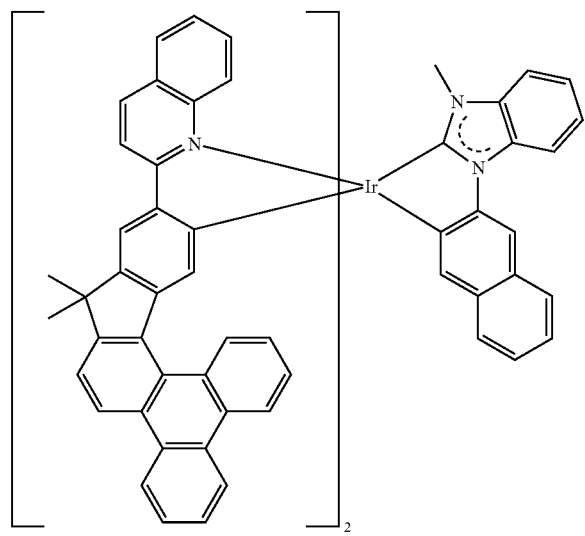
EX206
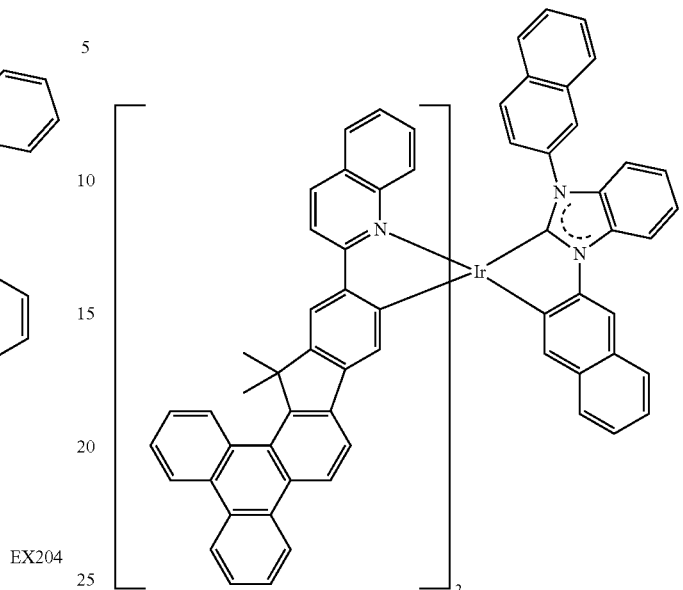
EX204
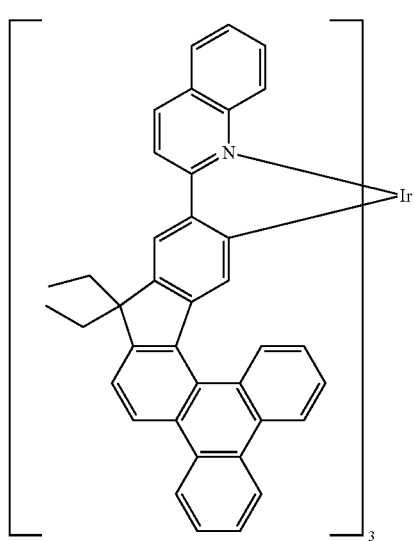
EX207
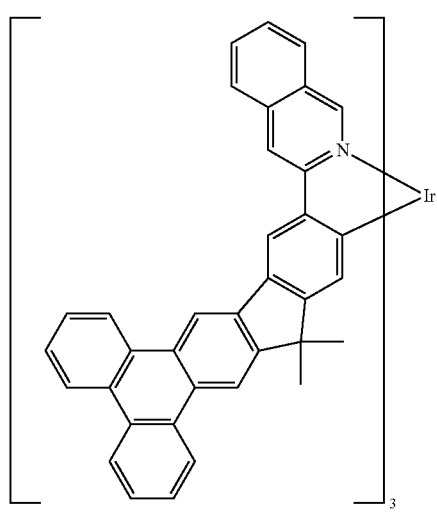
EX205
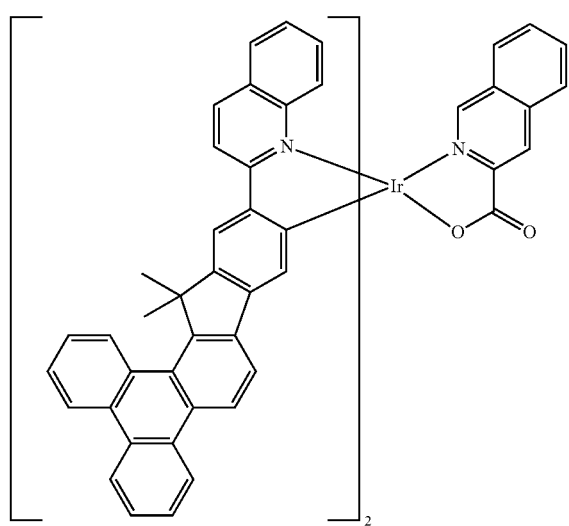
EX208
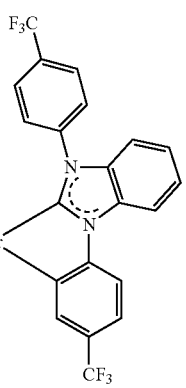

EX209
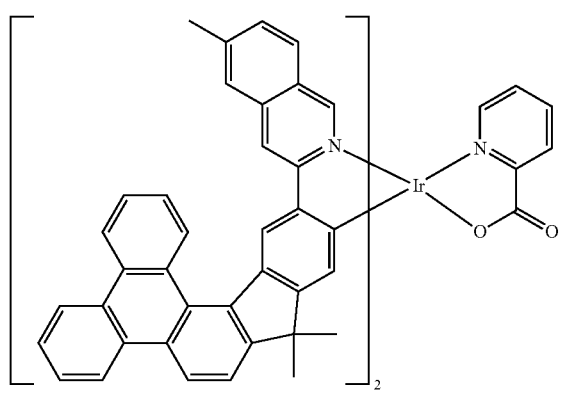
EX210
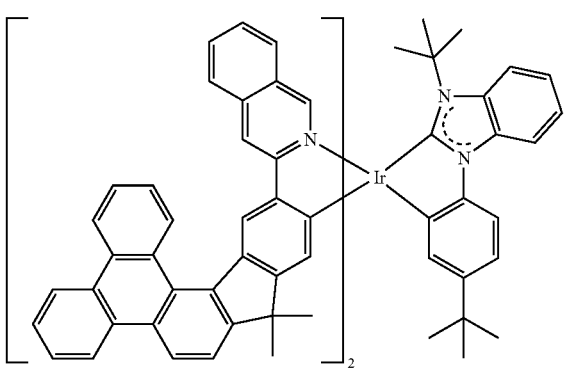
EX211
EX212
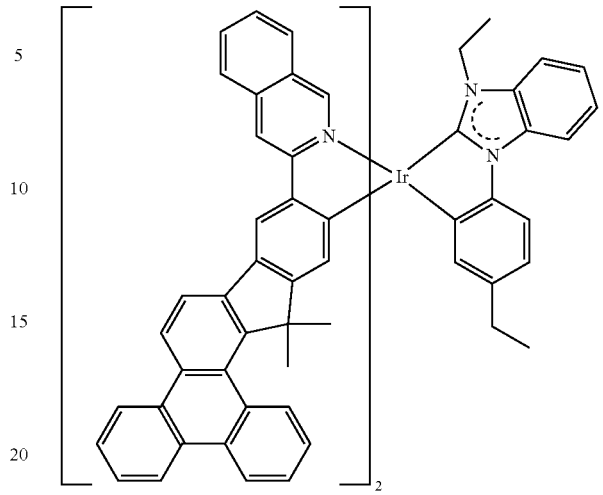
EX213
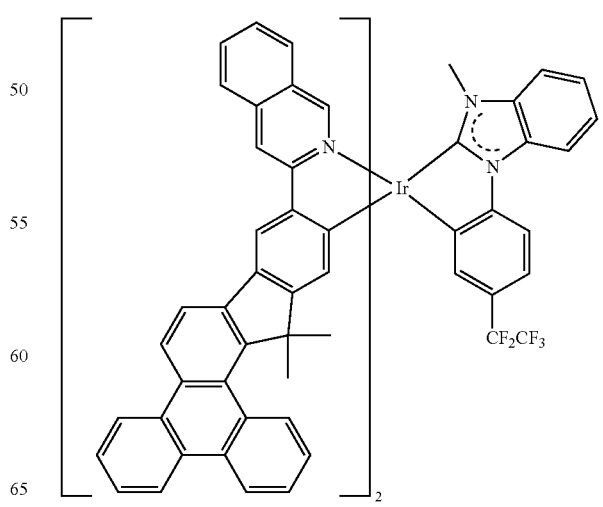

EX214
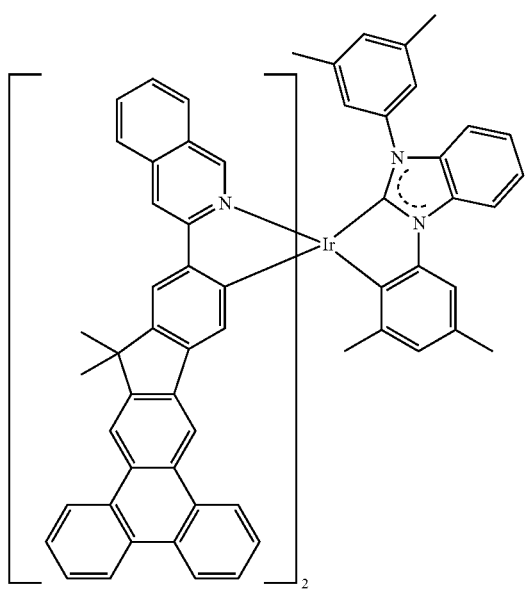
EX215
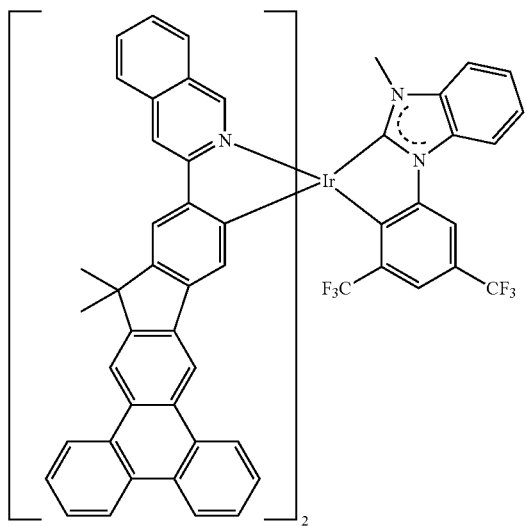
EX216
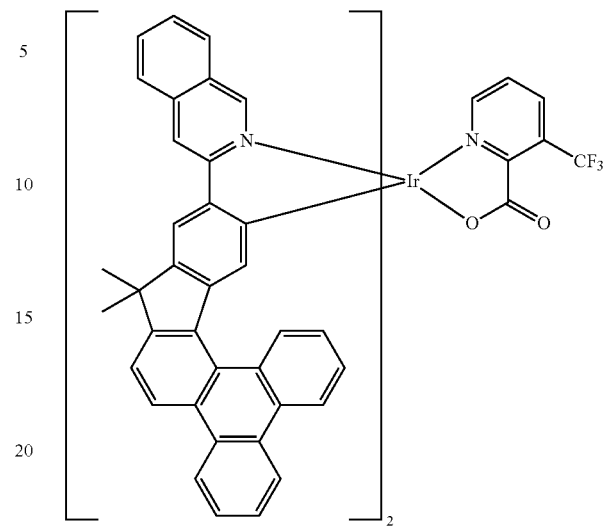
EX217
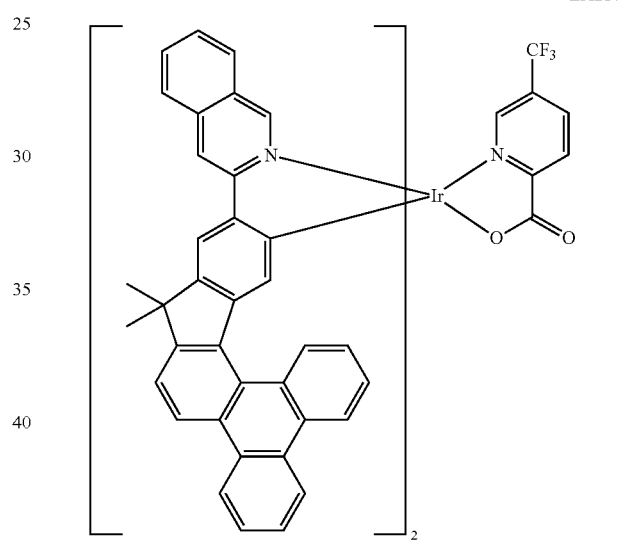
EX218
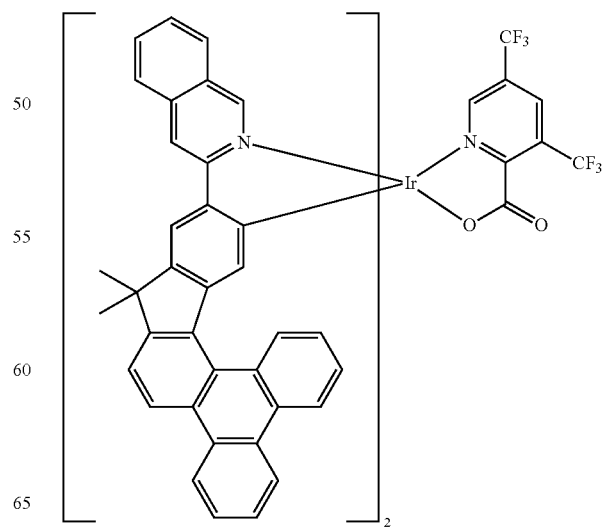

EX219
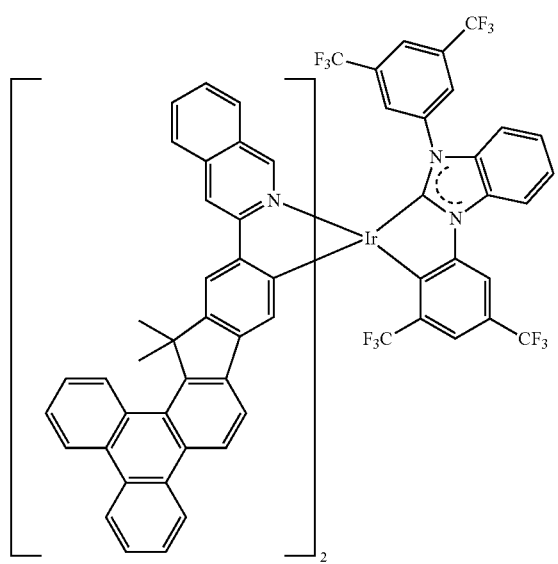
EX220
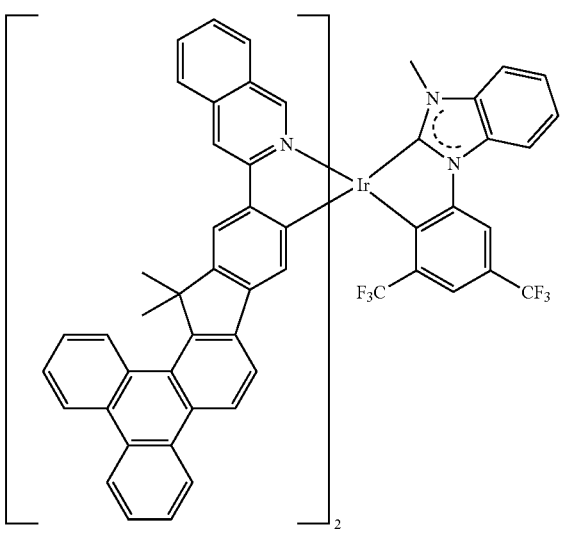
EX221
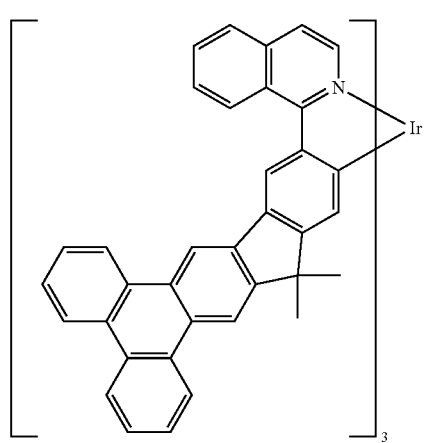
EX222
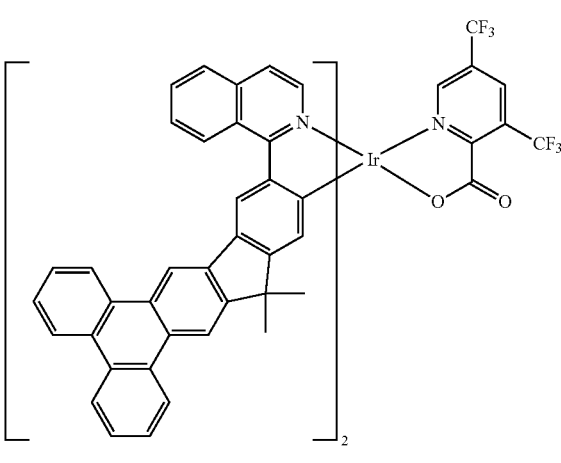
EX223
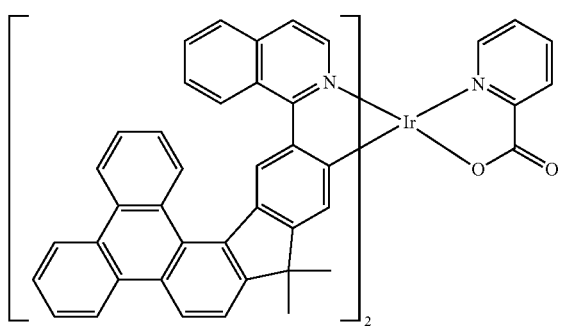
EX224
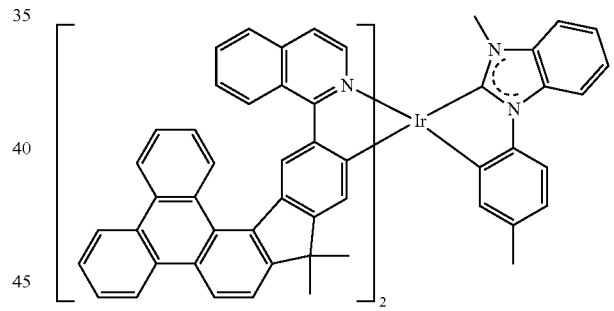
EX225
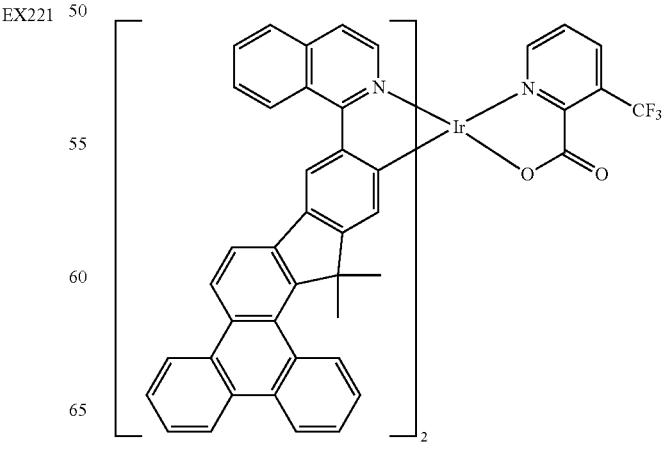

EX226
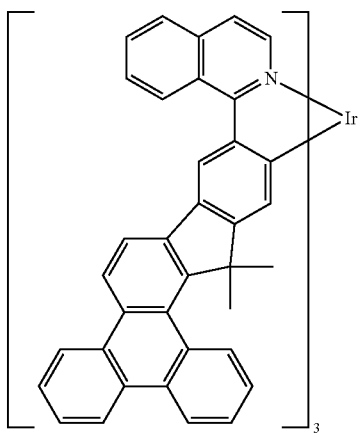
EX227
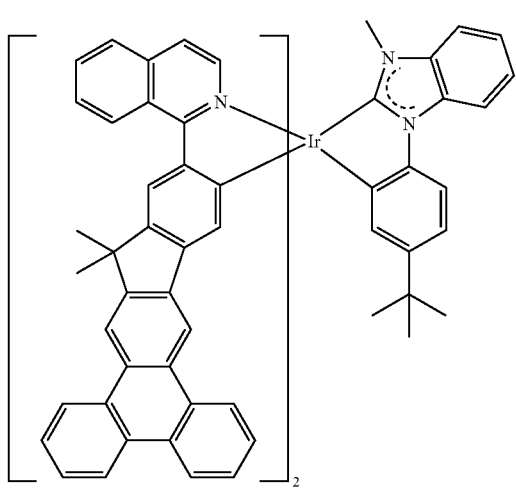
EX228
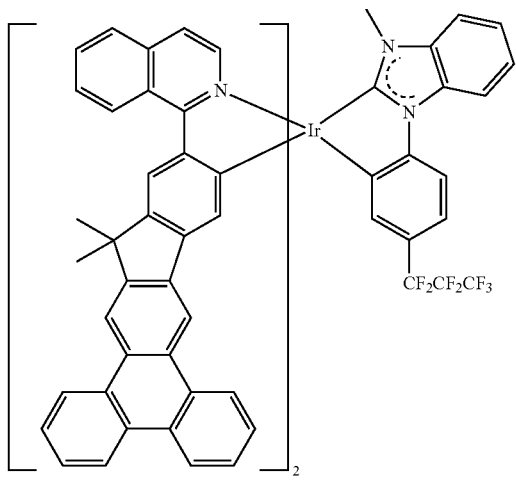
EX229
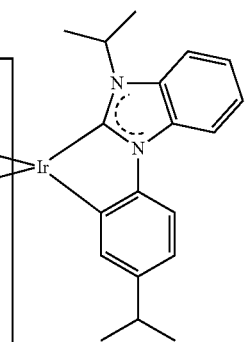
EX230
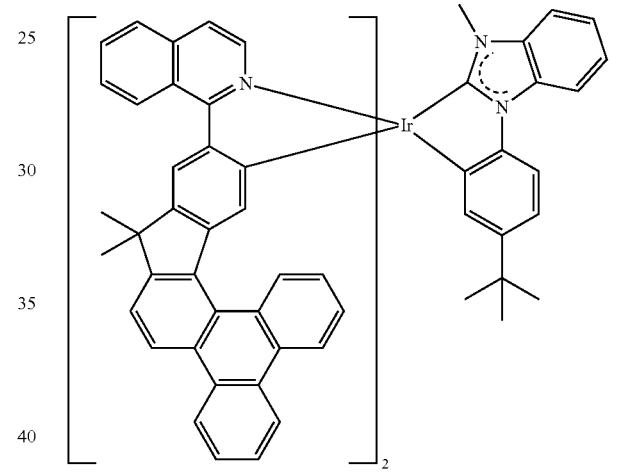
EX231
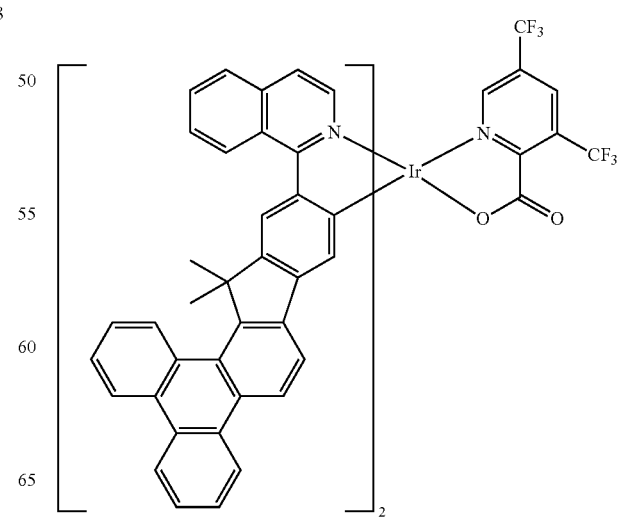

EX232
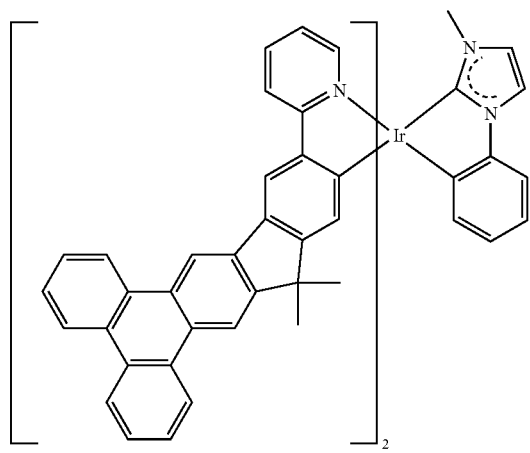
EX233
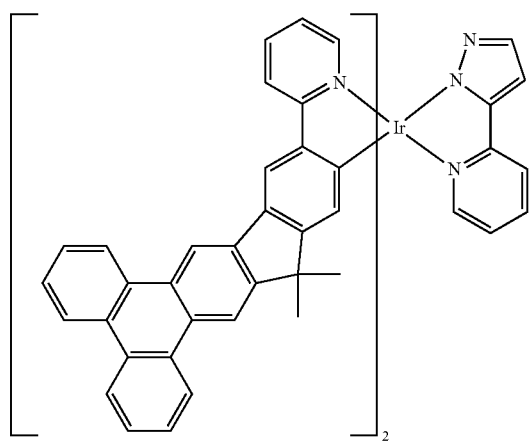
EX234
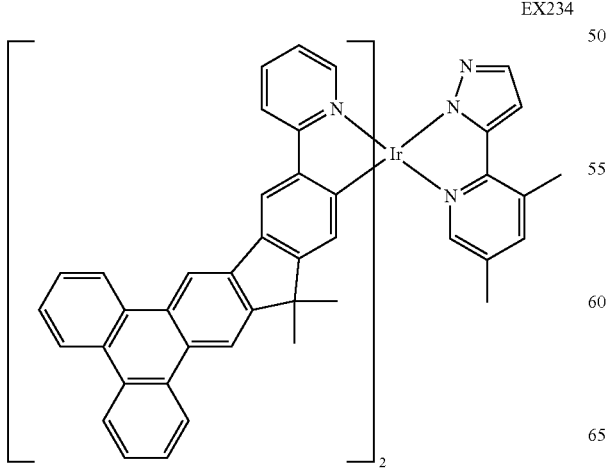
EX235
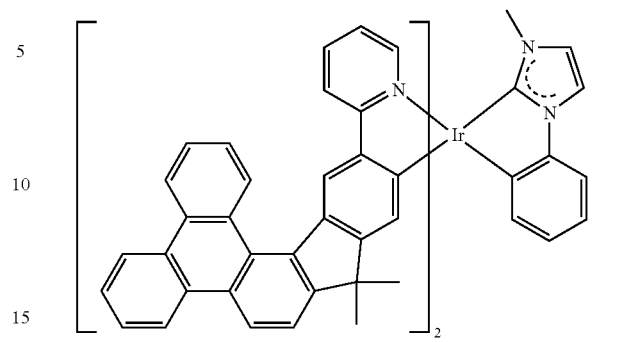
EX236
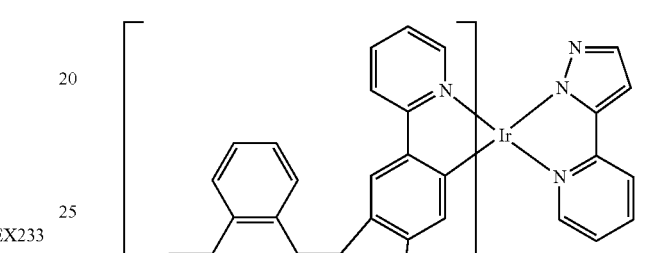
EX237
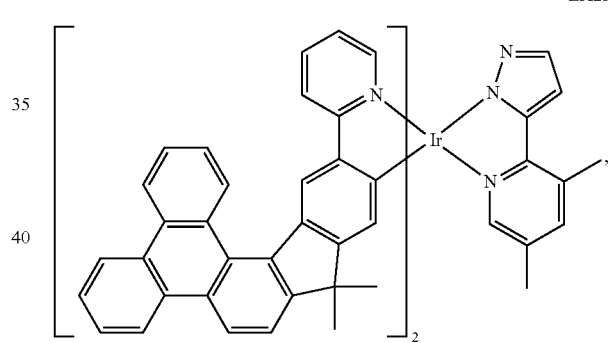
EX238
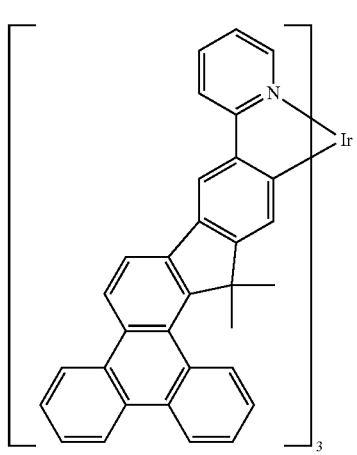

EX239
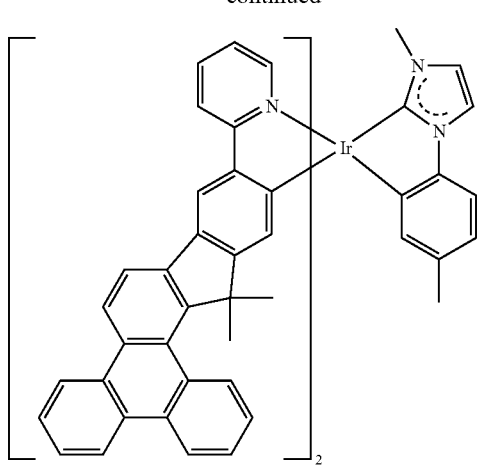
EX242
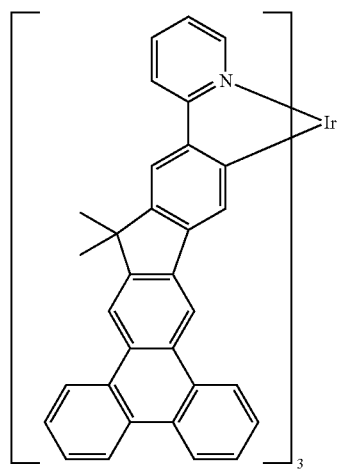
EX240
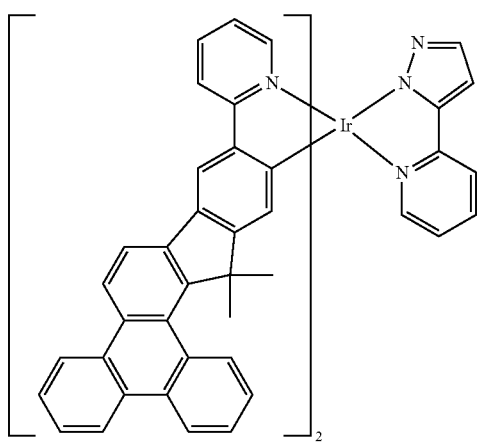
EX243
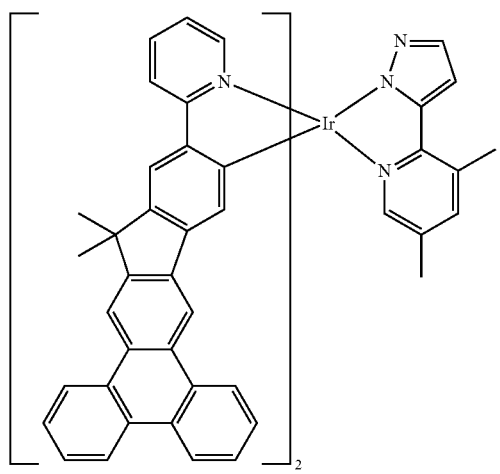
EX241
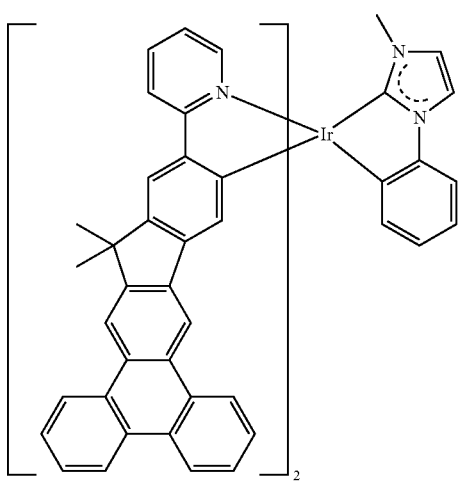
EX244
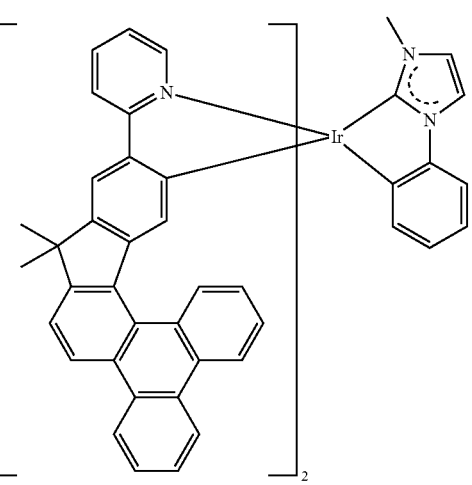

EX245
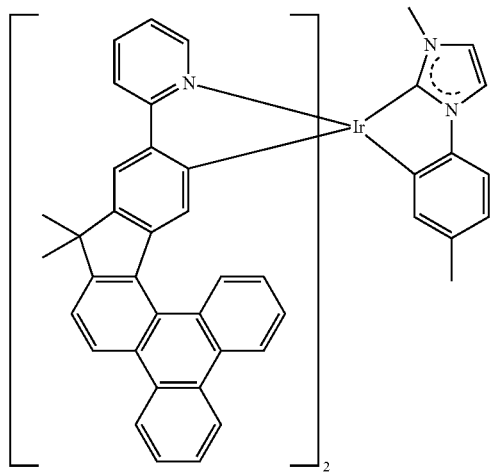
EX248
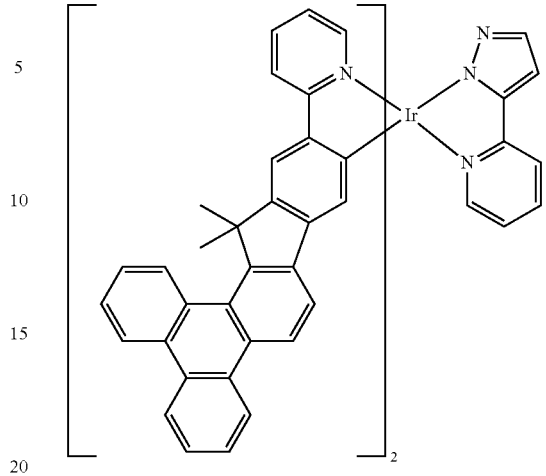
EX246
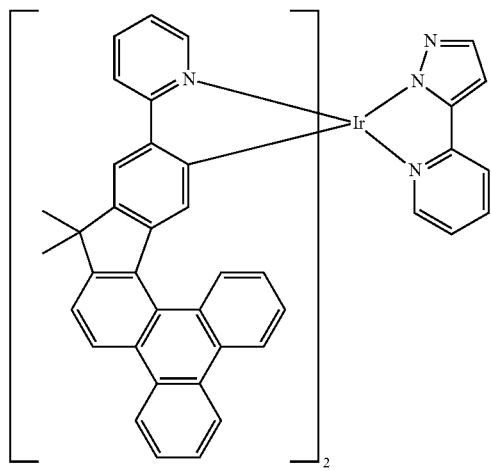
EX249
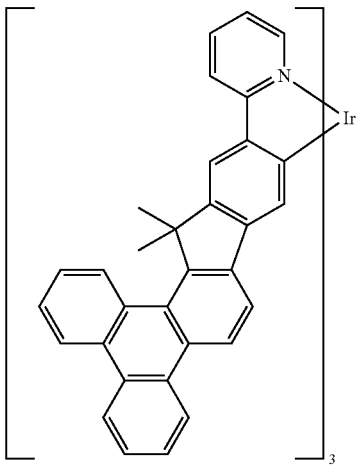
EX247
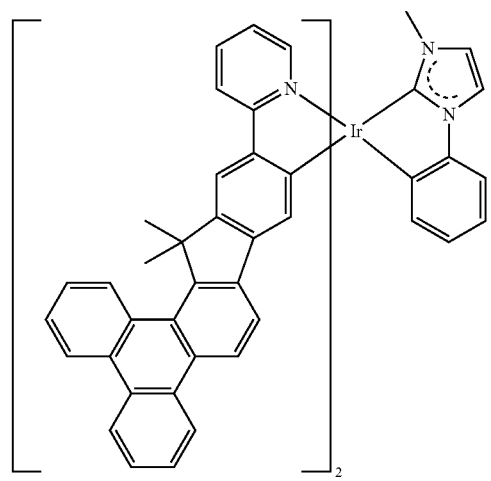
EX250
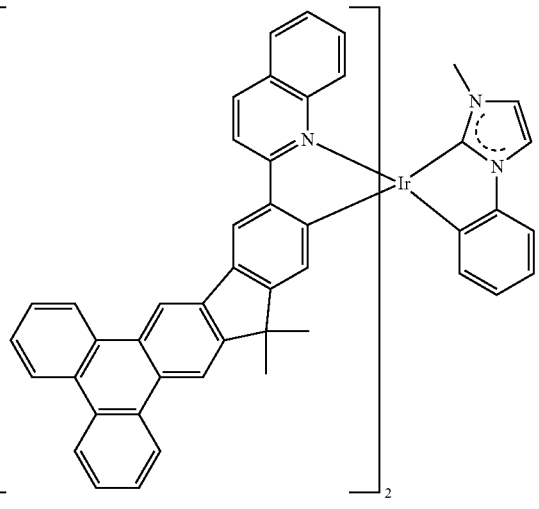

-continued
EX251
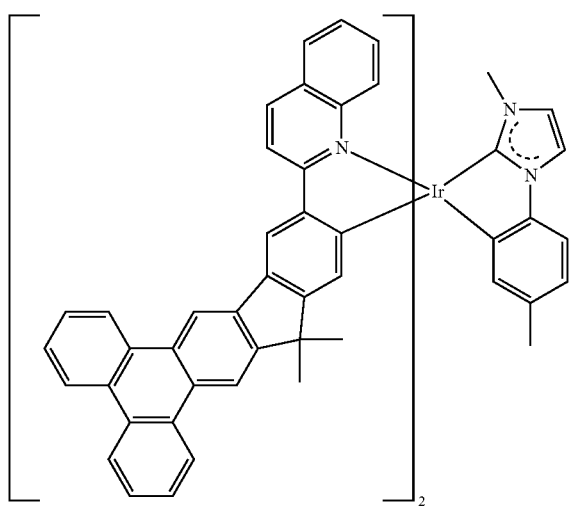
EX252
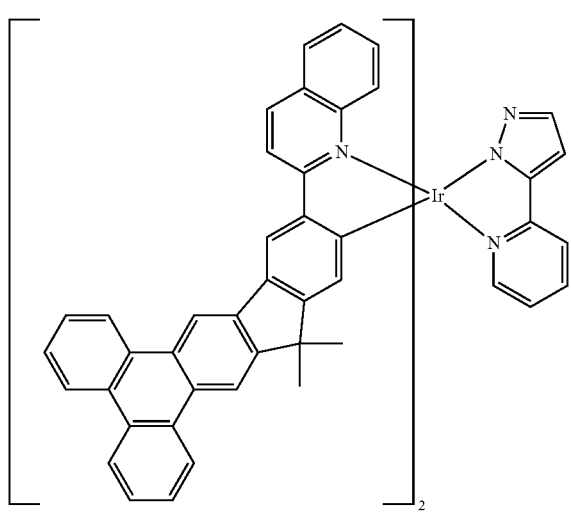
EX253
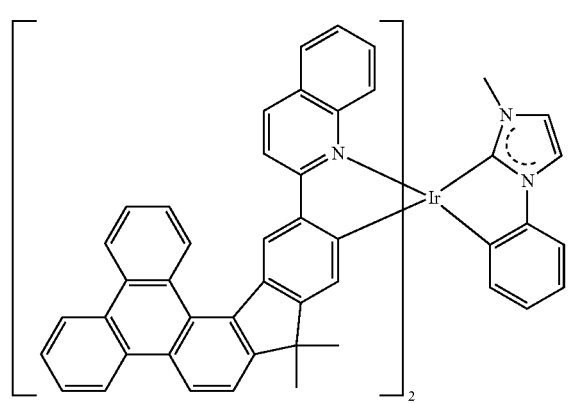
-continued
EX254
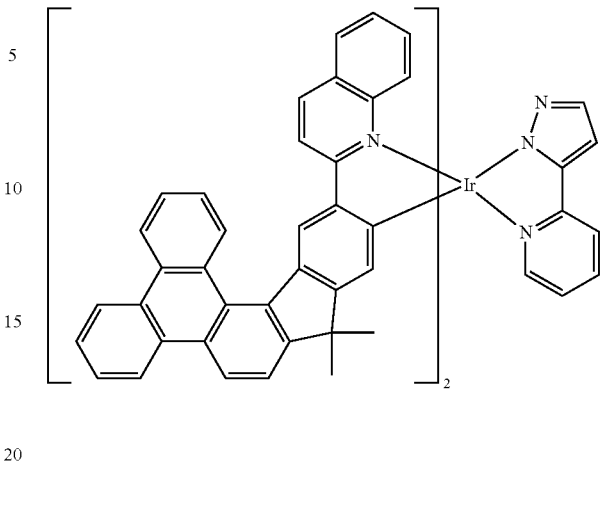
EX255
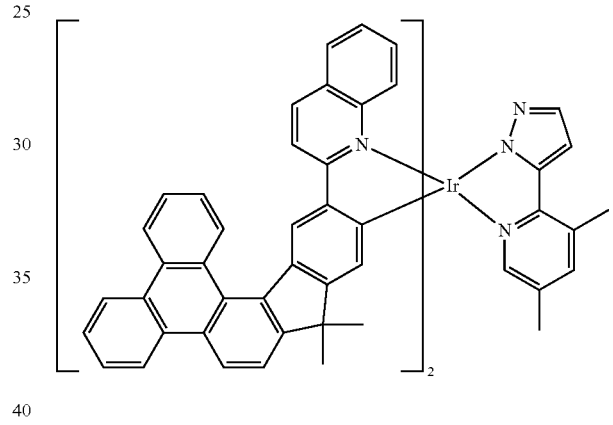
EX256
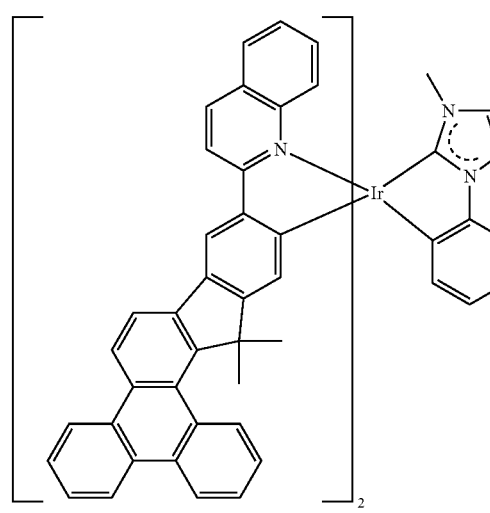

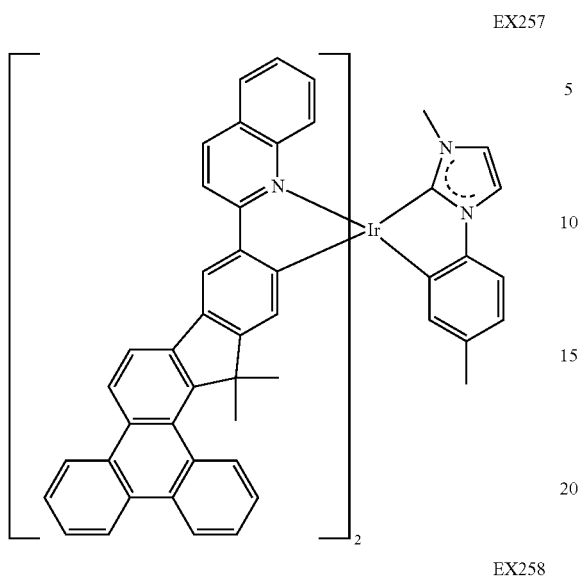
EX257
EX258
EX259
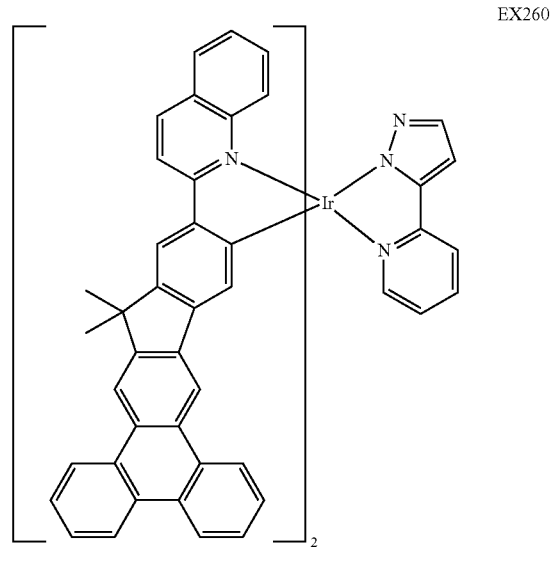
EX260
EX261
EX262

EX263
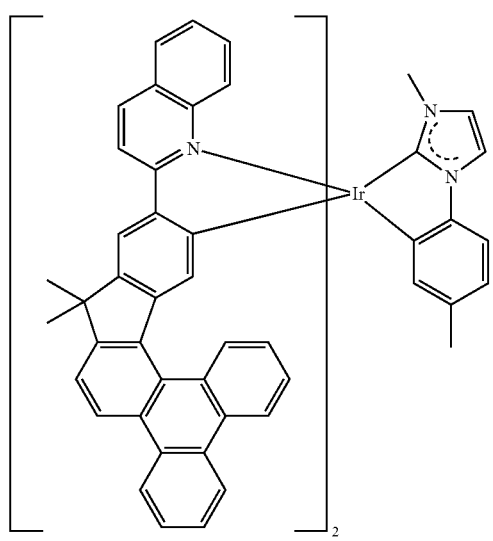
EX264
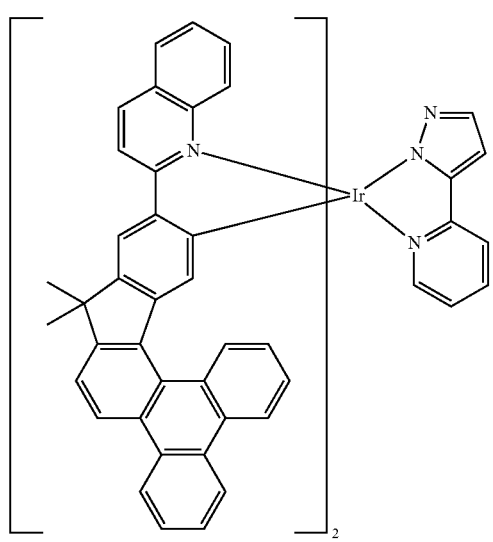
EX265
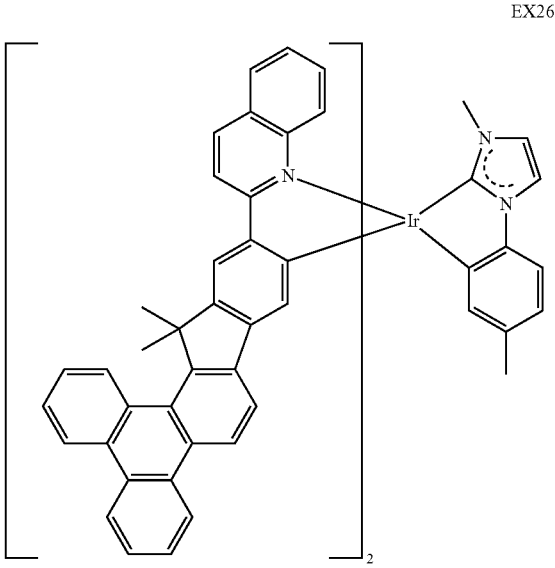
EX266
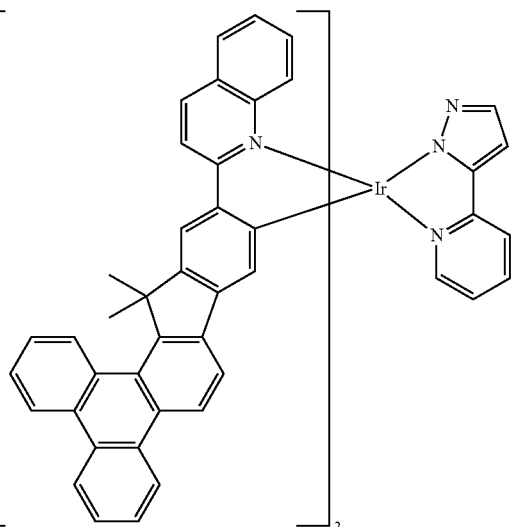
EX267
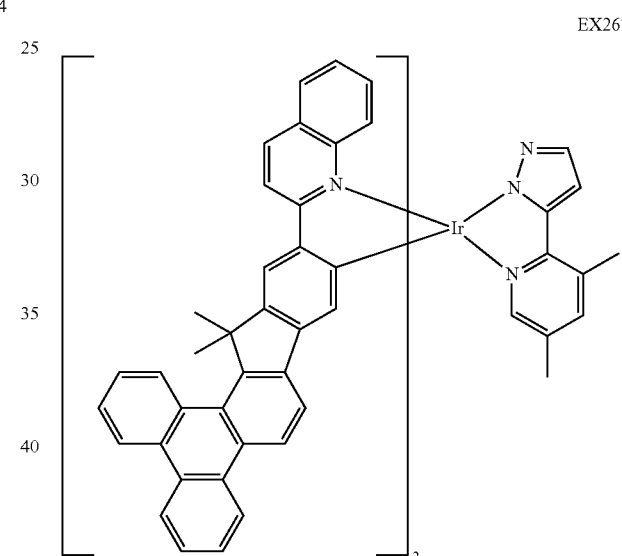
EX268
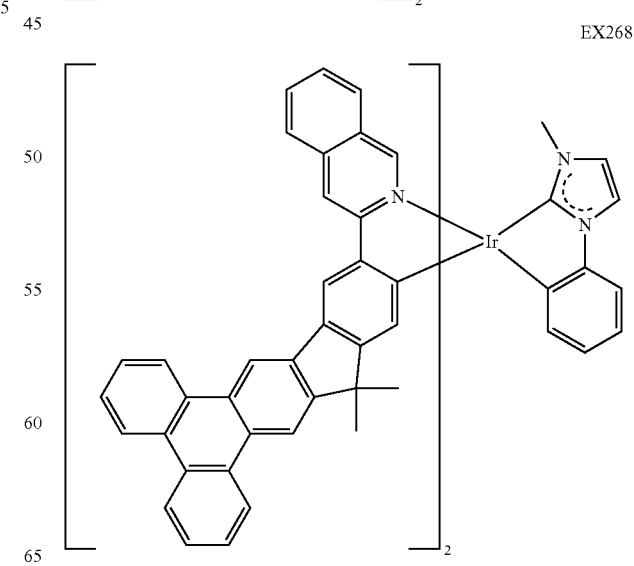

EX269
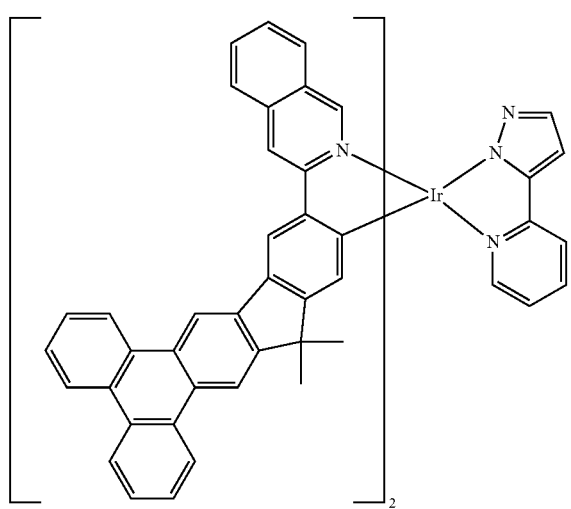
EX270
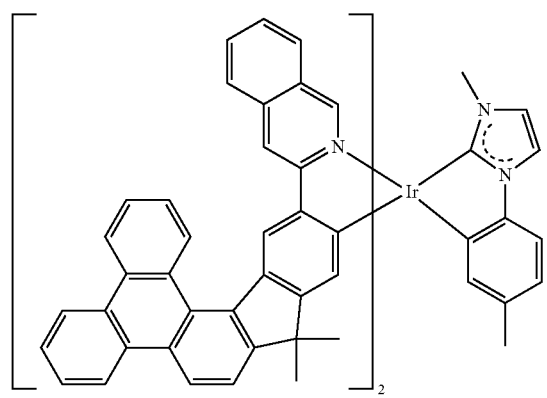
EX271
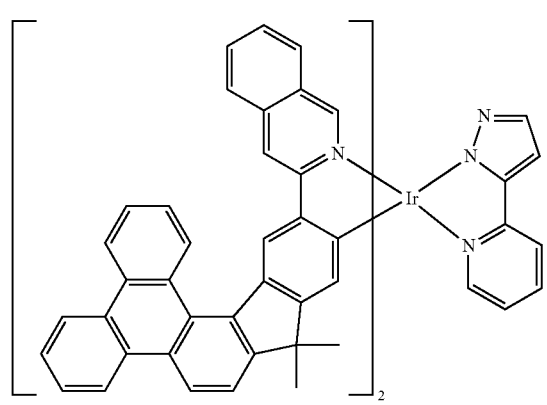
EX272
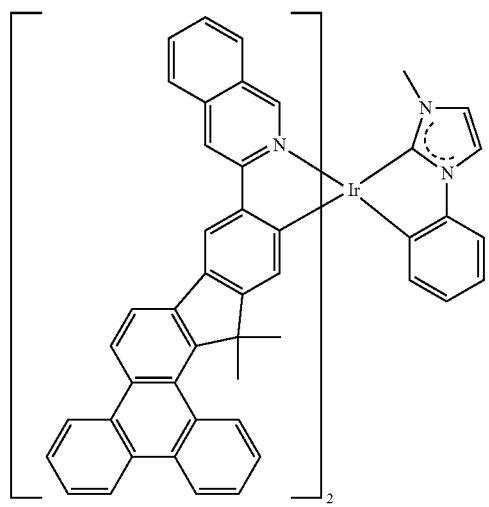
EX273
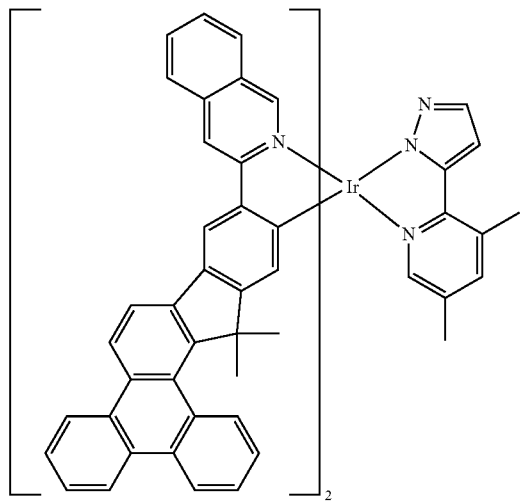
EX274
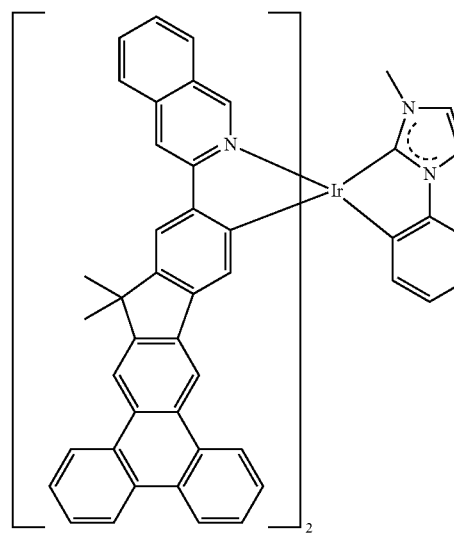

EX275
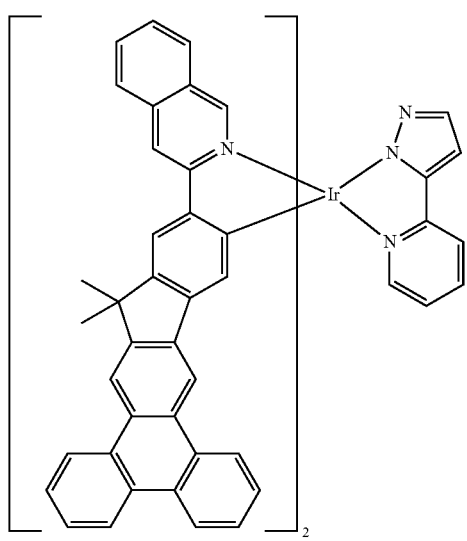
EX276
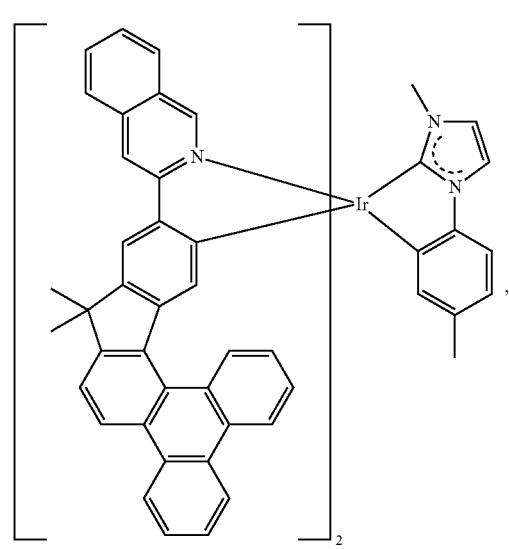
EX277
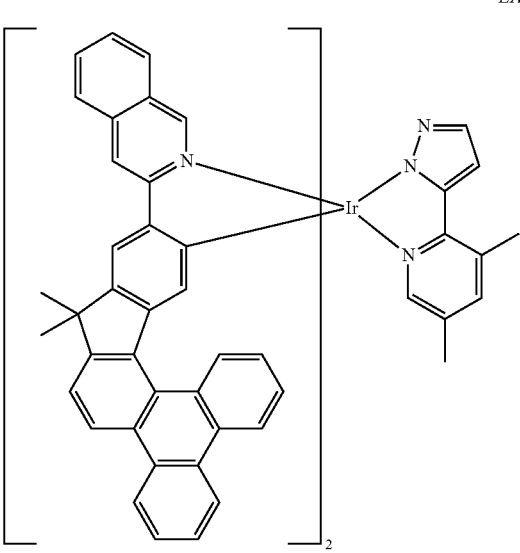
EX278
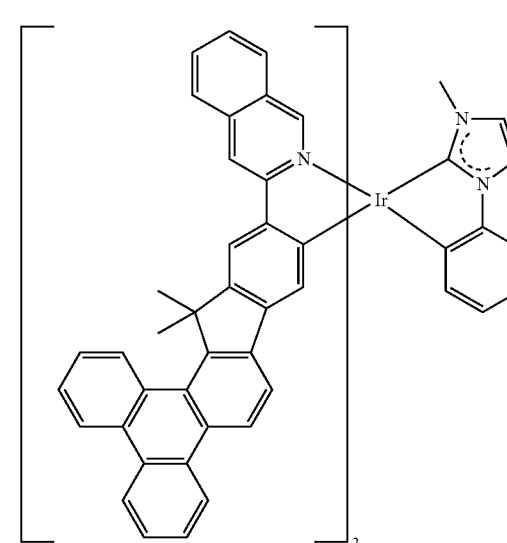
EX279
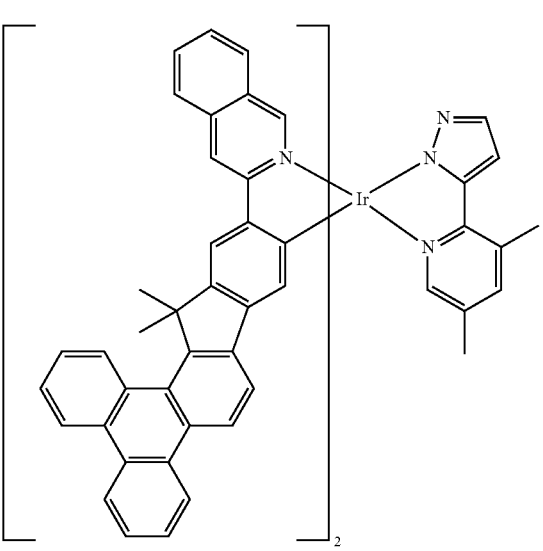
EX280
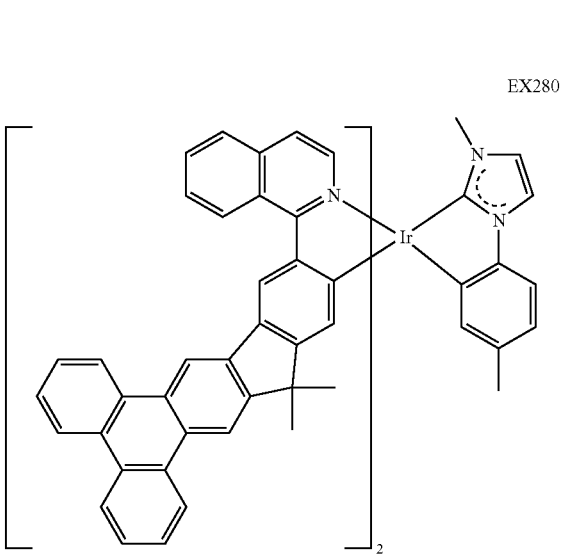

EX281
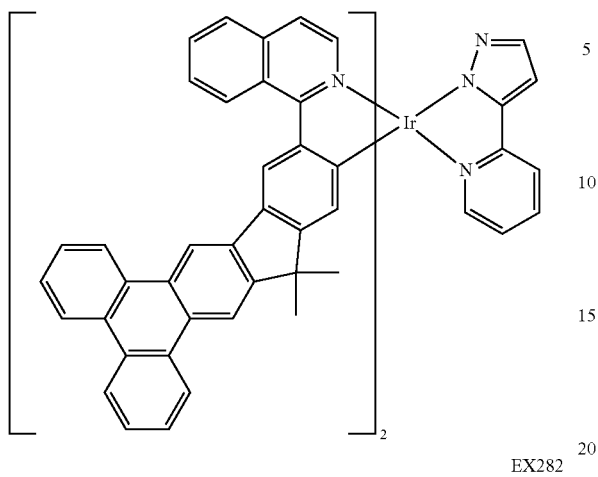
EX282
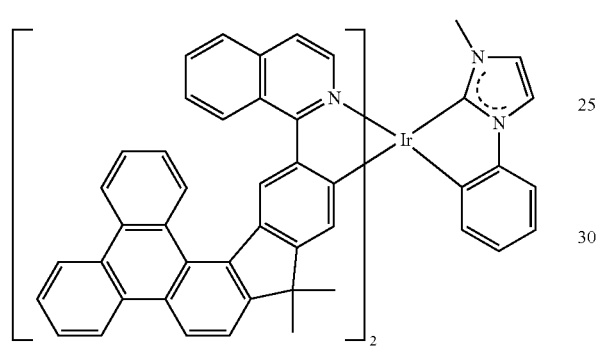
EX283
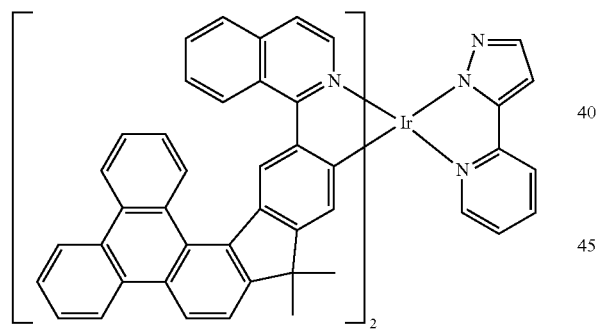
EX284
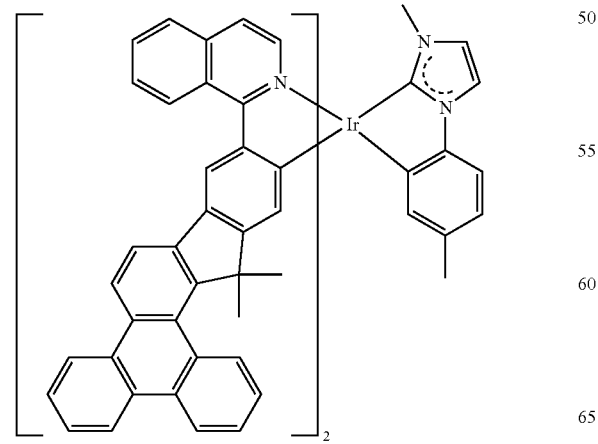
EX285
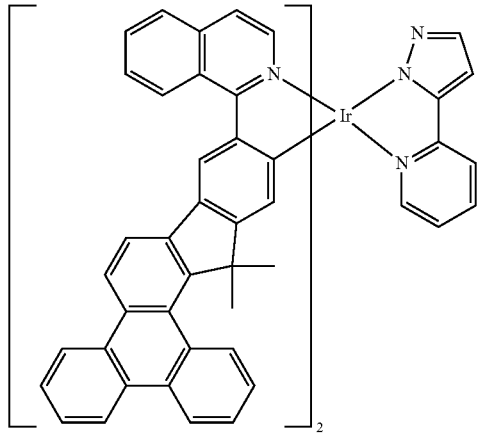
EX286
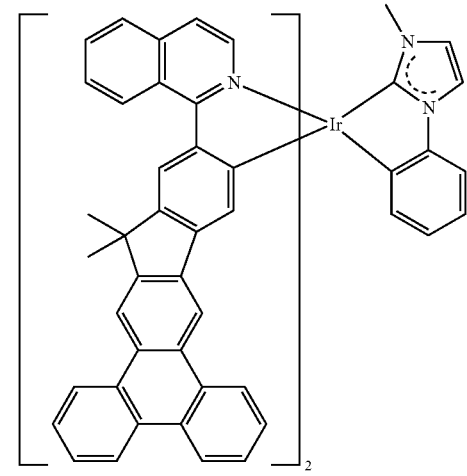
EX287
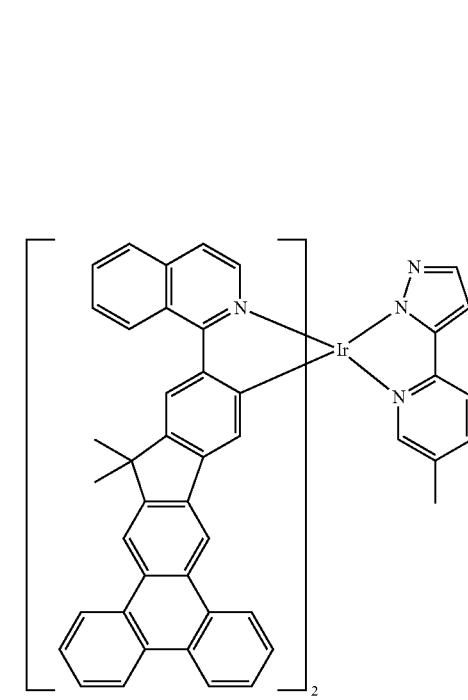

EX288

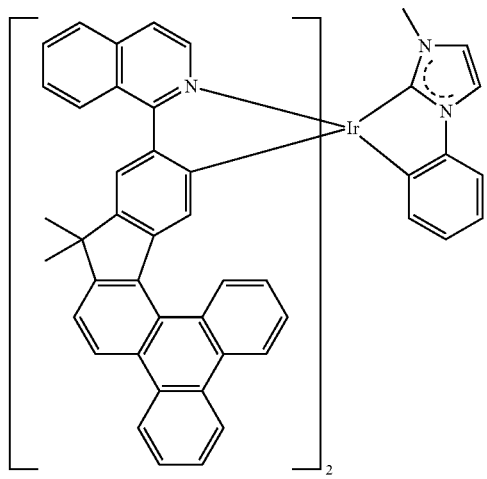

EX289

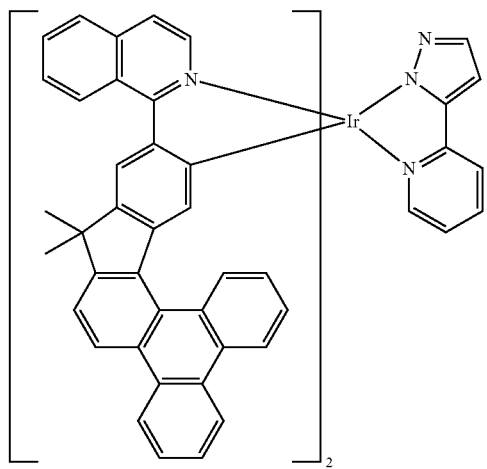

EX290

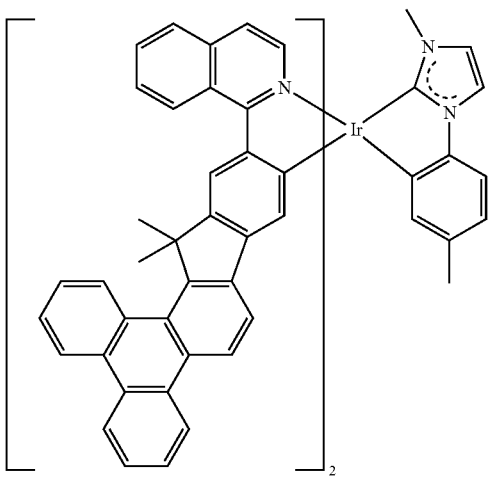

EX291

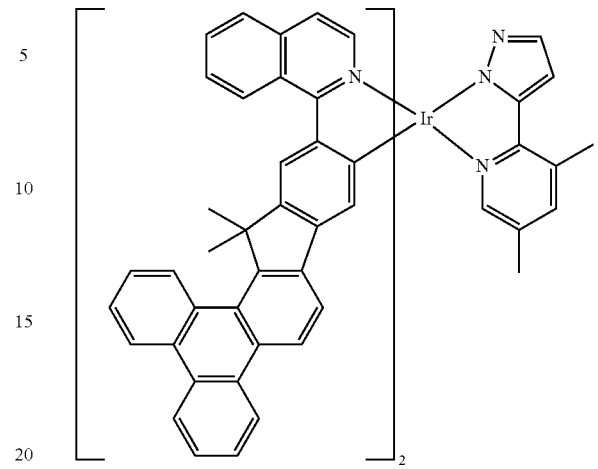

Detailed preparation for the indenotriphenylene-based iridium complexes present invention could be clarified by exemplary embodiments, but the present invention is not limited to exemplary embodiments. EXAMPLE 1 and EXAMPLE 4 show the preparation for examples of the derivative in the present invention. EXAMPLE 5 shows the fabrication of organic EL device and I-V-B, half-life time of organic EL device testing report.

Example 1

Synthesis of EX2

Synthesis of 2-(biphenyl-2-yl)-6-bromo-9,9-dimethyl-9H-fluorene

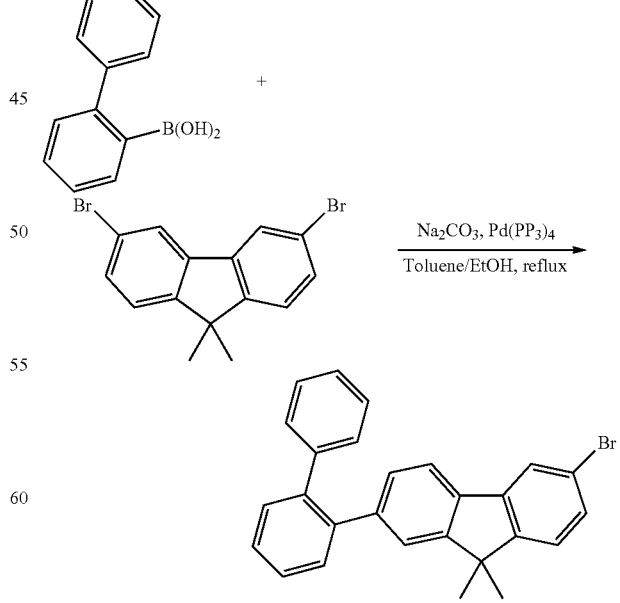

A mixture of 35.2 g (100 mmol) of 3,6-dibromo-9,9-dimethyl-9H-fluorene, 21.8 g (110 mmol) of biphenyl-2- ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of
13-bromo-10,10-dimethyl-10H-indeno[2,1-b]
triphenylene

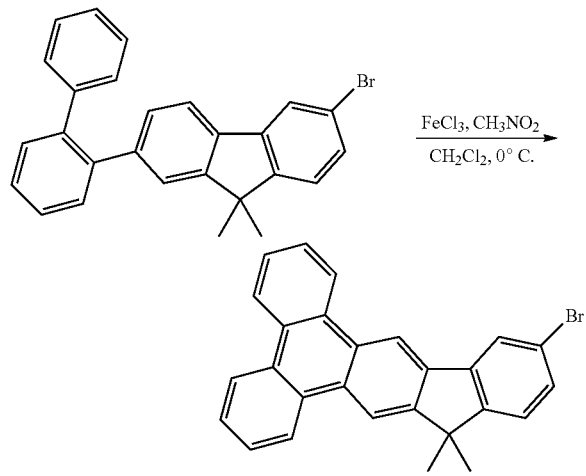

In a 3000 ml three-necked flask that had been degassed and filled with nitrogen, 26.8 g (60 mmol) of 2-(biphenyl-2-yl)-7-bromo-9,9-Dimethyl-9H-fluorene was dissolved in anhydrous dichloromethane (1500 ml), 97.5 g (600 mmol) iron (III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). 1H NMR (CDCl$_3$, 500 MHz): chemical shift (ppm) 8.93 (s, 1H), 8.77~8.71 (m, 2H), 8.67~8.65 (m, 3H), 8.08 (d, J=1.5 Hz, 1H), 7.71~7.64 (m, 4H), 7.49 (dd, J$_1$=8.5 Hz, J$_2$=1.5 Hz, 1H), 7.37 (d, J=8.5 Hz, 1H), 1.62 (s, 6H).

Synthesis of 2-(10,10-dimethyl-10H-indeno[2,1-b]
triphenylen-13-yl)-4,4,5,5-tetramethyl-1,3,2-dioxaborolane

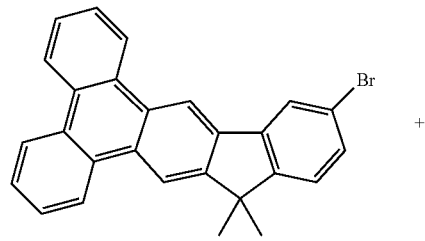

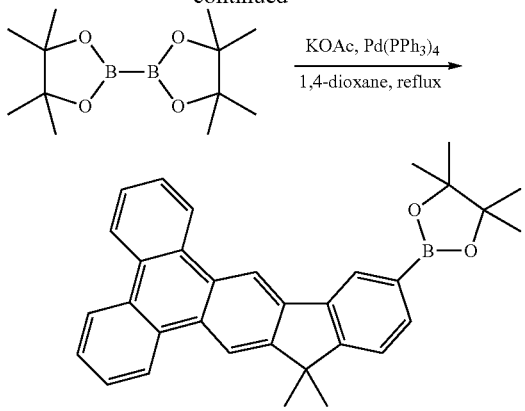

A mixture of 10.7 g (25.3 mmol) of 13-bromo-10,10-dimethyl-10H-indeno[2,1-b]triphenylene, 7.7 g (30.3 mmol) of bis(pinacolato)diboron, 0.3 g (0.26 mmol) of Pd(PPh$_3$)$_4$, 7.4 g (75.4 mmol) of potassium acetate, and 500 ml 1,4-dioxane was degassed and placed under nitrogen, and then heated at 90° C. for 16 h. After finishing the reaction, The mixture was allowed to cool to room temperature. The organic phase separated and washed with ethyl acetate and water. After drying over magnesium sulfate, the solvent was removed in vacuum. The residue was purified by column chromatography on silica to give product (9.5 g, 20.2 mmol, 80%) as a light-yellow solid; 1H NMR (CDCl$_3$, 500 MHz): chemical shift (ppm) 8.93 (s, 1H), 8.77~8.71 (m, 2H), 8.67~8.65 (m, 3H), 7.88 (d, J=1.5 Hz, 1H), 7.71~7.64 (m, 4H), 7.29 (dd, J$_1$=8.5 Hz, J$_2$=1.5 Hz, 1H), 7.42 (d, J=8.5 Hz, 1H), 1.62 (s, 6H), 1.42 (s, 12H).

Synthesis of 2-(10,10-dimethyl-10H-indeno[2,1-b]
triphenylen-13-yl)pyridine

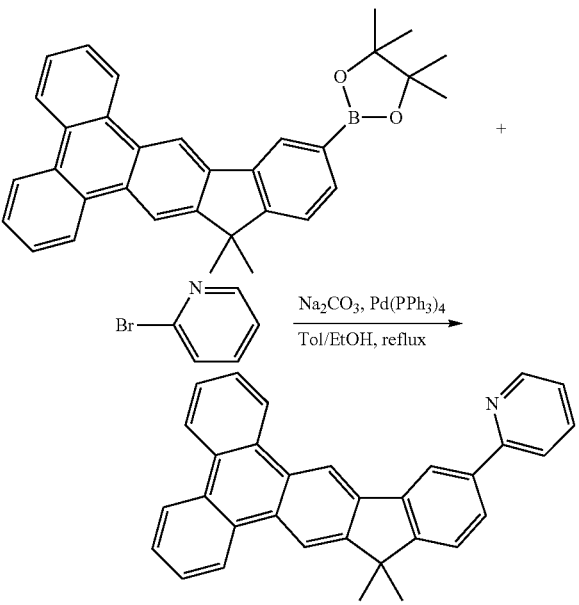

A mixture of 9.5 g (20.2 mmol) of 2-(10,10-dimethyl-10H-indeno [2,1-b]triphenylen-13-yl)-4,4,5,5-tetramethyl-1,3,2-dioxaborolane, 3.3 g (21 mmol) of 2-bromopyridine, 0.44 g (0.4 mmol) of tetrakis(triphenyl phosphine)palladium, 30 ml of 2M Na$_2$CO$_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica (Hx~EA) to give product 6.0 g (88%).

Synthesis of Dichloro-Bridged Dimer

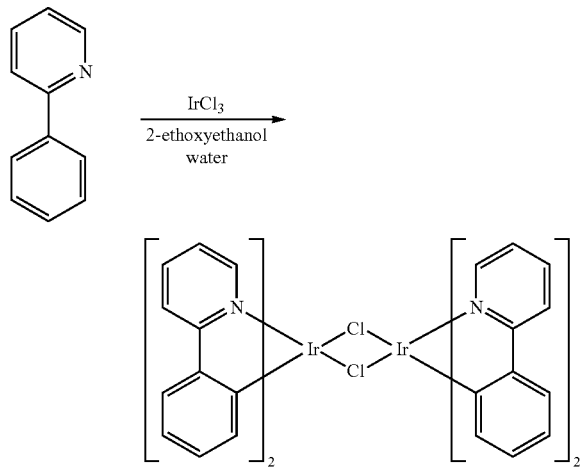

A mixture of 7.35 g (20 mmol) of iridium (III) chloride, 13 g (85 mmol) of 2-phenylpyridine, 120 ml of 2-methoxyethanol and 30 ml of distilled water, was placed under nitrogen, and then heated reflux overnight. After finishing the reaction, the mixture was allowed to cool to room temperature. The yellow precipitate formed was vacuum filtered and washed with ethanol and hexanes. The dichlorobridged dimer was dried in a vacuum oven to give 10 g. The product was not purified any further but used directly in the next step.

Synthesis of Iridium Triflate Precursor

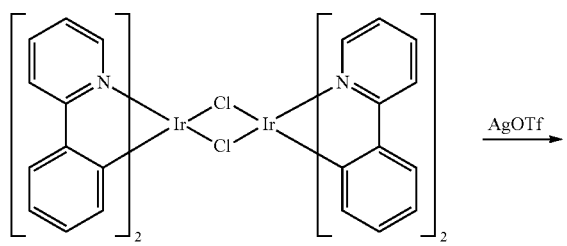

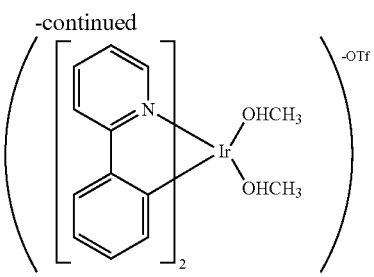

A mixture of 9.6 g of dichloro-bridged dimer, 4.6 g (17.5 mmol) of silver triflate, 300 ml of dichloromethane and 5 ml of methanol, was placed under nitrogen, and then stirred overnight. After finishing the reaction, the silver chloride was filtered off. The solvent was evaporated. 10 g of product was obtained. The product was not purified any further but used directly in the next step.

Synthesis of EX2

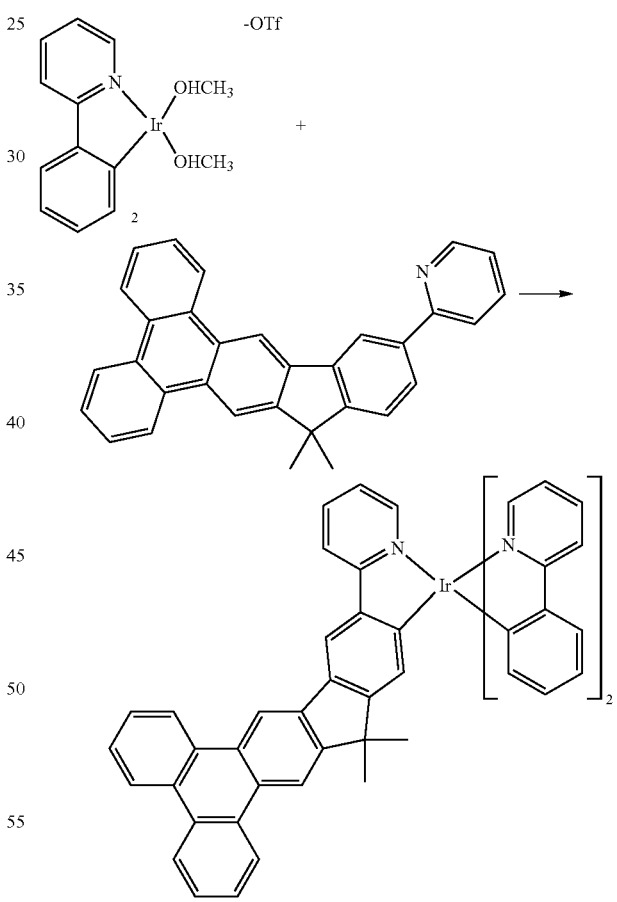

A mixture of 9 g (11.3 mmol) of iridium triflate precursor, 9.7 g (23 mmol) of 2-(10,10-dimethyl-10H-indeno[2,1-b]triphenylen-13-yl) pyridine, 120 ml of EtOH and 30 ml of MeOH, was placed under nitrogen, and then heated reflux overnight. After finishing the reaction, the mixture was allowed to cool to room temperature. The yellow precipitate formed was vacuum filtered and washed with ethanol and hexanes, the product was purified by vacuum sublimation to give 4.3 g of yellow product. 1H NMR (CDCl₃, 500 MHz): chemical shift (ppm) 9.27 (s, 1H), 8.98~8.97 (d, 1H), 8.89~8.88 (d, 1H), 8.81~8.77 (m, 3H), 8.63 (s, 1H), 8.38~8.36 (d, 1H), 8.17~7.15 (m, 2H), 7.94~7.90 (m, 2H), 7.83~7.50 (m, 11H), 7.19~7.14 (m, 2H), 6.90~6.65 (m, 7H), 1.40 (s, 3H), 1.22 (s, 3H).

Example 2

Synthesis of EX12

Synthesis of 2-(biphenyl-2-yl)-7-bromo-9,9-dimethyl-9H-fluorene

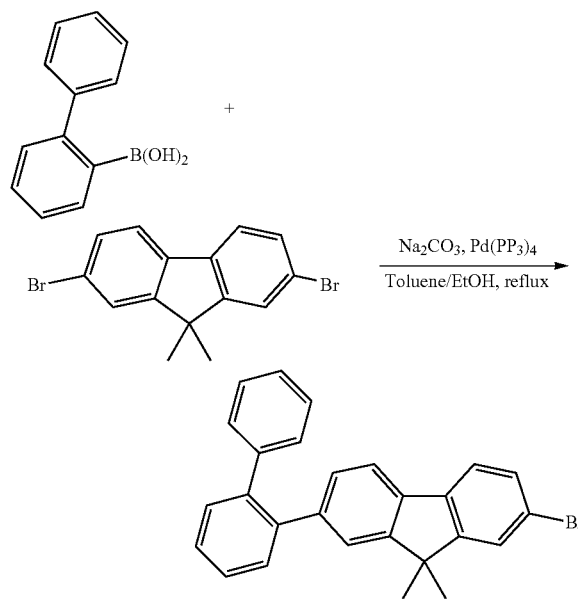

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Pd(PPh₃)₄, 75 ml of 2M Na₂CO₃, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

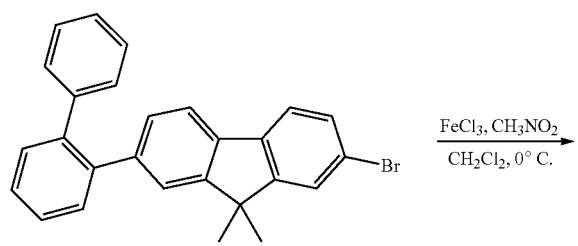

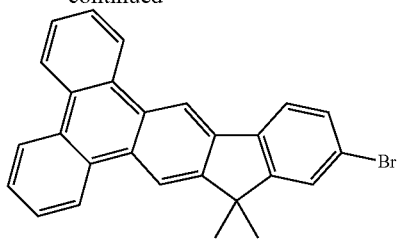

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron (III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). 1H NMR (CDCl3, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[2,1-b]triphenylen-12-yl)-4,4,5,5-tetramethyl-1,3,2-dioxaborolane

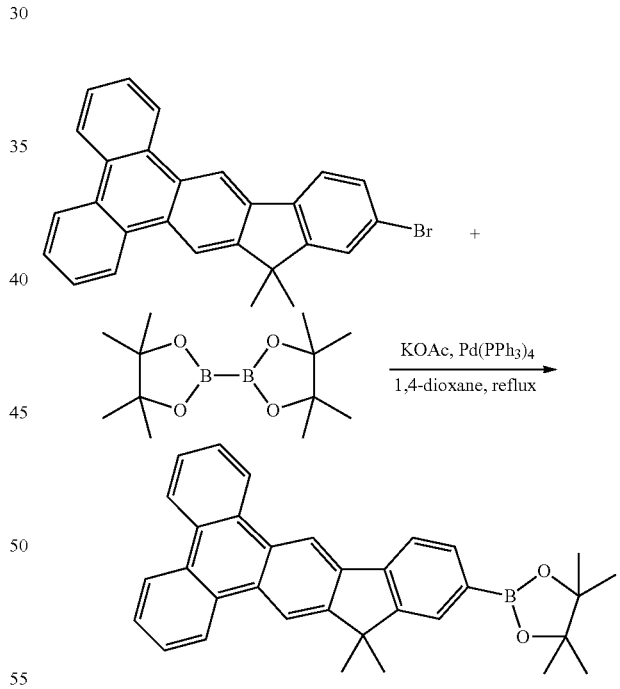

A mixture of 10.7 g (25.3 mmol) of 12-bromo-10,10-dimethyl-10H-indeno-[1,2-b]triphenylene, 7.7 g (30.3 mmol) of bis(pinacolato)diboron, 0.3 g (0.26 mmol) of Pd(PPh₃)₄, 7.4 g (75.4 mmol) of potassium acetate, and 300 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid; 1H NMR (CDCl3, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of 2-(10,10-dimethyl-10H-indeno[2,1-b]triphenylen-12-yl)pyridine

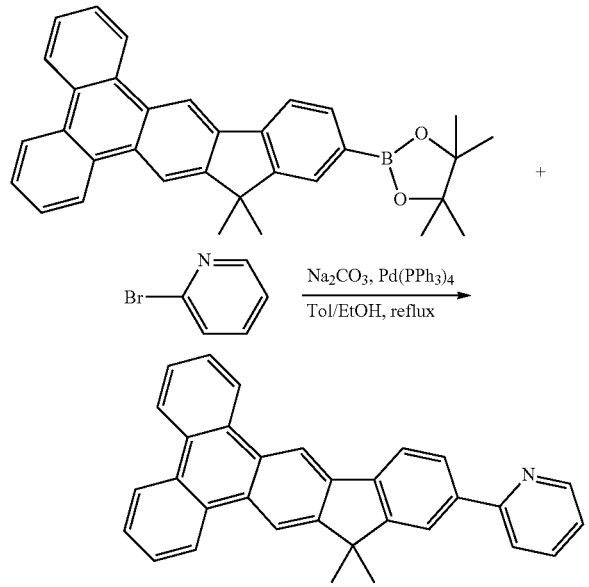

A mixture of 9.5 g (20.2 mmol) of 2-(10,10-dimethyl-10H-indeno [2,1-b]triphenylen-12-yl)-4,4,5,5-tetramethyl-1,3,2-dioxaborolane, 3.3 g (21 mmol) of 2-bromopyridine, 0.44 g (0.4 mmol) of tetrakis(triphenyl phosphine)palladium, 30 ml of 2M Na2CO3, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica (Hx~EA) to give product 6.9 g (78%).

Synthesis of EX12

2-(10,10-dimethyl-10H-indeno[2,1-b]triphenylen-12-yl)pyridine instead of 2-(10,10-dimethyl-10H-indeno[2,1-b]triphenylen-13-yl)pyridine, except for using the same method as in synthesis example 1, the desired compound of EX12 (2.7 g, yield=41%) was obtained.

Example 3

Synthesis of EX33

Synthesis of 2-(10,10-dimethyl-10H-indeno[2,1-b]triphenylen-12-yl)quinoline

-continued

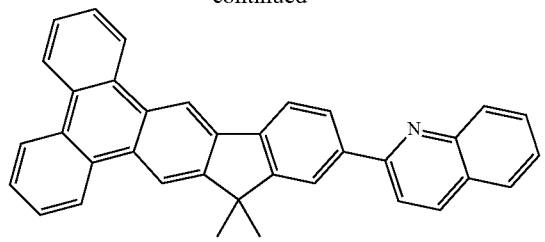

A mixture of 9.5 g (20.2 mmol) of 2-(10,10-dimethyl-10H-indeno [2,1-b]triphenylen-12-yl)-4,4,5,5-tetramethyl-1,3,2-dioxaborolane, 4.4 g (21 mmol) of 2-bromoquinoline, 0.44 g (0.4 mmol) of tetrakis(triphenyl phosphine)palladium, 30 ml of 2M $Na_2CO_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica (Hx~EA) to give product 6.8 g (71%).

Synthesis of Dichloro-Bridged Dimer

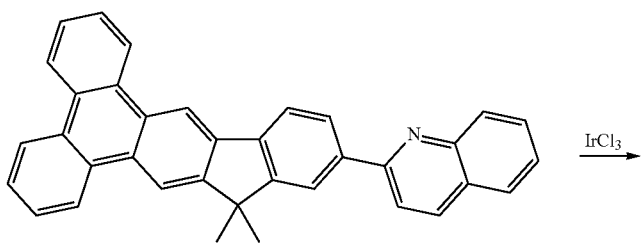

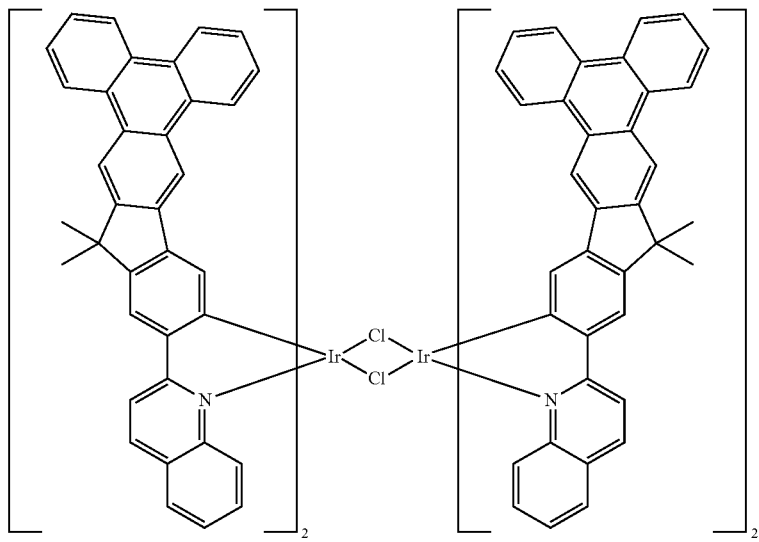

A mixture of 6.8 g (14.4 mmol) of 2-(10,10-dimethyl-10H-indeno [2,1-b]triphenylen-12-yl)quinoline, 1.7 g (5.8 mmol) of iridium (III) chloride hydrate, 30 ml of 2-methoxyethanol and 10 ml of distilled water, was placed under nitrogen, and then heated reflux overnight. After finishing the reaction, the mixture was allowed to cool to room temperature. The red precipitate formed was vacuum filtered and washed with ethanol and hexanes. The dichloro-bridged dimer was dried in a vacuum oven to give 5.0 g (62% yield). The product was not purified any further but used directly in the next step.

Synthesis of EX33

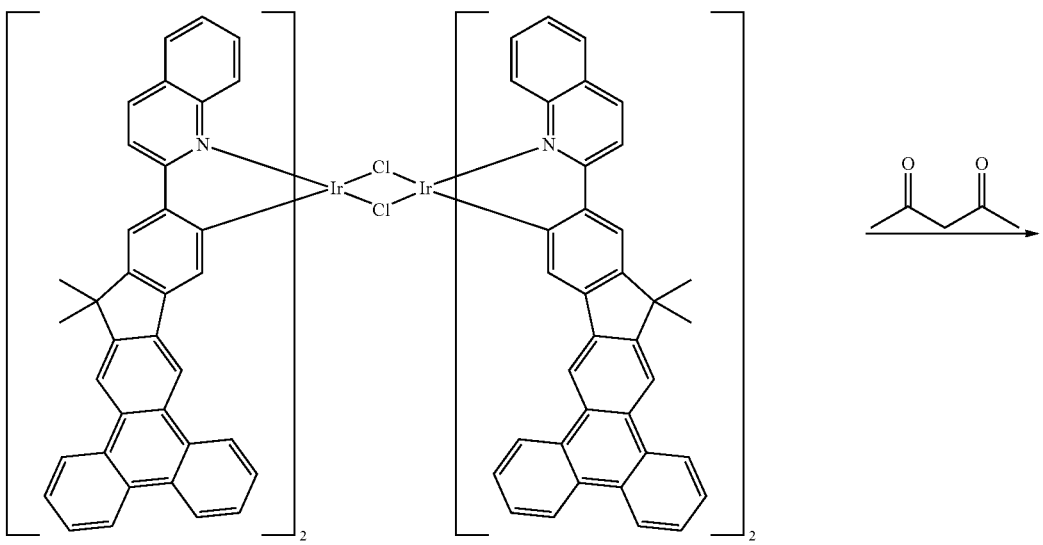

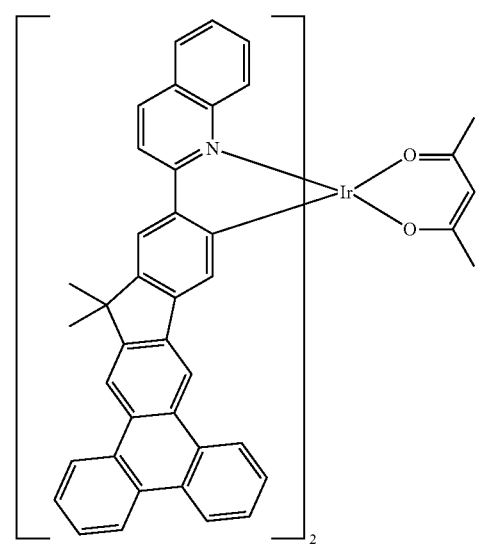

A mixture of 5.0 g of dichloro-bridged dimer, 2.3 g of sodium carbonate, 2.2 g of 2,4-pentanedione and 100 ml of 2-methoxyethanol, was placed under nitrogen, and then heated reflux overnight. After finishing the reaction, the mixture was allowed to cool to room temperature, the precipitate was vacuum filtered. The filtered product was added to 300 ml of distilled water and stirred for 30 minutes. The red precipitate was vacuum filtered, washed with additional distilled water, followed by several rinses with absolute ethanol followed by hexanes to give to give product 1.2 g (46%), the desired product was purified by vacuum sublimation.

Example 4

Synthesis of EX72

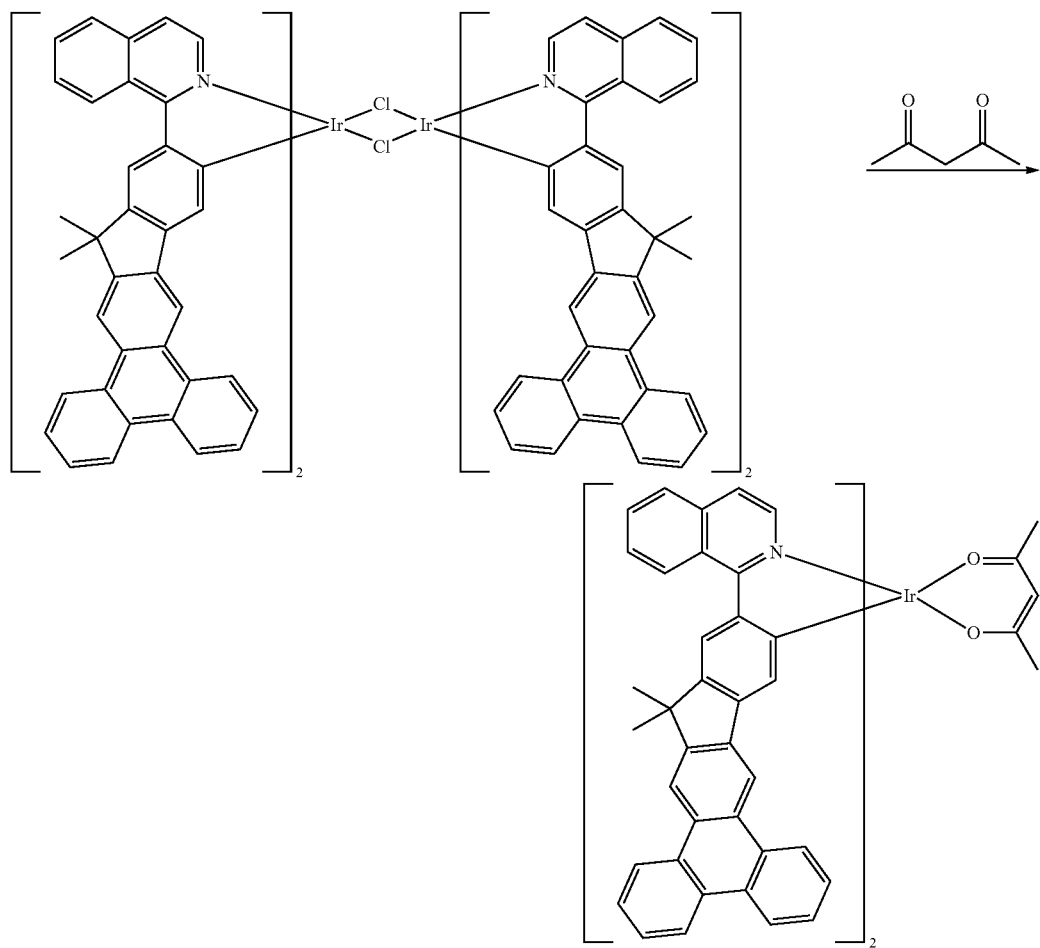

1-Bromoisoquinoline instead of 2-bromoquinoline, except for using the same method as in synthesis example 1, the desired compound of example 4 (1.3 g, yield=36%) was obtained.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N,N-Bis (naphthalene-1-yl)-N,N-bis (phenyl)-benzidine (NPB) is most widely used as the hole transporting layer, N-(biphenyl-4-yl)-9,9-dimethyl-N-(4'-phenylbiphenyl-4-yl)-9H-fluoren-2-amine (EB2) is used as electron blocking layer, and the chemical structure shown below:

127

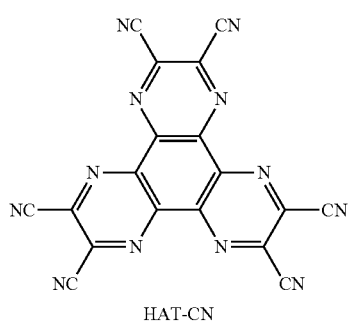

HAT-CN

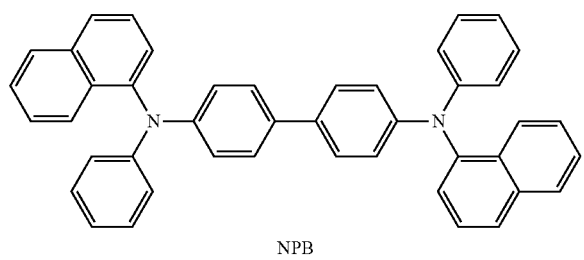

NPB

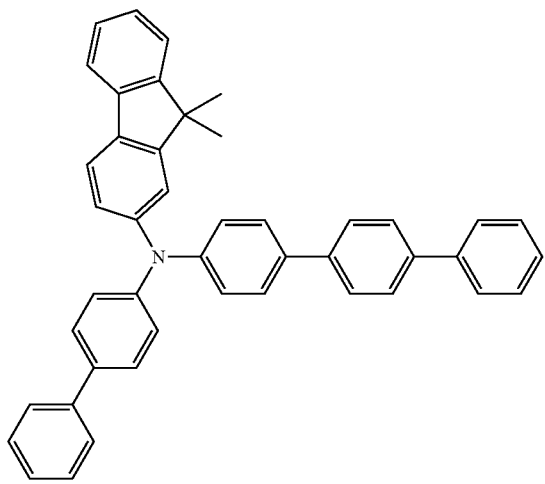

EB2

In the present invention the phosphorescent emitting host used as the following formulas:

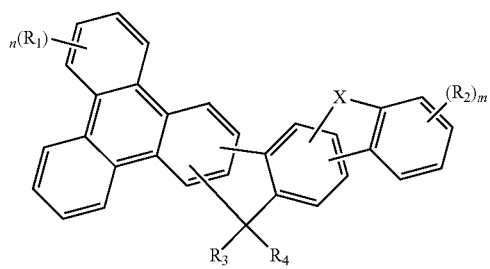

128
-continued

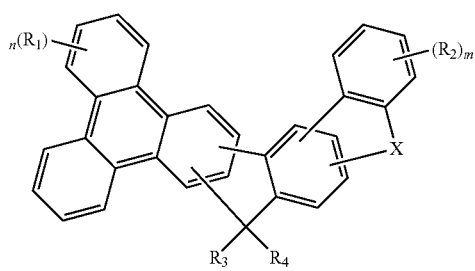

wherein X is a divalent bridge selected from the atom or group consisting from O, S, $C(R_8)_2$, $N(R_9)$ and $Si(R_{10})_2$, m represents an integer of 0 to 4, n represents an integer of 0 to 8, $R_1$ to $R_4$ and $R_8$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms; wherein the preferably phosphorescent light emitting host is selected from the group consisting of:

H1

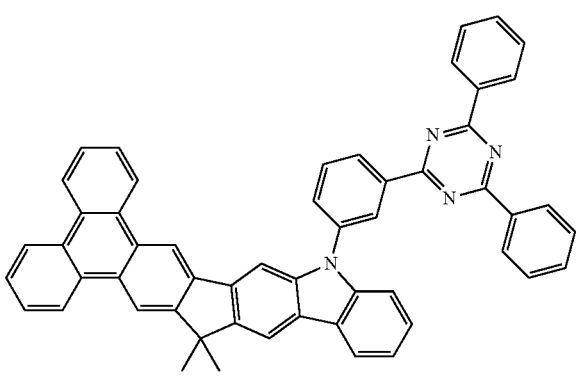

H2

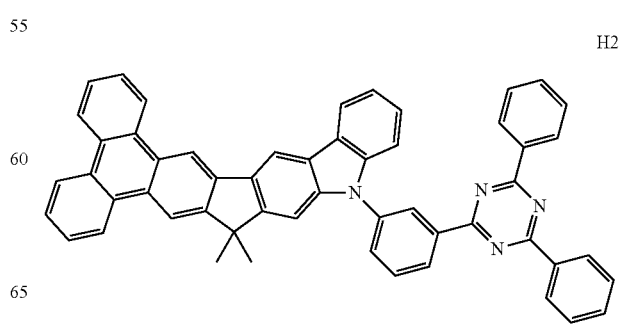

H3

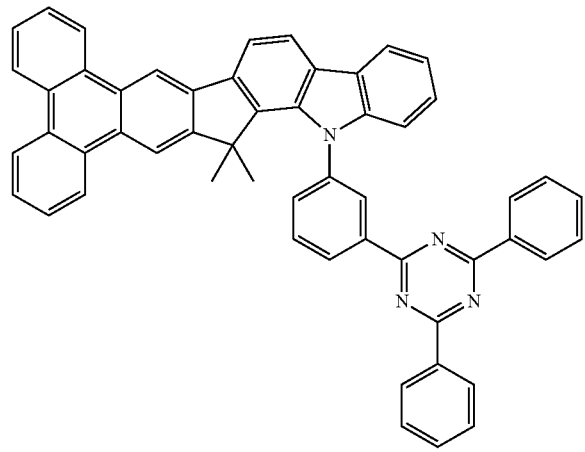

H4

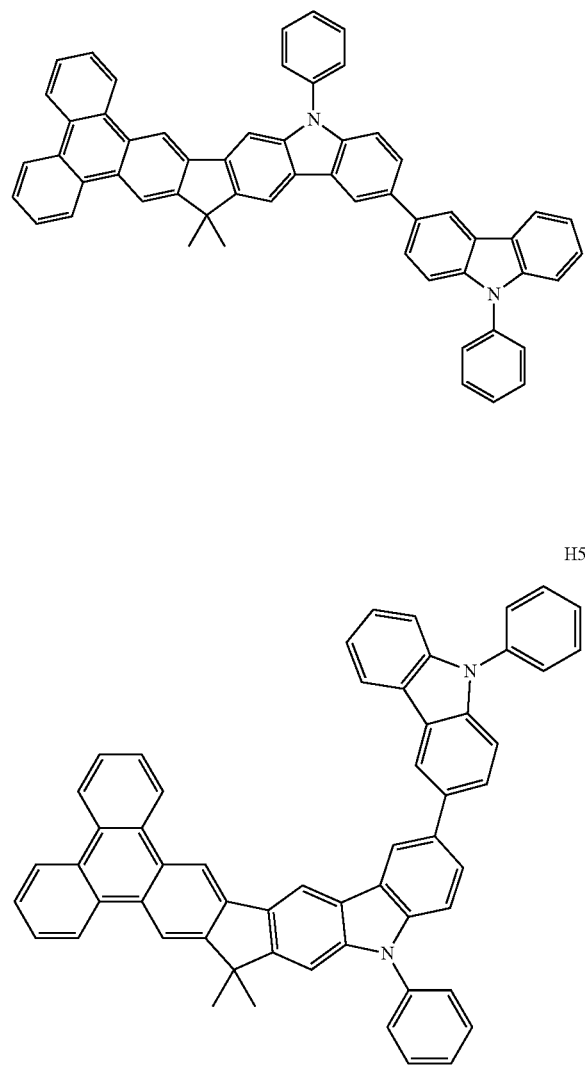

H5

H6

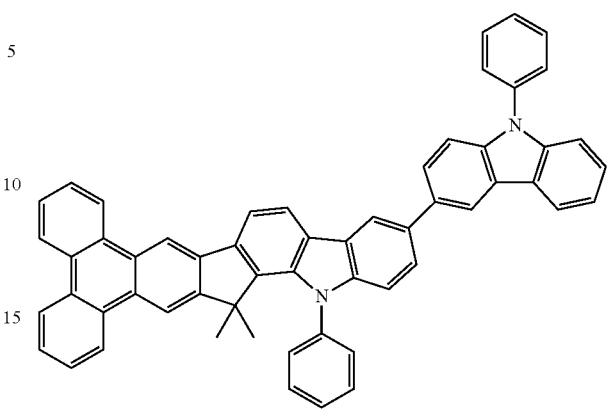

Organic iridium complexes are widely used as phosphorescent dopant for light emitting layer, $Ir(ppy)_3$, $Ir(piq)_2(acac)$ and $Ir(2\text{-}phq)_2(acac)$ are widely used for phosphorescent dopant of light emitting layer for comparable materials in the present invention.

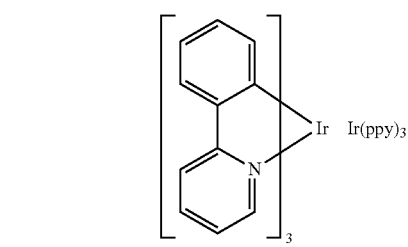

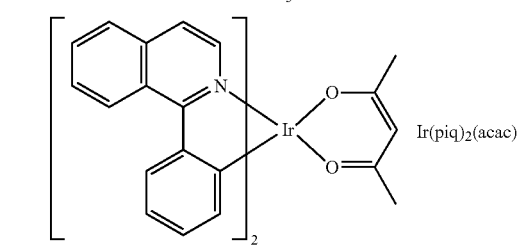

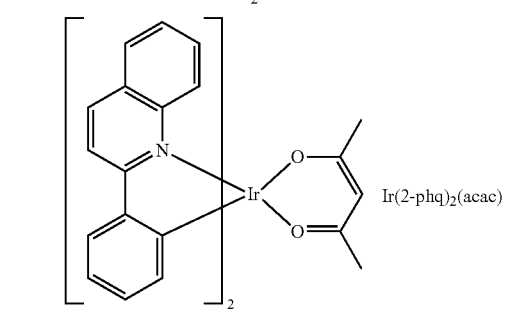

HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

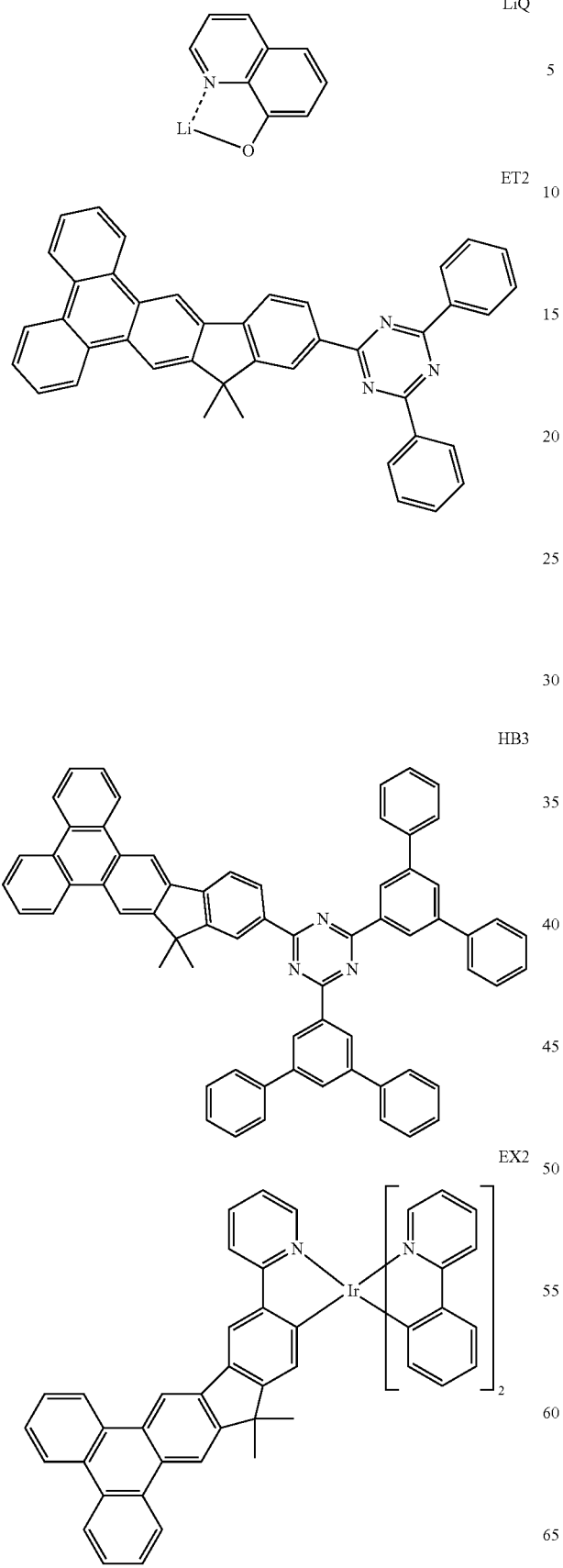
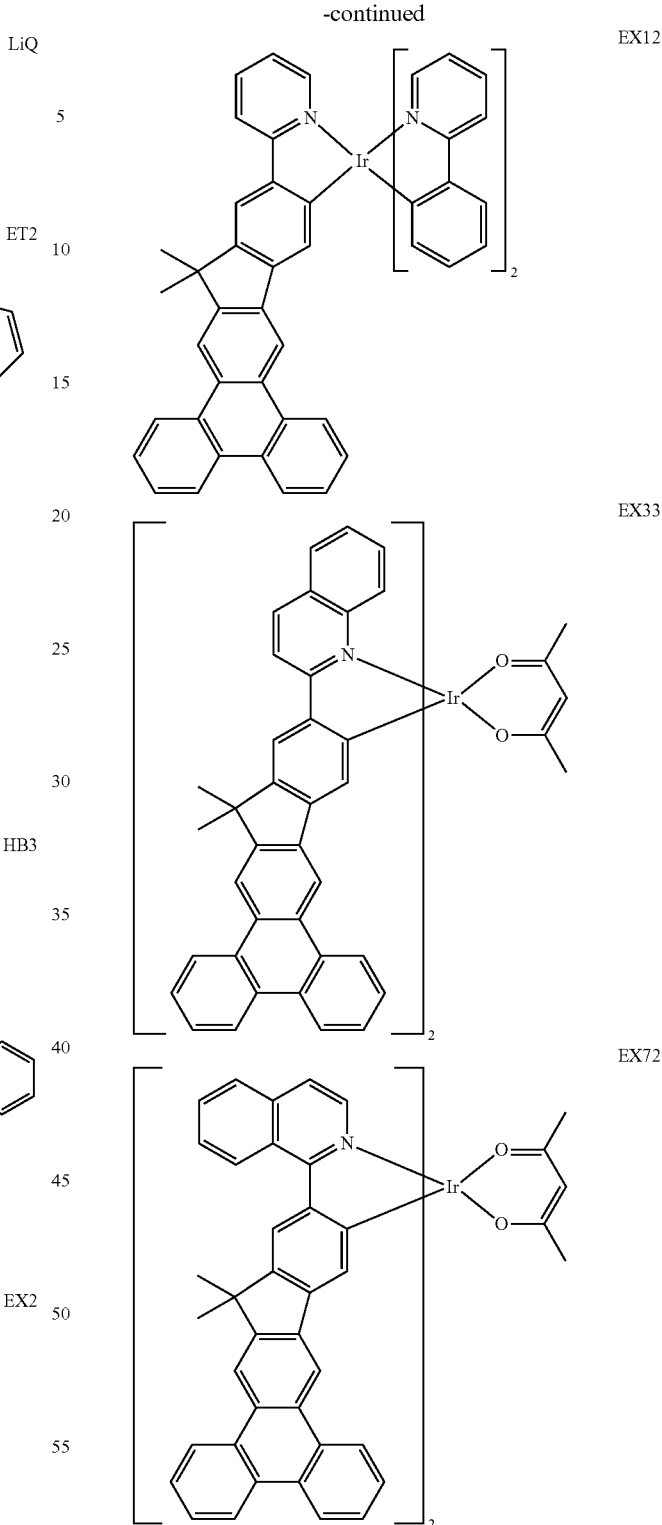

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 5

Using a procedure analogous to the above mentioned general method, phosphorescent emitting organic EL device having the following device structure was produced (See FIG. 1). Device: ITO/HAT-CN (20 nm)/NPB (110 nm)/EB2 (5 nm)/H1 to H6 doped 15% phosphorescent emitting dopant (30 nm)/HB3 (10 nm)/ET2 doped 40% LiQ (35 nm)/LiQ (1 nm)/Al (160 nm). The I-V-B (at 1000 nits) and half-life time of phosphorescent emitting organic EL device testing report as Table 1. The half-life time is defined that the initial luminance of 1000 cd/m$^2$ has dropped to half.

TABLE 1

| Emitting host | Emitting dopant | Voltage (V) | Efficiency (cd/A) | Color | Half-life time (hour) |
|---|---|---|---|---|---|
| H1 | EX2 | 3.5 | 45 | green | 1280 |
| H2 | Ir(ppy)$_3$ | 3.8 | 36 | green | 850 |
| H2 | EX2 | 3.5 | 48 | green | 1350 |
| H3 | EX12 | 3.6 | 40 | green | 1050 |
| H4 | EX12 | 3.8 | 28 | green | 1100 |
| H5 | EX2 | 4.0 | 21 | green | 1200 |
| H6 | Ir(ppy)$_3$ | 3.5 | 22 | green | 960 |
| H6 | EX12 | 3.5 | 18 | green | 1300 |
| H2 + H6 | EX2 | 4.2 | 56 | green | 1280 |
| H2 | EX33 | 4.0 | 14 | Red | 650 |
| H2 + H6 | EX33 | 4.5 | 17 | Red | 700 |
| H2 + H6 | Ir(piq)$_2$(acac) | 4.8 | 15 | Red | 310 |
| H3 | EX72 | 3.9 | 16 | orange | 800 |
| H3 + H6 | EX72 | 4.2 | 28 | orange | 850 |
| H3 + H6 | Ir(2-phq)$_2$(acac) | 4.5 | 18 | orange | 430 |

In the above preferred embodiments for phosphorescent organic EL device test report (see Table 1), we show that the indenotriphenylene-based iridium complexes with a general formula (1) used as light emitting dopant of emitting layer for organic EL device in the present invention display good performance than the prior art of organic EL materials. More specifically, the organic EL device in the present invention use the indenotriphenylene-based iridium complexes with a general formula (1) as light emitting dopant material to collocate with emitting host material H1 to H6 shown lower power consumption, longer half-life time and higher efficiency.

To sum up, the present invention discloses an thindeno triphenylene-based iridium complexes which can be used as light emitting dopant of emitting layer for organic EL device are disclosed. The mentioned the indenotriphenylene-based iridium complexes represented by the following formula (1):

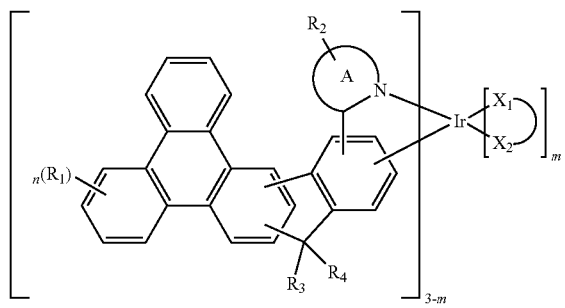

formula(1)

wherein A ring represents an imidazole, a pyridine, a quinoline and an isoquinoline, X$_1$-X$_2$ represents a bidentate ligand, m represents an integer of 0 to 2, n represents an integer of 0 to 8, R$_1$ to R$_4$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. An indenotriphenylene-based iridium complex represented by the following formula (1):

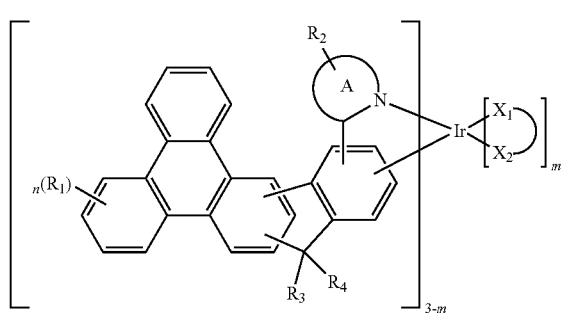

formula(1)

wherein ring A represents an imidazole, a pyridine, a quinoline and an isoquinoline, X$_1$-X$_2$ represents a bidentate ligand, m represents an integer of 0 to 2, n represents an integer of 0 to 8, R$_1$ to R$_4$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

2. The indenotriphenylene-based iridium complex according to claim 1, wherein X$_1$-X$_2$ represents one of the following formulas:

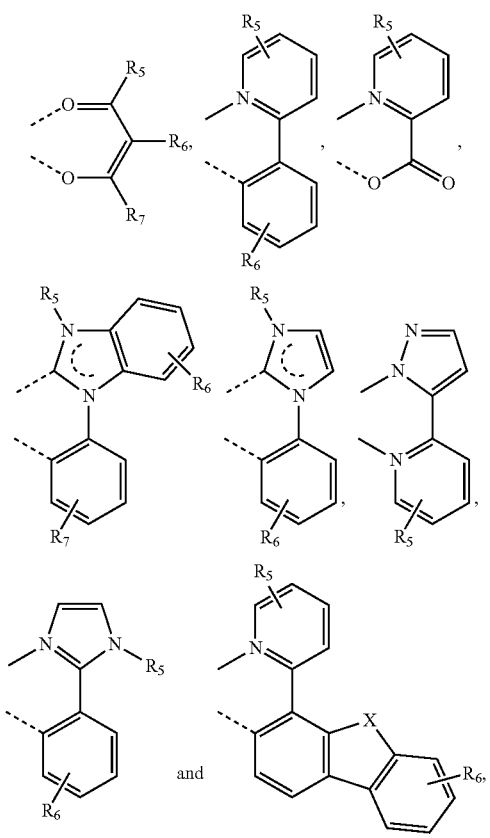

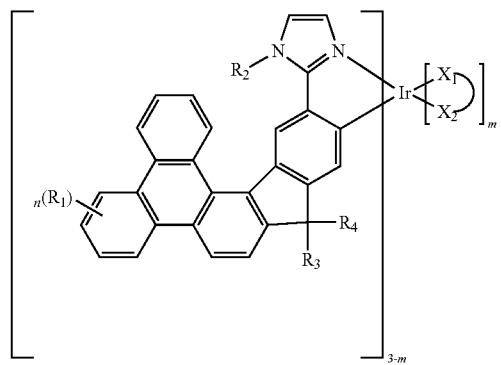

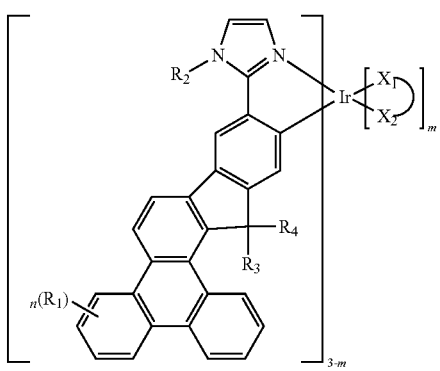

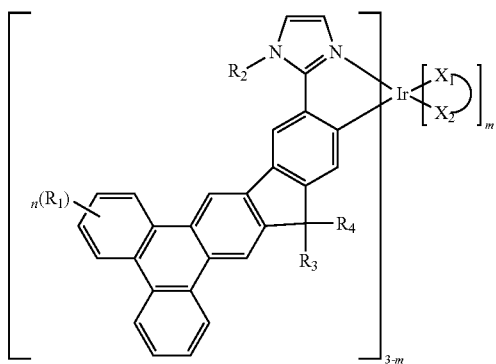

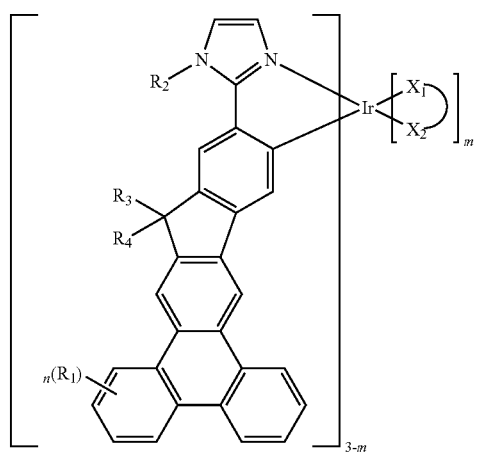

wherein X is a divalent bridge selected from the atom or group consisting from O, S, $C(R_8)_2$, $N(R_9)$ and $Si(R_{10})_2$, $R_5$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

3. The indenotriphenylene-based iridium complex according to claim 1, wherein the indenotriphenylene-based iridium complex of formula (1) is represented by one of the following formula (2) to formula (31):

formula(6)
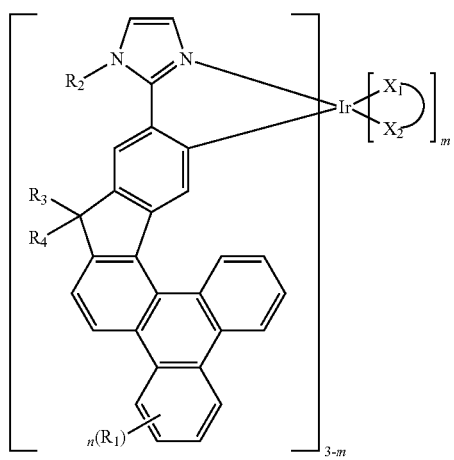
formula(9)
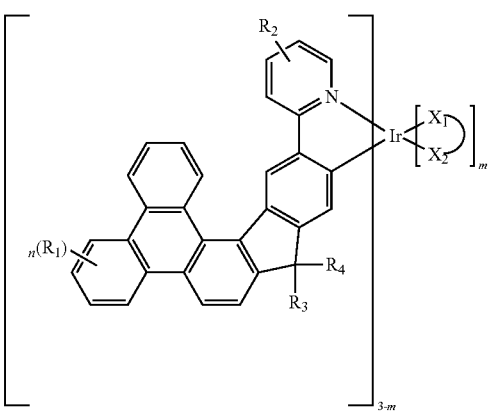
formula(7)
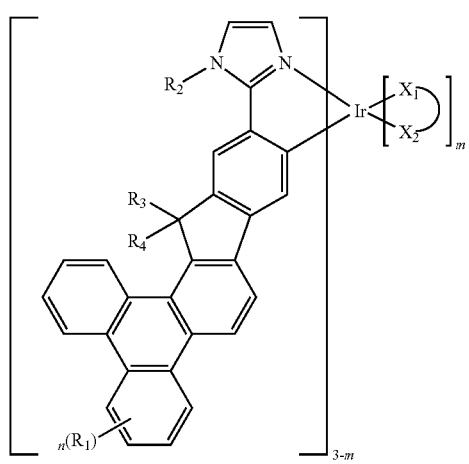
formula(10)
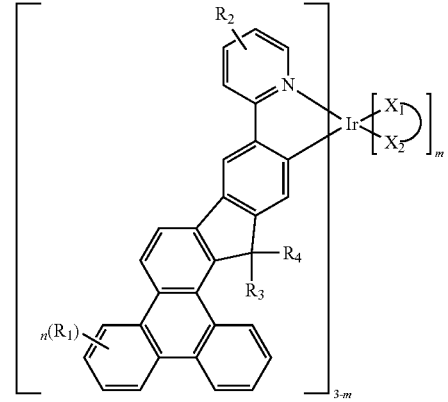
formula(8)
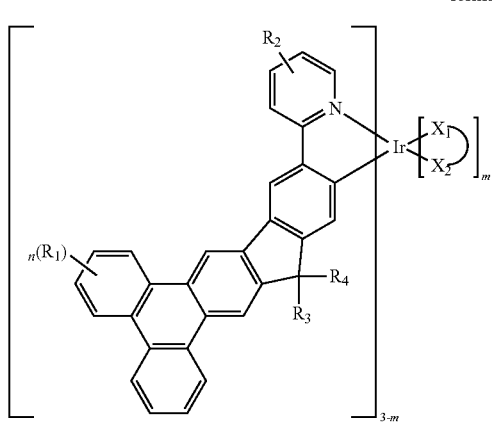
formula(11)
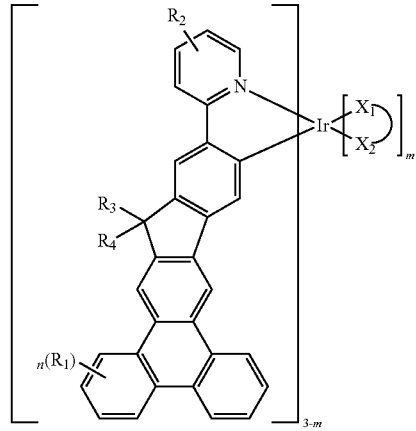

formula(12)
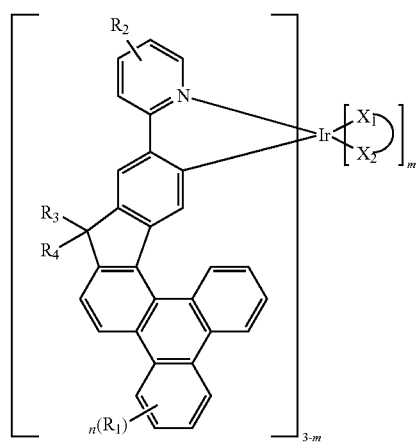
formula(13)
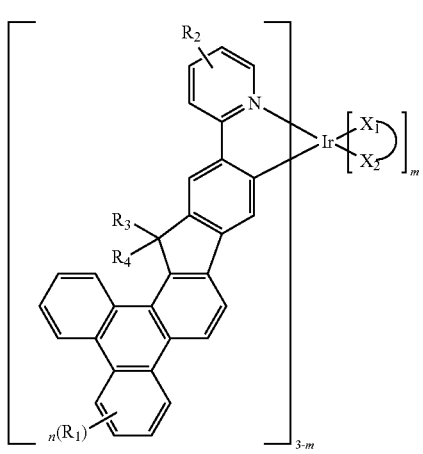
formula(14)
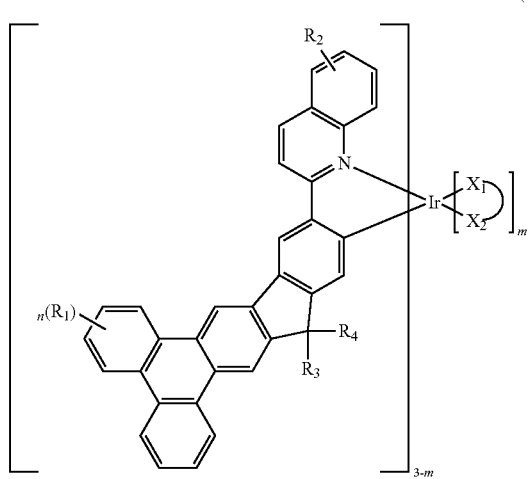
formula(15)
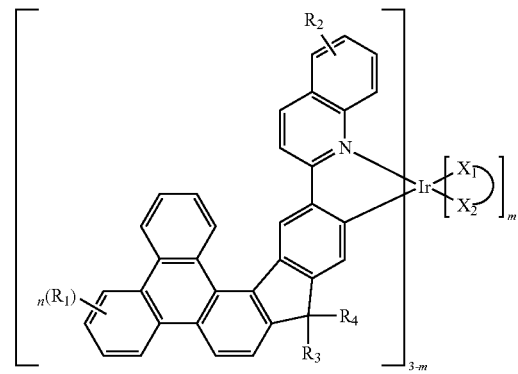
formula(16)
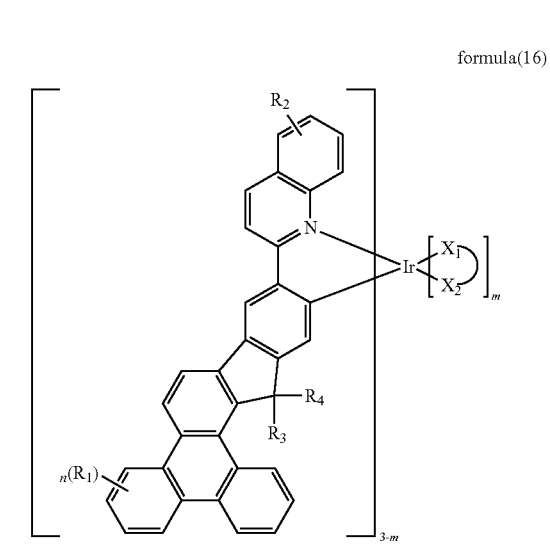
formula(17)
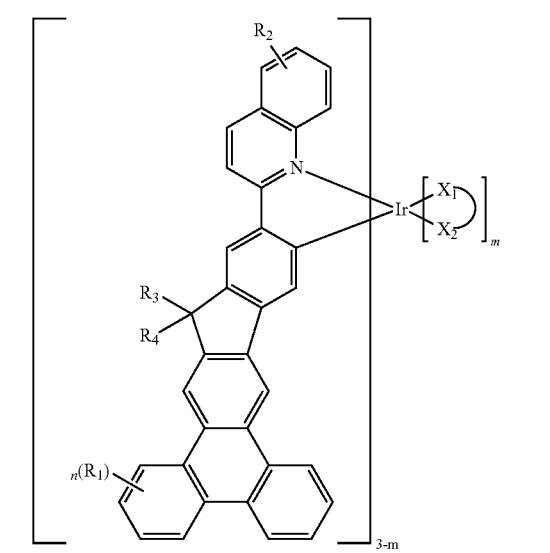

formula(18)
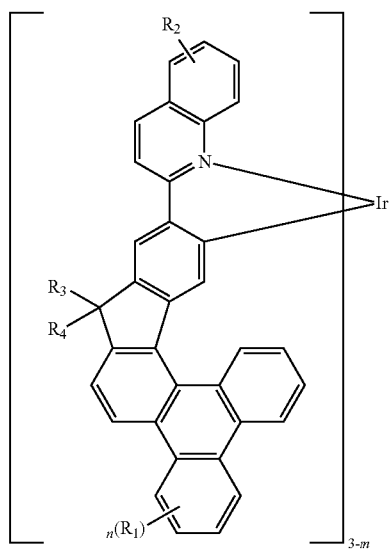
formula(19)
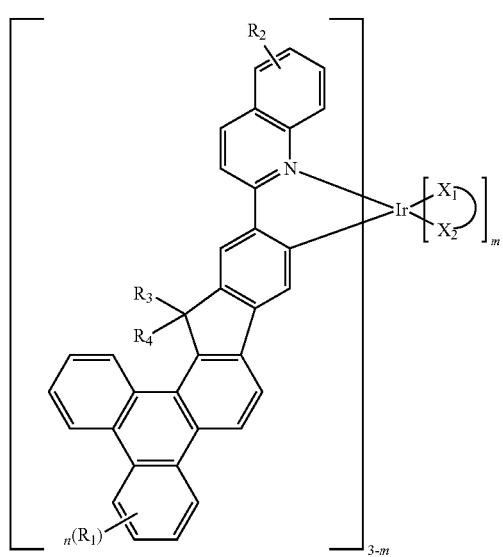
formula(20)
formula(21)
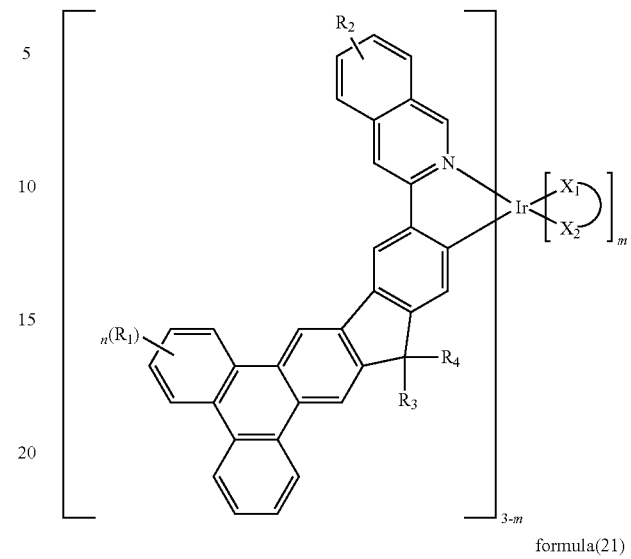
formula(22)
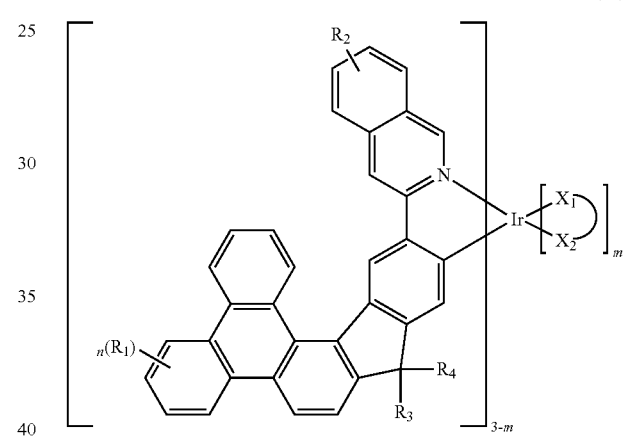
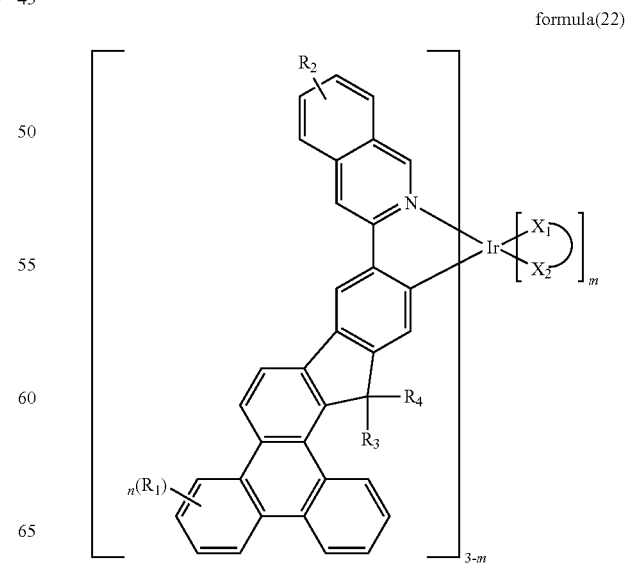

formula(23)
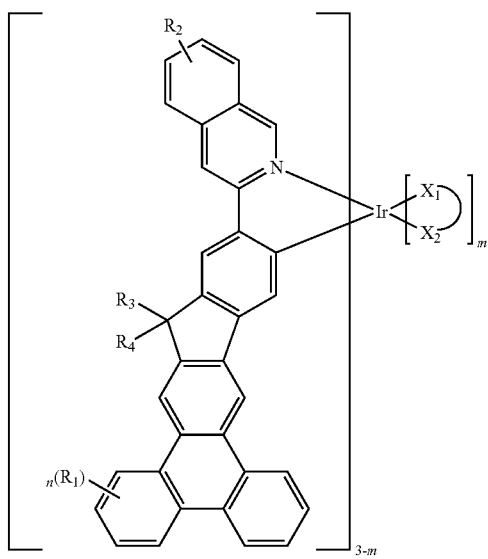
formula(24)
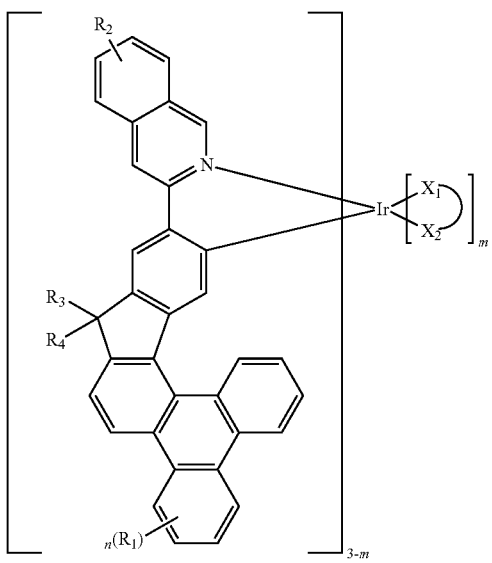
formula(25)
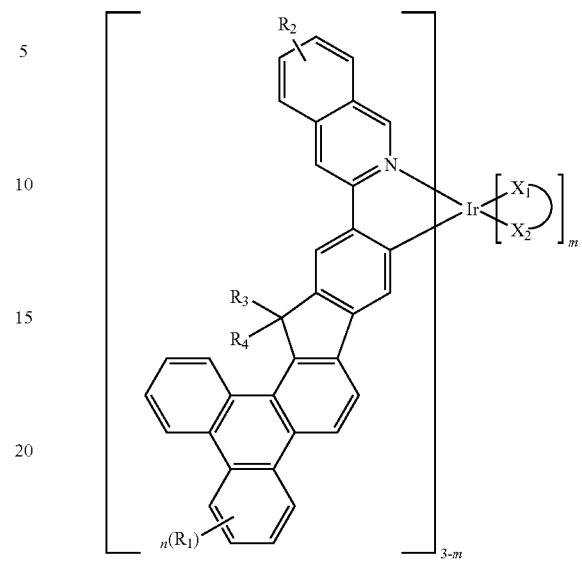
formula(26)
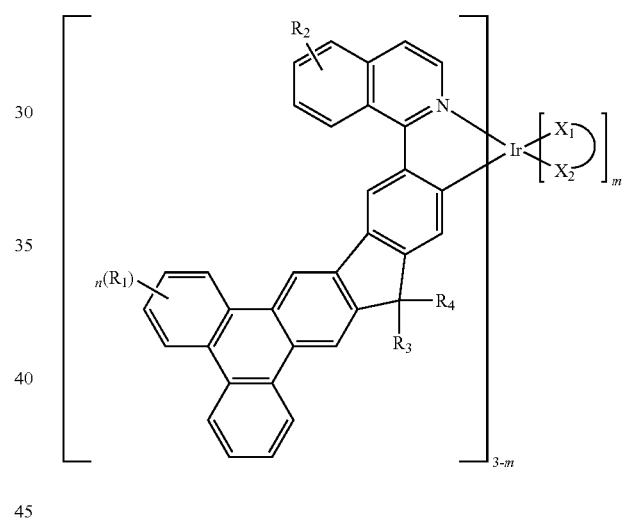
formula(27)
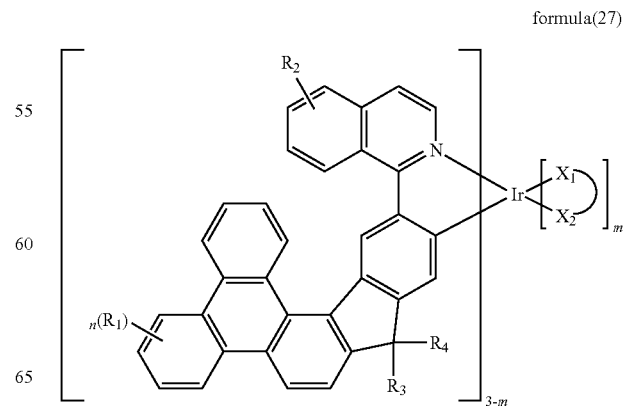

formula(28)

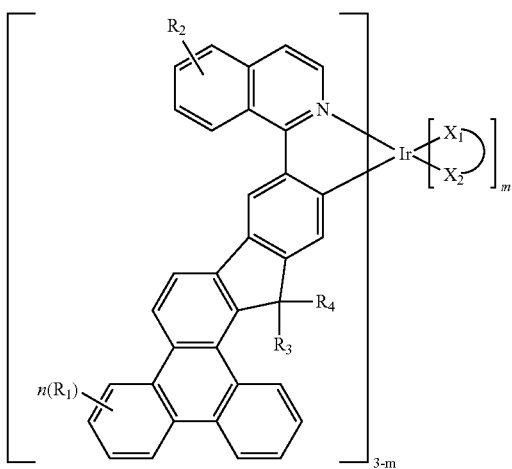

formula(31)

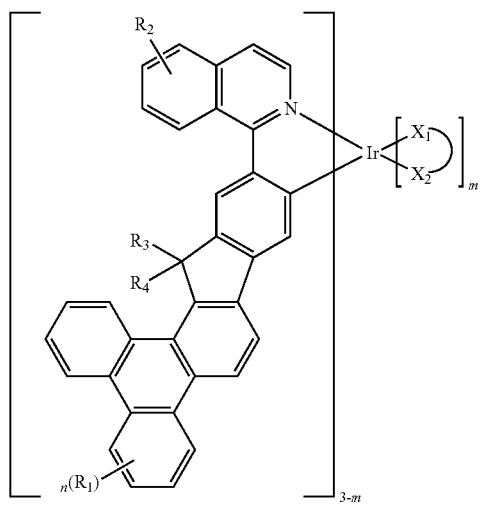

formula(29)

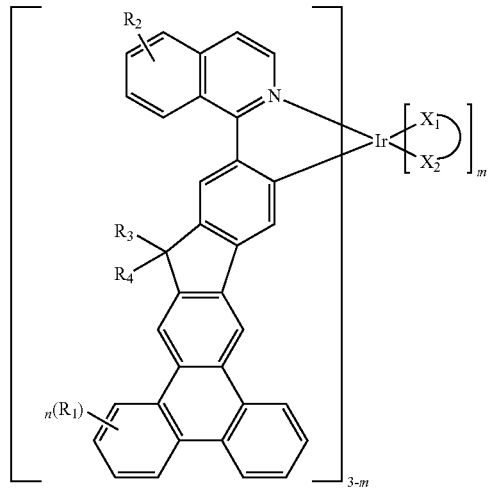

wherein $X_1$-$X_2$ represents a bidentate ligand, m represents an integer of 0 to 2, n represents an integer of 0 to 8, $R_1$ to $R_4$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

4. The indenotriphenylene-based iridium complex according to claim 3, wherein $X_1$-$X_2$ represents one of the following formulas:

formula(30)

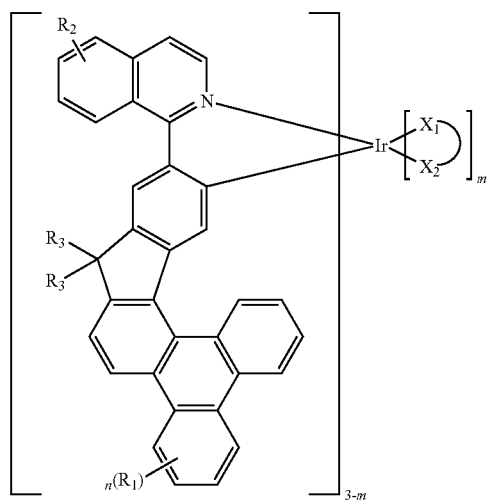

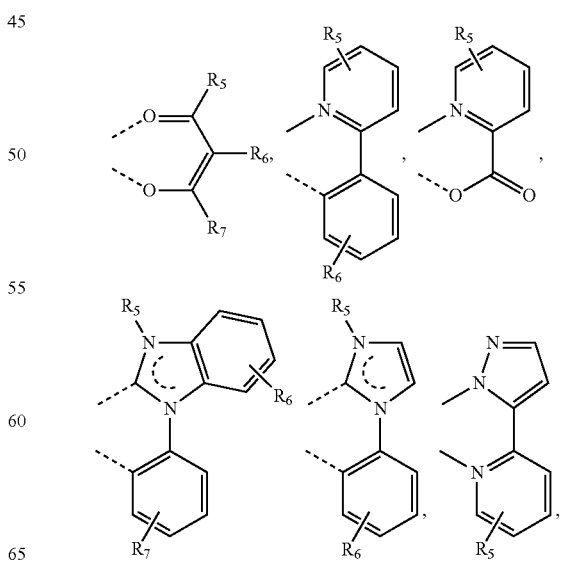

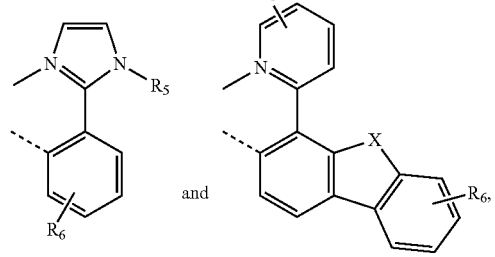

wherein X is a divalent bridge selected from the atom or group consisting from O, S, C(R$_8$)$_2$, N(R$_9$) and Si(R$_{10}$)$_2$, R$_5$ to R$_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

5. An organic electroluminescent device comprising a pair of electrodes consisting of a cathode and an anode, and a light emitting layer and one or more organic thin film layer between the pair of electrodes, wherein at least one of the organic thin film layer and the light emitting layer comprises the indenotriphenylene-based iridium complex of claim 1.

6. The organic electroluminescent device according to claim 5, wherein the light emitting layer comprises an emitting dopant of the indenotriphenylene-based iridium complex of formula (1).

7. The organic electroluminescent device according to claim 5, wherein the light emitting layer comprises two or three types of emitting dopant of the indenotriphenylene-based iridium complex of formula (1).

8. The organic electroluminescent device according to claim 5, wherein the light emitting layer comprises an emitting host with one of the following formulas:

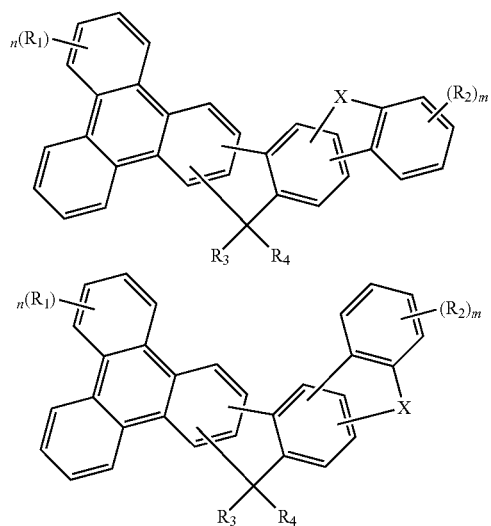

wherein X is a divalent bridge selected from the atom or group consisting from O, S, C(R$_8$)$_2$, N(R$_9$) and Si(R$_{10}$)$_2$, m represents an integer of 0 to 4, n represents an integer of 0 to 8, R$_1$ to R$_4$ and R$_8$ to R$_{10}$ are independently selected from the group consisting of a hydrogen atom, a halide, substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

9. The organic electroluminescent device according to claim 8, wherein the light emitting host is selected from the group consisting of:

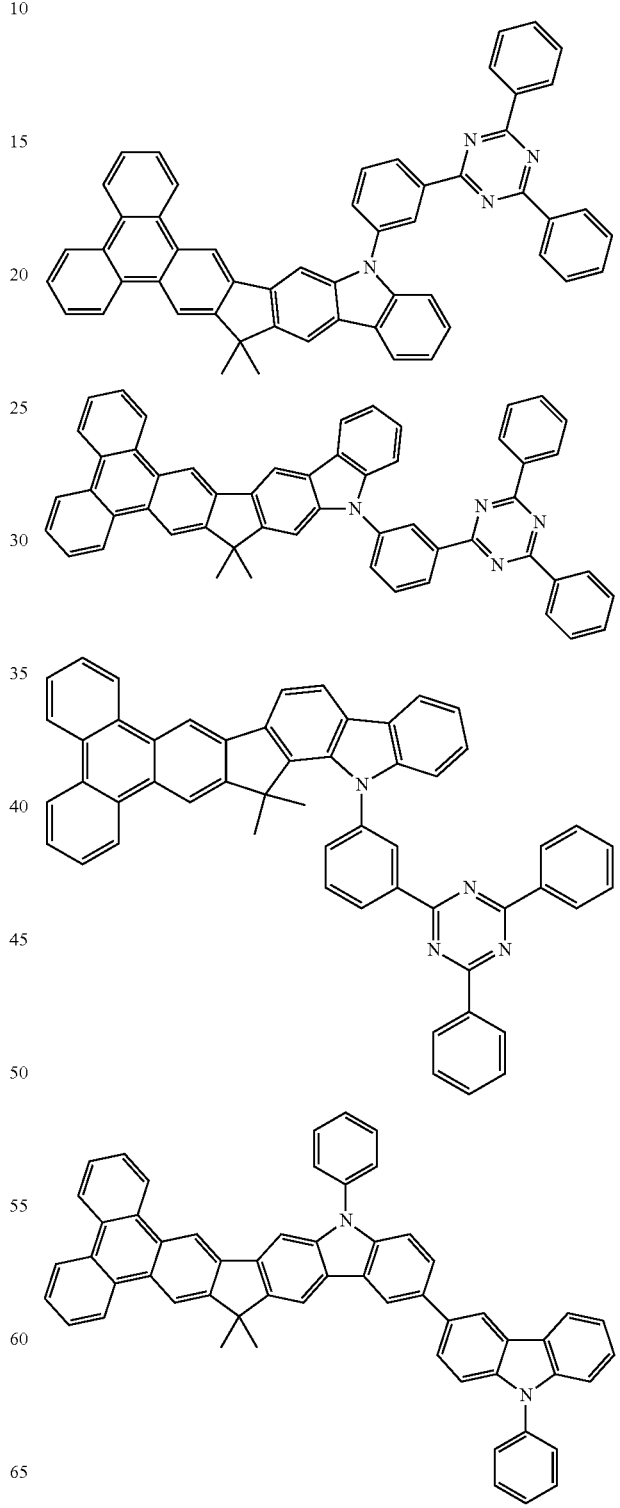

-continued

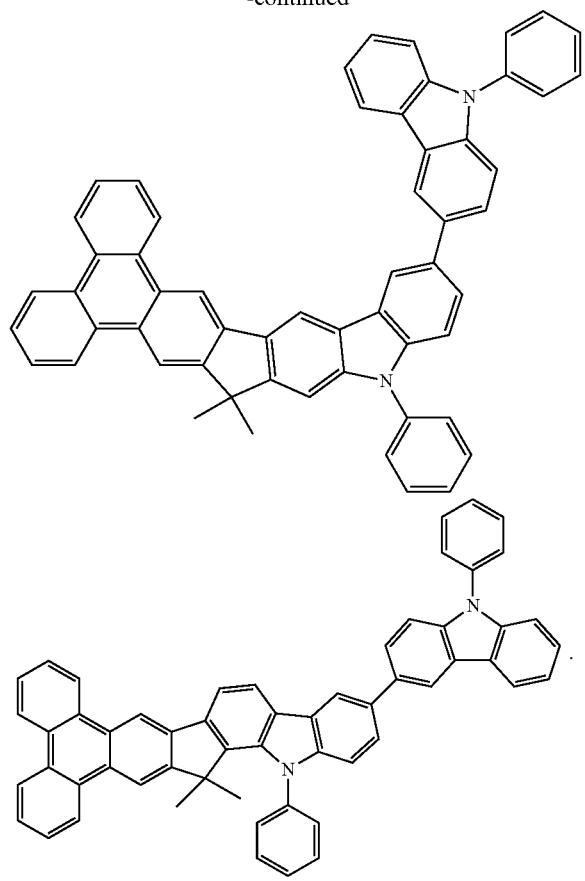

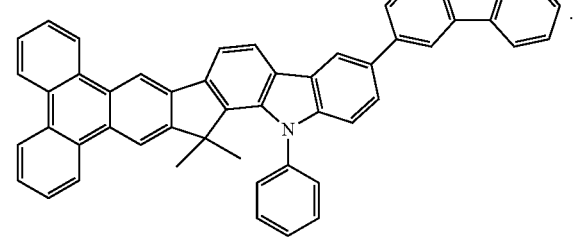

10. The organic electroluminescent device according to claim 5, wherein the light emitting layer comprises two or three types of emitting host with one of the following formulas:

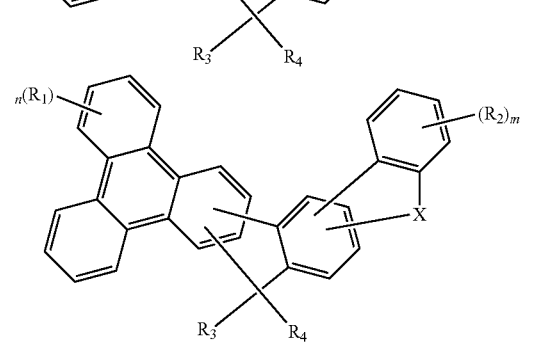

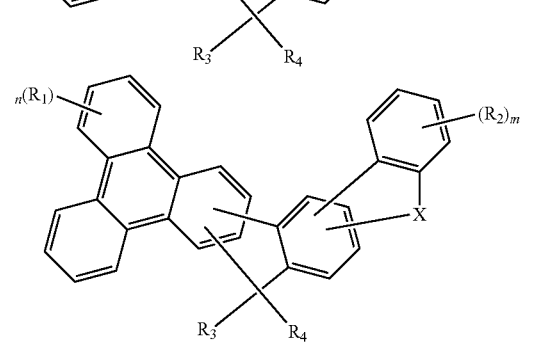

wherein X is a divalent bridge selected from the atom or group consisting from O, S, $C(R_8)_2$, $N(R_9)$ and $Si(R_{10})_2$, m represents an integer of 0 to 4, n represents an integer of 0 to 8, $R_1$ to $R_4$ and $R_8$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

11. The organic electroluminescent device according to claim 10, wherein the emitting host are selected from the group consisting of:

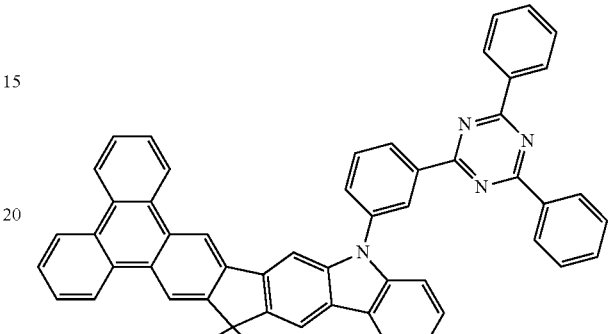

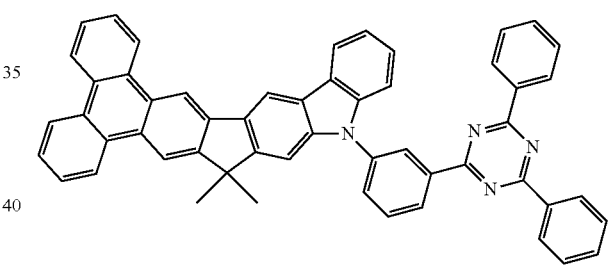

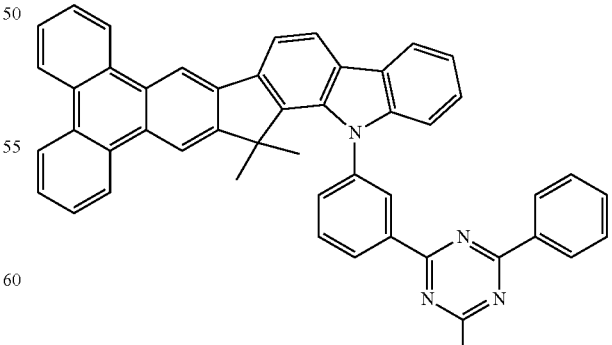

151
-continued

152
-continued

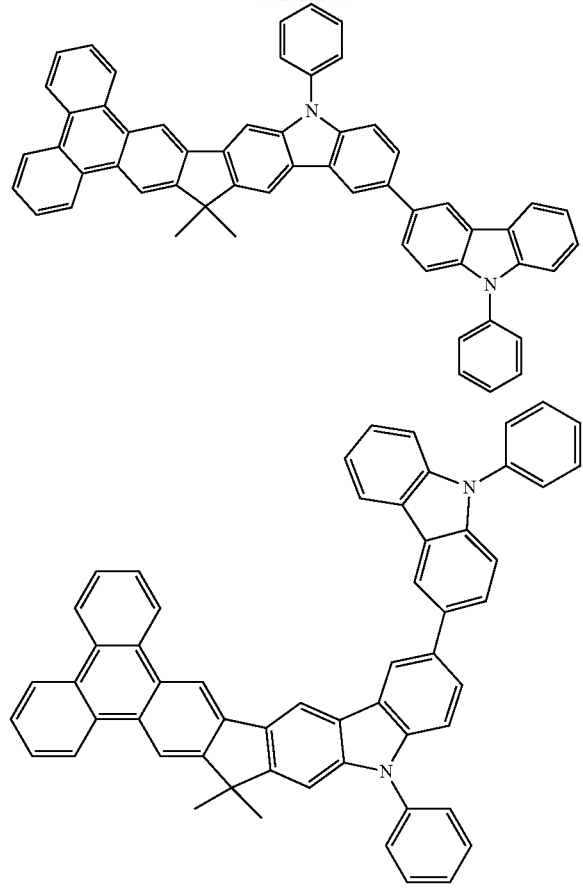

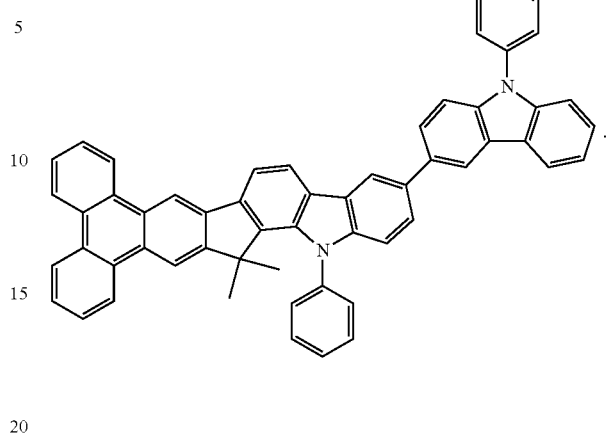

12. The organic electroluminescent device according to claim 5, wherein the light emitting layer emits phosphorescent red, blue, green or yellow lights.

13. The organic electroluminescent device according to claim 5, wherein the device is an organic light emitting device.

14. The organic electroluminescent device according to claim 5, wherein the device is a lighting panel.

* * * * *